US007741448B2

(12) United States Patent
Yanagisawa et al.

(10) Patent No.: US 7,741,448 B2

(45) Date of Patent: Jun. 22, 2010

(54) ANTIBODY HAVING INHIBITORY EFFECT ON AMYLOID FIBRIL FORMATION

(75) Inventors: Katsuhiko Yanagisawa, c/o National Center for Geriatrics and Gerontology, 36-3, Gengo, Morioka-cho, Obu-shi, Aichi 4748511 (JP); Masao Shibata, Minamiminowa-mura (JP)

(73) Assignees: Medical & Biological Laboratories Co., Ltd., Nagoya-shi (JP); The President of National Center for Geriatrics and Gerontology, Obu-shi (JP); Katsuhiko Yanagisawa, Obu-shi (JP)

( * ) Notice: Subject to any disclaimer, the term of this patent is extended or adjusted under 35 U.S.C. 154(b) by 103 days.

(21) Appl. No.: 11/922,482

(22) PCT Filed: Jun. 19, 2006

(86) PCT No.: PCT/JP2006/312226

§ 371 (c)(1), (2), (4) Date: Dec. 19, 2007

(87) PCT Pub. No.: WO2006/137354

PCT Pub. Date: Dec. 28, 2006

(65) Prior Publication Data

US 2009/0110682 A1 Apr. 30, 2009

(30) Foreign Application Priority Data

Jun. 21, 2005 (JP) ............................ 2005-180334

(51) Int. Cl.
*C07K 16/18* (2006.01)
*C12P 21/08* (2006.01)

(52) U.S. Cl. ............... 530/387.3; 530/388.1; 530/387.1

(58) Field of Classification Search ....................... None
See application file for complete search history.

(56) References Cited

U.S. PATENT DOCUMENTS

| | | | | |
|---|---|---|---|---|
| 5,861,155 A * | 1/1999 | Lin | ......................... | 424/133.1 |
| 2004/0181042 A1* | 9/2004 | Yanagisawa et al. | ... | 530/388.25 |
| 2006/0105389 A1* | 5/2006 | Kordyum et al. | ............. | 435/7.1 |

FOREIGN PATENT DOCUMENTS

EP 1420032 5/2004

OTHER PUBLICATIONS

Rudikoff S et al. Single amino acid substitution altering antigen-binding specificity. Proc Natl Acad Sci USA, 1982; 79(6):1979-1983.*

Paul WE, Ed. Fundamental Immunology, Third Edition. Raven Press, New York, 1993, pp. 292-295.*

Padlan EA et al. Structure of an antibody-antigen complex: Crystal structure of the HyHEL-10 Fab-Iysozyme complex. Proc Natl Acad Sci USA, 1989; 86:5938-5942.*

K. Yanagisawa et al., "GM1 ganglioside-bound amyloid β-protein (Aβ): A possible form of preamyloid in Alzheimer's disease," Nat. Med. 1, No. 10, Oct. 1995, pp. 1062-1066.

K. Yanagisawa et al., "GM1 Ganglioside-bound amyloid β- protein in Alzheimer's disease brain," Neurobiol. Aging, vol. 19, No. 1S, 1998, pp. S65-S67.

J. McLaurin et al., "Membrane Disruption by Alzheimer β-Amyloid Peptides Mediated through Specific Binding to Either Phospholipids or Gangliosides," J. Biol. Chem. vol. 271, No. 43, 1996, pp. 26482-26489.

L. P. Choo-Smith et al., "The interaction between Alzheimer amyloid β(1-40) peptide and ganglioside $G_{M1}$-containing membranes," FEBS Letters, vol. 402, 1997, pp. 95-98.

J. McLaurin et al., "Characterization of the interactions of Alzheimer β-amyloid peptides with phospholipid membranes," Eur J Biochem. 245(2), 1997, pp. 355-363.

L. P.Choo-Smith et al., "Acceleration of Amyloid Fibril Formation by Specific Binding of Aβ-(1-40) Peptide to Ganglioside-containing Membrane Vesicles," J. Biol. Chem., vol. 272, No. 37, 1997, pp. 22987-22990.

K. Matsuzaki et al., "Interactions of Amyloid β-Peptide (1-40) with Ganglioside-Containing Membranes," Biochemistry 38, 1999, pp. 4137-4142.

V. Koppaka et al., "Accelerated Accumulation of Amyloid β Protein on Oxidatively Damaged Lipid Membranes," Biochemistry 39, 2000, pp. 10011-10016.

A. Kakio et al., "Cholesterol-dependent Formation of GM1 Ganglioside-bound Amyloid (β-Protein, an Endogenous Seed for Alzheimer Amyloid," J.Biol. Chem, vol. 276, No. 27, 2001, pp. 24985-24990.

U. Igbavboa et al.. "Increasing Age Alters Transbilaver Fluidity and Cholesterol Asymmetry in Synaptic Plasma Membranes of Mice," J. Neurochem., vol. 66, No. 4, 1996, pp. 1717-1725.

U. Igbavboa, et al., "Transbilayer Distribution of Cholesterol Is Modified in Brain Synaptic Plasma Membranes of Knockout Mice Deficient in the Low-Density Lipoprotein Receptor, Apolipoptotein E, or Both Proteins," J. Neurochem. vol. 69, No. 4, 1997, pp. 1661-1667.

R. G. Parton, "Ultrastructural Localization of Gangliosides; GM1 is Concentrated in Caveolae," J. Histochem. Cytochem. vol. 42, No. 2, 1994, pp. 155-166.

K. Simons et al., "Functional rafts in cell membranes," Nature vol. 387, Jun. 1997, pp. 569-572.

S. J. Lee et al., "A detergent-insoluble membrane compartment contains Aβ in vivo," Nat. Med. vol. 4, No. 6, Jun. 1998, pp. 730-734.

M. Morishima-Kawashima et al., "The Presence of Amyloid β-Protein in the Detergent-Insoluble Membrane Compartment of Human Neuroblastoma Cells," Biochemistry, vol. 37, No. 44, Nov. 1998, pp. 15274-15253.

(Continued)

*Primary Examiner*—Daniel E. Kolker
*Assistant Examiner*—Kimberly A. Ballard
(74) *Attorney, Agent, or Firm*—Edwards Angell Palmer & Dodge LLP

(57) ABSTRACT

Disclosed is an antibody having a high inhibitory effect on amyloid fibril formation. An antibody is produced by using a liposome containing a GM1 ganglioside at a predetermined ratio as an immunogen. Thus, the sequences of four types of antibodies each having a high inhibitory effect on amyloid fibril formation can be provided.

4 Claims, 18 Drawing Sheets

OTHER PUBLICATIONS

N. Sawamura et al., "Mutant Presenilin 2 Transgenic Mice," J. Biol. Chem., vol. 275, No. 36, 2000, pp. 27901-27908.

Katsuhiko Yanagisawa et al., "Amyloid- β-protein (Aβ) associated with lipid molecules: immunoreactivity distinct from that of soluble Aβ,"FEBS Letters 420,1997, pp. 43-46.

Hideki Hayashi et al., "A Seed for Alzheimer Amyloid in the Brain," J Neurosci., 24(20), May 2004, pp. 4894-4902.

Katsuhiko Yanagisawa, Heisei 14 Nendo Sokatsu Buntan Kenkyu Hokokusho, 2004, pp. 11-14.

* cited by examiner

Aβ 1-40
binding Aβ 1-40 (fmol)
80000
60000
40000
20000
0
GM1 molecular ratio (%)
0
5
10
20
30
40
cholesterol molecular ratio (%)
12
16
20
30
40

Fig.3

| liposome | molecular ratio |
|---|---|
| SM : Cho1 : GM1 | ①75 : 20 : 5 |
| | ②50 : 40 : 10 |
| | ③70 : 20 : 10 |
| | ④64 : 16 : 20 |
| | ⑤40 : 40 : 20 |
| | ⑥50 : 20 : 30 |
| | ⑦30 : 40 : 30 |
| | ⑧30 : 30 : 40 |
| | ⑨48 : 12 : 40 |

Fig.4

| clone | class | Aβ fibril formation rate (%) * | | |
|---|---|---|---|---|
| | | fibrous Aβ ** | GAβ40 | GAβ42 |
| 4396C | IgG2a | 5.4 | 55.6 | 66.2 |
| 4G8*** | IgG1 | 97 | 98.5 | 95.4 |
| 1C9 | IgM | 11.1 | 91 | 87.6 |
| 2E12 | IgM | 19.2 | -4.9 | -4.9 |
| 3G11 | IgM | 21.3 | -2 | -0.4 |
| 4E11 | IgG2b | 10.7 | 27.7 | -4.9 |

Fig.9

```
         10        20        30        40        50        60
caggtgcaactgcagcagtctggacctgtgctggtgaagcctggggcttcagtgaagatg
Q  V  Q  L  Q  Q  S  G  P  V  L  V  K  P  G  A  S  V  K  M
                              CDR1
         70        80        90       100       110       120
tcctgtaaggcttctggatacacattcactgactactatatgaactgggtgaagcagagc
S  C  K  A  S  G  Y  T  F  T  D  Y  Y  M  N  W  V  K  Q  S
                                                  CDR2
        130       140       150       160       170       180
catggaaagagccttgagtggattggagttattaatccttacaacggtggtactagctac
H  G  K  S  L  E  W  I  G  V  I  N  P  Y  N  G  G  T  S  Y

        190       200       210       220       230       240
aaccagaagttcaagggcaaggccacattgactgttgacaagtcctccagcacagcctac
N  Q  K  F  K  G  K  A  T  L  T  V  D  K  S  S  S  T  A  Y

        250       260       270       280       290       300
atggagctcaacagcctgacatctgaggactctgcagtctattactgtgcaagagagggc
M  E  L  N  S  L  T  S  E  D  S  A  V  Y  Y  C  A  R  E  G
        CDR3
        310       320       330       340       350       360
tacggtagtagctacagggctatggactactggggccaagggaccacggtcaccgtctcc
Y  G  S  S  Y  R  A  M  D  Y  W  G  Q  G  T  T  V  T  V  S

        370
tca
S
```

Fig.10

```
        10        20        30        40        50        60
gacatcgagctcactcagtctccagcaatcatgtctgcatctctaggggaacgggtcacc
D  I  E  L  T  Q  S  P  A  I  M  S  A  S  L  G  E  R  V  T
                       CDR1
        70        80        90        100       110       120
atgacctgcactgccagctcaagtgtaagttccagttacttgcactggtaccagcagaag
M  T  C  T  A  S  S  S  V  S  S  S  Y  L  H  W  Y  Q  Q  K
                                          CDR2
       130       140       150       160       170       180
ccaggatcctcccccaaactctggatttatagcacatccaacctggcttctggagtccca
P  G  S  S  P  K  L  W  I  Y  S  T  S  N  L  A  S  G  V  P

       190       200       210       220       230       240
gctcgcttcagtggcagtgggtctgggacctcttactctctcacaatcagcagcatggag
A  R  F  S  G  S  G  S  G  T  S  Y  S  L  T  I  S  S  M  E
                                          CDR3
       250       260       270       280       290       300
gctgaagatgctgccacttattactgccaccagtatcatcgttccccacggacgttcggt
A  E  D  A  A  T  Y  Y  C  H  Q  Y  H  R  S  P  R  T  F  G

       310       320       330
ggaggcaccaagctggaaatcaaacgg
G  G  T  K  L  E  I  K  R
```

Fig.11

```
        10        20        30        40        50        60
caggtccaactgcagcagtcaggtggaggattggtgcagcctaaagggtcattgaaactc
 Q  V  Q  L  Q  Q  S  G  G  G  L  V  Q  P  K  G  S  L  K  L
                   CDR1
        70        80        90       100       110       120
tcatgtgcagcctctggattcaccttcaatacctacgccatgaactgggtccgccaggct
 S  C  A  A  S  G  F  T  F  N  T  Y  A  M  N  W  V  R  Q  A
                                          CDR2
       130       140       150       160       170       180
ccaggaaagggtttggaatgggttgctcgcataagaagtaaaagtaataattatgcaaca
 P  G  K  G  L  E  W  V  A  R  I  R  S  K  S  N  N  Y  A  T

       190       200       210       220       230       240
tattatgccgattcagtgaaagacaggttcaccatctccagagatgattcacaaagcatg
 Y  Y  A  D  S  V  K  D  R  F  T  I  S  R  D  D  S  Q  S  M

       250       260       270       280       290       300
ctctatctgcaaatgaacaacttgaaaactgaggacacagccatgtattactgtgtgaga
 L  Y  L  Q  M  N  N  L  K  T  E  D  T  A  M  Y  Y  C  V  R
     CDR3
       310       320       330       340       350
cgggttgcttactggggccaagggaccacggtcaccgtctcctca
 R  V  A  Y  W  G  Q  G  T  T  V  T  V  S  S
```

Fig.12

```
        10        20        30        40        50        60
gacatccagatgacacagtctccagcatccctgtccatggctataggagaaaaagtcacc
D  I  Q  M  T  Q  S  P  A  S  L  S  M  A  I  G  E  K  V  T
                    CDR1
        70        80        90        100       110       120
atcagatgcataaccagcactgatattgatgatgatatgaactggtaccagcagaagcca
I  R  C  I  T  S  T  D  I  D  D  D  M  N  W  Y  Q  Q  K  P
                              CDR2
        130       140       150       160       170       180
ggggaacctcctaagctccttatttcagaaggcaatactcttcgtcctggagtcccatcc
G  E  P  P  K  L  L  I  S  E  G  N  T  L  R  P  G  V  P  S

        190       200       210       220       230       240
cgattctccagcagtggctatggtacagattttgtttttacaattgaaaacatgctctca
R  F  S  S  S  G  Y  G  T  D  F  V  F  T  I  E  N  M  L  S
                              CDR3
        250       260       270       280       290       300
gaagatgttgcagattactactgtttgcaaagtgataacttgctcacgttcggtgctggc
E  D  V  A  D  Y  Y  C  L  Q  S  D  N  L  L  T  F  G  A  G

        310       320       330
accaagctggaaatcaaacggatggtc
T  K  L  E  I  K  R  M  V
```

Fig.13

```
       10        20        30        40        50        60
caggtgcagctgcaggagtctgggggaggcttagtgcagcctggagggtcccggaaactc
Q  V  Q  L  Q  E  S  G  G  G  L  V  Q  P  G  G  S  R  K  L

                  CDR1
       70        80        90       100       110       120
tcctgtgcagcctctggattcactttcagtagctttggaatgcactgggttcgtcaggct
S  C  A  A  S  G  F  T  F  S  S  F  G  M  H  W  V  R  Q  A

                                          CDR2
      130       140       150       160       170       180
ccagagaaggggctggagtgggtcgcatacattagtagtggcagtagtaccatctactat
P  E  K  G  L  E  W  V  A  Y  I  S  S  G  S  S  T  I  Y  Y

      190       200       210       220       230       240
gcagacacagtgaagggccgattcaccatctccagagacaatcccaagaacaccctgttc
A  D  T  V  K  G  R  F  T  I  S  R  D  N  P  K  N  T  L  F

                                                    CDR3
      250       260       270       280       290       300
ctgcaaatgaccagtctaaggtctgaggacacggccatgtattactgtgcaagatggaag
L  Q  M  T  S  L  R  S  E  D  T  A  M  Y  Y  C  A  R  W  K

      310       320       330       340
ggggactggggccaagggaccacggtcaccgtctcctca
G  D  W  G  Q  G  T  T  V  T  V  S  S
```

Fig. 14

```
       10        20        30        40        50        60
gacatccagatgacgcagtctccatcctccctggctgtgacagcaggagagaaggtcact
D  I  Q  M  T  Q  S  P  S  S  L  A  V  T  A  G  E  K  V  T
                                 CDR1
       70        80        90       100       110       120
atgagctgcaagtccagtcagagtctgttaaacagtggaaatcaaaagaactacttgacc
M  S  C  K  S  S  Q  S  L  L  N  S  G  N  Q  K  N  Y  L  T
                                                      CDR2
      130       140       150       160       170       180
tggtaccagcagaaaccagggcagcctcctaaactgttgatctactgggcatccactagg
W  Y  Q  Q  K  P  G  Q  P  P  K  L  L  I  Y  W  A  S  T  R

      190       200       210       220       230       240
gaatctggggtccctgatcgcttcacaggcagtggatctggaacagatttcactctcacc
E  S  G  V  P  D  R  F  T  G  S  G  S  G  T  D  F  T  L  T
                                                      CDR3
      250       260       270       280       290       300
atcagcagtgtgcaggctgaagacctggcagtttattactgtcagaatgattatagttat
I  S  S  V  Q  A  E  D  L  A  V  Y  Y  C  Q  N  D  Y  S  Y

      310       320       330       340
ccattcacgttcggctcggggaccaagctggagatggtc
P  F  T  F  G  S  G  T  K  L  E  M  V
```

Fig.15

```
        10        20        30        40        50        60
caggtcaaactgcagcagtcaggccctgggatattgcagtcctcccagaccctcagtctg
Q  V  K  L  Q  Q  S  G  P  G  I  L  Q  S  S  Q  T  L  S  L
                                  CDR1
        70        80        90       100       110       120
acttgttctttctctgggttttcactgagcacttctggtttgggtgtgagctggattcgt
T  C  S  F  S  G  F  S  L  S  T  S  G  L  G  V  S  W  I  R
                                                    CDR2
       130       140       150       160       170       180
cagccttcaggaaagggtctggagtggctggcacacatttactgggatgatgacaagcgc
Q  P  S  G  K  G  L  E  W  L  A  H  I  Y  W  D  D  D  K  R

       190       200       210       220       230       240
tataacccatccctgaagagccggctcacaatctccaaggatacctccagaaaccaggta
Y  N  P  S  L  K  S  R  L  T  I  S  K  D  T  S  R  N  Q  V

       250       260       270       280       290       300
ttcctcaggatcaccagtgtggacactgcagatactgccacatactactgtgcccttaat
F  L  R  I  T  S  V  D  T  A  D  T  A  T  Y  Y  C  A  L  N
      CDR3
       310       320       330       340       350       360
tactacggtaataacttctacgctatggactactggggccaagggaccacggtcaccgtc
Y  Y  G  N  N  F  Y  A  M  D  Y  W  G  Q  G  T  T  V  T  V

       370
tcctcg
S  S
```

Fig.16

```
         10        20        30        40        50        60
gacatccagatgacacagtctccatcatctctggctgtgtctgcaggagagaaaggtcact
D  I  Q  M  T  Q  S  P  S  S  L  A  V  S  A  G  E  K  V  T
                                 CDR1
         70        80        90       100       110       120
atgagctgtaagtccagtcaaagtgttttatacagttcaaatcagaagaactacttggcc
M  S  C  K  S  S  Q  S  V  L  Y  S  S  N  Q  K  N  Y  L  A
                                                      CDR2
        130       140       150       160       170       180
tggtaccagcagaaaccagggcagtctcctaaactgctgatcttctgggcttccactagg
W  Y  Q  Q  K  P  G  Q  S  P  K  L  L  I  F  W  A  S  T  R

        190       200       210       220       230       240
gaatctggtgtccctgatcggttcacaggcagtggatctgggacagattttactcttacc
E  S  G  V  P  D  R  F  T  G  S  G  S  G  T  D  F  T  L  T
                                                      CDR3
        250       260       270       280       290       300
atcagcagtgtacaagctgaagacctggcagtttattactgtcatcaatacctctcctcg
I  S  S  V  Q  A  E  D  L  A  V  Y  Y  C  H  Q  Y  L  S  S

        310       320       330       340       350
ccacgtacgttcggtgctggcaccaagctggaaatcaaacgg
P  R  T  F  G  A  G  T  K  L  E  I  K  R
```

Fig.17
(A)
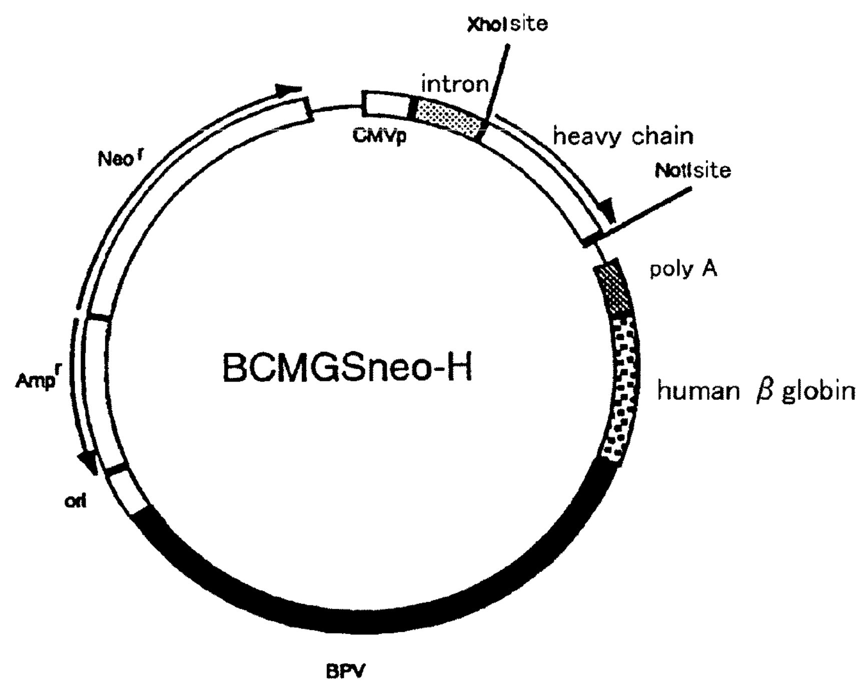
(B)
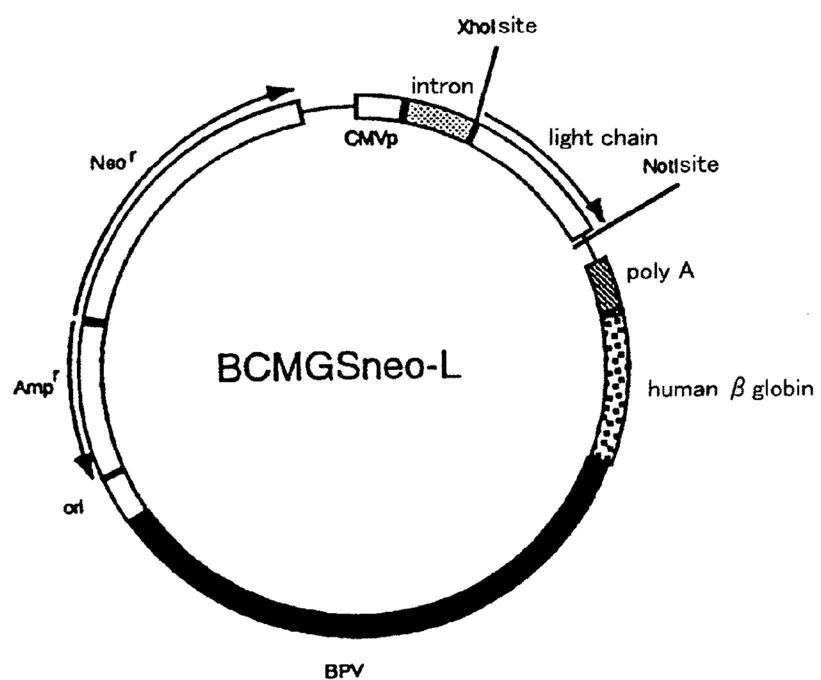

```
                              SEQUENCE LISTING

<160> NUMBER OF SEQ ID NOS: 101

<210> SEQ ID NO 1
<211> LENGTH: 121
<212> TYPE: PRT
<213> ORGANISM: Mus musculus

<400> SEQUENCE: 1

Gln Val Gln Leu Gln Gln Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Val Ile Asn Pro Tyr Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Glu Gly Tyr Gly Ser Ser Tyr Arg Ala Met Asp Tyr Trp Gly
            100                 105                 110

Gln Gly Thr Thr Val Thr Val Ser Ser
        115                 120


<210> SEQ ID NO 2
<211> LENGTH: 10
<212> TYPE: PRT
<213> ORGANISM: Mus musculus

<400> SEQUENCE: 2

Gly Tyr Thr Phe Thr Asp Tyr Tyr Met Asn
1               5                   10


<210> SEQ ID NO 3
<211> LENGTH: 17
<212> TYPE: PRT
<213> ORGANISM: Mus musculus

<400> SEQUENCE: 3
```

```
Val Ile Asn Pro Tyr Asn Gly Gly Thr Ser Tyr Asn Gln Lys Phe Lys
1               5                   10                  15

Gly


<210> SEQ ID NO 4
<211> LENGTH: 11
<212> TYPE: PRT
<213> ORGANISM: Mus musculus

<400> SEQUENCE: 4

Gly Tyr Gly Ser Ser Tyr Arg Ala Met Asp Tyr
1               5                   10


<210> SEQ ID NO 5
<211> LENGTH: 109
<212> TYPE: PRT
<213> ORGANISM: Mus musculus

<400> SEQUENCE: 5

Asp Ile Glu Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Arg Thr Phe Gly Gly Gly Thr Lys Leu Glu Ile Lys Arg
            100                 105


<210> SEQ ID NO 6
<211> LENGTH: 12
<212> TYPE: PRT
<213> ORGANISM: Mus musculus

<400> SEQUENCE: 6

Thr Ala Ser Ser Ser Val Ser Ser Ser Tyr Leu His
1               5                   10


<210> SEQ ID NO 7
<211> LENGTH: 7
<212> TYPE: PRT
<213> ORGANISM: Mus musculus

<400> SEQUENCE: 7

Ser Thr Ser Asn Leu Ala Ser
1               5


<210> SEQ ID NO 8
<211> LENGTH: 9
<212> TYPE: PRT
<213> ORGANISM: Mus musculus

<400> SEQUENCE: 8

His Gln Tyr His Arg Ser Pro Arg Thr
1               5
```

<210> SEQ ID NO 9
<211> LENGTH: 115
<212> TYPE: PRT
<213> ORGANISM: Mus musculus

<400> SEQUENCE: 9

```
Gln Val Gln Leu Gln Gln Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Arg Val Ala Tyr Trp Gly Gln Gly Thr Thr Val Thr
            100                 105                 110

Val Ser Ser
        115
```

<210> SEQ ID NO 10
<211> LENGTH: 10
<212> TYPE: PRT
<213> ORGANISM: Mus musculus

<400> SEQUENCE: 10

```
Gly Phe Thr Phe Asn Thr Tyr Ala Met Asn
1               5                   10
```

<210> SEQ ID NO 11
<211> LENGTH: 19
<212> TYPE: PRT
<213> ORGANISM: Mus musculus

<400> SEQUENCE: 11

```
Arg Ile Arg Ser Lys Ser Asn Asn Tyr Ala Thr Tyr Tyr Ala Asp Ser
1               5                   10                  15

Val Lys Asp
```

<210> SEQ ID NO 12
<211> LENGTH: 4
<212> TYPE: PRT
<213> ORGANISM: Mus musculus

<400> SEQUENCE: 12

```
Arg Val Ala Tyr
1
```

<210> SEQ ID NO 13
<211> LENGTH: 109
<212> TYPE: PRT
<213> ORGANISM: Mus musculus

<400> SEQUENCE: 13

```
Asp Ile Gln Met Thr Gln Ser Pro Ala Ser Leu Ser Met Ala Ile Gly
1               5                   10                  15

Glu Lys Val Thr Ile Arg Cys Ile Thr Ser Thr Asp Ile Asp Asp Asp
            20                  25                  30
```

-continued

```
Met Asn Trp Tyr Gln Gln Lys Pro Gly Glu Pro Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Leu Thr
                85                  90                  95

Phe Gly Ala Gly Thr Lys Leu Glu Ile Lys Arg Met Val
            100                 105


<210> SEQ ID NO 14
<211> LENGTH: 11
<212> TYPE: PRT
<213> ORGANISM: Mus musculus

<400> SEQUENCE: 14

Ile Thr Ser Thr Asp Ile Asp Asp Asp Met Asn
1               5                   10


<210> SEQ ID NO 15
<211> LENGTH: 7
<212> TYPE: PRT
<213> ORGANISM: Mus musculus

<400> SEQUENCE: 15

Glu Gly Asn Thr Leu Arg Pro
1               5


<210> SEQ ID NO 16
<211> LENGTH: 8
<212> TYPE: PRT
<213> ORGANISM: Mus musculus

<400> SEQUENCE: 16

Leu Gln Ser Asp Asn Leu Leu Thr
1               5


<210> SEQ ID NO 17
<211> LENGTH: 113
<212> TYPE: PRT
<213> ORGANISM: Mus musculus

<400> SEQUENCE: 17

Gln Val Gln Leu Gln Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Trp Lys Gly Asp Trp Gly Gln Gly Thr Thr Val Thr Val Ser
            100                 105                 110

Ser
```

<210> SEQ ID NO 18
<211> LENGTH: 11
<212> TYPE: PRT
<213> ORGANISM: Mus musculus

<400> SEQUENCE: 18

```
Ser Gly Phe Thr Phe Ser Ser Phe Gly Met His
1               5                   10
```

<210> SEQ ID NO 19
<211> LENGTH: 17
<212> TYPE: PRT
<213> ORGANISM: Mus musculus

<400> SEQUENCE: 19

```
Tyr Ile Ser Ser Gly Ser Ser Thr Ile Tyr Tyr Ala Asp Thr Val Lys
1               5                   10                  15

Gly
```

<210> SEQ ID NO 20
<211> LENGTH: 4
<212> TYPE: PRT
<213> ORGANISM: Mus musculus

<400> SEQUENCE: 20

```
Trp Lys Gly Asp
1
```

<210> SEQ ID NO 21
<211> LENGTH: 113
<212> TYPE: PRT
<213> ORGANISM: Mus musculus

<400> SEQUENCE: 21

```
Asp Ile Gln Met Thr Gln Ser Pro Ser Ser Leu Ala Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly Ser Gly Thr Lys Leu Glu Met
            100                 105                 110

Val
```

<210> SEQ ID NO 22
<211> LENGTH: 17
<212> TYPE: PRT
<213> ORGANISM: Mus musculus

<400> SEQUENCE: 22

```
Lys Ser Ser Gln Ser Leu Leu Asn Ser Gly Asn Gln Lys Asn Tyr Leu
1               5                   10                  15

Thr
```

```
<210> SEQ ID NO 23
<211> LENGTH: 7
<212> TYPE: PRT
<213> ORGANISM: Mus musculus

<400> SEQUENCE: 23

Trp Ala Ser Thr Arg Glu Ser
1               5


<210> SEQ ID NO 24
<211> LENGTH: 9
<212> TYPE: PRT
<213> ORGANISM: Mus musculus

<400> SEQUENCE: 24

Gln Asn Asp Tyr Ser Tyr Pro Phe Thr
1               5


<210> SEQ ID NO 25
<211> LENGTH: 122
<212> TYPE: PRT
<213> ORGANISM: Mus musculus

<400> SEQUENCE: 25

Gln Val Lys Leu Gln Gln Ser Gly Pro Gly Ile Leu Gln Ser Ser Gln
1               5                   10                  15

Thr Leu Ser Leu Thr Cys Ser Phe Ser Gly Phe Ser Leu Ser Thr Ser
            20                  25                  30

Gly Leu Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Phe Leu Arg Ile Thr Ser Val Asp Thr Ala Asp Thr Ala Thr Tyr Tyr
                85                  90                  95

Cys Ala Leu Asn Tyr Tyr Gly Asn Asn Phe Tyr Ala Met Asp Tyr Trp
            100                 105                 110

Gly Gln Gly Thr Thr Val Thr Val Ser Ser
        115                 120


<210> SEQ ID NO 26
<211> LENGTH: 12
<212> TYPE: PRT
<213> ORGANISM: Mus musculus

<400> SEQUENCE: 26

Gly Phe Ser Leu Ser Thr Ser Gly Leu Gly Val Ser
1               5                   10


<210> SEQ ID NO 27
<211> LENGTH: 16
<212> TYPE: PRT
<213> ORGANISM: Mus musculus

<400> SEQUENCE: 27

His Ile Tyr Trp Asp Asp Asp Lys Arg Tyr Asn Pro Ser Leu Lys Ser
1               5                   10                  15


<210> SEQ ID NO 28
```

<211> LENGTH: 12
<212> TYPE: PRT
<213> ORGANISM: Mus musculus

<400> SEQUENCE: 28

Asn Tyr Tyr Gly Asn Asn Phe Tyr Ala Met Asp Tyr
1 5 10

<210> SEQ ID NO 29
<211> LENGTH: 114
<212> TYPE: PRT
<213> ORGANISM: Mus musculus

<400> SEQUENCE: 29

Asp Ile Gln Met Thr Gln Ser Pro Ser Ser Leu Ala Val Ser Ala Gly
1 5 10 15

Glu Lys Val Thr Met Ser Cys Lys Ser Ser Gln Ser Val Leu Tyr Ser
20 25 30

Ser Asn Gln Lys Asn Tyr Leu Ala Trp Tyr Gln Gln Lys Pro Gly Gln
35 40 45

Ser Pro Lys Leu Leu Ile Phe Trp Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Gln Ala Glu Asp Leu Ala Val Tyr Tyr Cys His Gln
85 90 95

Tyr Leu Ser Ser Pro Arg Thr Phe Gly Ala Gly Thr Lys Leu Glu Ile
100 105 110

Lys Arg

<210> SEQ ID NO 30
<211> LENGTH: 17
<212> TYPE: PRT
<213> ORGANISM: Mus musculus

<400> SEQUENCE: 30

Lys Ser Ser Gln Ser Val Leu Tyr Ser Ser Asn Gln Lys Asn Tyr Leu
1 5 10 15

Ala

<210> SEQ ID NO 31
<211> LENGTH: 7
<212> TYPE: PRT
<213> ORGANISM: Mus musculus

<400> SEQUENCE: 31

Trp Ala Ser Thr Arg Glu Ser
1 5

<210> SEQ ID NO 32
<211> LENGTH: 9
<212> TYPE: PRT
<213> ORGANISM: Mus musculus

<400> SEQUENCE: 32

His Gln Tyr Leu Ser Ser Pro Arg Thr
1 5

<210> SEQ ID NO 33
<211> LENGTH: 363
<212> TYPE: DNA

<213> ORGANISM: Mus musculus

<400> SEQUENCE: 33
caggtgcaac tgcagcagtc tggacctgtg ctggtgaagc ctggggcttc agtgaagatg 60
tcctgtaagg cttctggata cacattcact gactactata tgaactgggt gaagcagagc 120
catggaaaga gccttgagtg gattggagtt attaatcctt acaacggtgg tactagctac 180
aaccagaagt tcaagggcaa ggccacattg actgttgaca agtcctccag cacagcctac 240
atggagctca acagcctgac atctgaggac tctgcagtct attactgtgc aagagagggc 300
tacggtagta gctacagggc tatggactac tggggccaag ggaccacggt caccgtctcc 360
tca 363

<210> SEQ ID NO 34
<211> LENGTH: 30
<212> TYPE: DNA
<213> ORGANISM: Mus musculus

<400> SEQUENCE: 34
ggatacacat tcactgacta ctatatgaac 30

<210> SEQ ID NO 35
<211> LENGTH: 51
<212> TYPE: DNA
<213> ORGANISM: Mus musculus

<400> SEQUENCE: 35
gttattaatc cttacaacgg tggtactagc tacaaccaga agttcaaggg c 51

<210> SEQ ID NO 36
<211> LENGTH: 33
<212> TYPE: DNA
<213> ORGANISM: Mus musculus

<400> SEQUENCE: 36
ggctacggta gtagctacag ggctatggac tac 33

<210> SEQ ID NO 37
<211> LENGTH: 327
<212> TYPE: DNA
<213> ORGANISM: Mus musculus

<400> SEQUENCE: 37
gacatcgagc tcactcagtc tccagcaatc atgtctgcat ctctagggga acgggtcacc 60
atgacctgca ctgccagctc aagtgtaagt tccagttact tgcactggta ccagcagaag 120
ccaggatcct cccccaaact ctggatttat agcacatcca acctggcttc tggagtccca 180
gctcgcttca gtggcagtgg gtctgggacc tcttactctc tcacaatcag cagcatggag 240
gctgaagatg ctgccactta ttactgccac cagtatcatc gttccccacg gacgttcggt 300
ggaggcacca agctggaaat caaacgg 327

<210> SEQ ID NO 38
<211> LENGTH: 36
<212> TYPE: DNA
<213> ORGANISM: Mus musculus

<400> SEQUENCE: 38
actgccagct caagtgtaag ttccagttac ttgcac 36

<210> SEQ ID NO 39
<211> LENGTH: 21
<212> TYPE: DNA
<213> ORGANISM: Mus musculus

<400> SEQUENCE: 39
agcacatcca acctggcttc t 21

<210> SEQ ID NO 40
<211> LENGTH: 27
<212> TYPE: DNA
<213> ORGANISM: Mus musculus

<400> SEQUENCE: 40
caccagtatc atcgttcccc acggacg 27

<210> SEQ ID NO 41
<211> LENGTH: 345
<212> TYPE: DNA
<213> ORGANISM: Mus musculus

<400> SEQUENCE: 41
caggtccaac tgcagcagtc aggtggagga ttggtgcagc ctaaagggtc attgaaactc 60
tcatgtgcag cctctggatt caccttcaat acctacgcca tgaactgggt ccgccaggct 120
ccaggaaagg gtttggaatg ggttgctcgc ataagaagta aaagtaataa ttatgcaaca 180
tattatgccg attcagtgaa agacaggttc accatctcca gagatgattc acaaagcatg 240
ctctatctgc aaatgaacaa cttgaaaact gaggacacag ccatgtatta ctgtgtgaga 300
cgggttgctt actggggcca agggaccacg gtcaccgtct cctca 345

<210> SEQ ID NO 42
<211> LENGTH: 30
<212> TYPE: DNA
<213> ORGANISM: Mus musculus

<400> SEQUENCE: 42
ggattcacct tcaataccta cgccatgaac 30

<210> SEQ ID NO 43
<211> LENGTH: 57
<212> TYPE: DNA
<213> ORGANISM: Mus musculus

<400> SEQUENCE: 43
cgcataagaa gtaaaagtaa taattatgca acatattatg ccgattcagt gaaagac 57

<210> SEQ ID NO 44
<211> LENGTH: 12
<212> TYPE: DNA
<213> ORGANISM: Mus musculus

<400> SEQUENCE: 44
cgggttgctt ac 12

<210> SEQ ID NO 45
<211> LENGTH: 327
<212> TYPE: DNA
<213> ORGANISM: Mus musculus

<400> SEQUENCE: 45
gacatccaga tgacacagtc tccagcatcc ctgtccatgg ctataggaga aaaagtcacc 60

-continued

```
atcagatgca taaccagcac tgatattgat gatgatatga actggtacca gcagaagcca    120

ggggaacctc ctaagctcct tatttcagaa ggcaatactc ttcgtcctgg agtcccatcc    180

cgattctcca gcagtggcta tggtacagat tttgttttta caattgaaaa catgctctca    240

gaagatgttg cagattacta ctgtttgcaa agtgataact tgctcacgtt cggtgctggc    300

accaagctgg aaatcaaacg gatggtc                                         327


<210> SEQ ID NO 46
<211> LENGTH: 33
<212> TYPE: DNA
<213> ORGANISM: Mus musculus

<400> SEQUENCE: 46

ataaccagca ctgatattga tgatgatatg aac                                   33


<210> SEQ ID NO 47
<211> LENGTH: 21
<212> TYPE: DNA
<213> ORGANISM: Mus musculus

<400> SEQUENCE: 47

gaaggcaata ctcttcgtcc t                                                21


<210> SEQ ID NO 48
<211> LENGTH: 24
<212> TYPE: DNA
<213> ORGANISM: Mus musculus

<400> SEQUENCE: 48

ttgcaaagtg ataacttgct cacg                                             24


<210> SEQ ID NO 49
<211> LENGTH: 339
<212> TYPE: DNA
<213> ORGANISM: Mus musculus

<400> SEQUENCE: 49

caggtgcagc tgcaggagtc tgggggaggc ttagtgcagc ctggagggtc ccggaaactc     60

tcctgtgcag cctctggatt cactttcagt agctttggaa tgcactgggt tcgtcaggct    120

ccagagaagg ggctggagtg ggtcgcatac attagtagtg gcagtagtac catctactat    180

gcagacacag tgaagggccg attcaccatc tccagagaca atcccaagaa caccctgttc    240

ctgcaaatga ccagtctaag gtctgaggac acggccatgt attactgtgc aagatggaag    300

ggggactggg gccaagggac cacggtcacc gtctcctca                            339


<210> SEQ ID NO 50
<211> LENGTH: 33
<212> TYPE: DNA
<213> ORGANISM: Mus musculus

<400> SEQUENCE: 50

tctggattca ctttcagtag ctttggaatg cac                                   33


<210> SEQ ID NO 51
<211> LENGTH: 51
<212> TYPE: DNA
<213> ORGANISM: Mus musculus

<400> SEQUENCE: 51

tacattagta gtggcagtag taccatctac tatgcagaca cagtgaaggg c               51
```

<210> SEQ ID NO 52
<211> LENGTH: 12
<212> TYPE: DNA
<213> ORGANISM: Mus musculus

<400> SEQUENCE: 52
tggaaggggg ac 12

<210> SEQ ID NO 53
<211> LENGTH: 339
<212> TYPE: DNA
<213> ORGANISM: Mus musculus

<400> SEQUENCE: 53
gacatccaga tgacgcagtc tccatcctcc ctggctgtga cagcaggaga gaaggtcact 60
atgagctgca agtccagtca gagtctgtta aacagtggaa atcaaaagaa ctacttgacc 120
tggtaccagc agaaaccagg gcagcctcct aaactgttga tctactgggc atccactagg 180
gaatctgggg tccctgatcg cttcacaggc agtggatctg gaacagattt cactctcacc 240
atcagcagtg tgcaggctga agacctggca gtttattact gtcagaatga ttatagttat 300
ccattcacgt tcggctcggg gaccaagctg gagatggtc 339

<210> SEQ ID NO 54
<211> LENGTH: 51
<212> TYPE: DNA
<213> ORGANISM: Mus musculus

<400> SEQUENCE: 54
aagtccagtc agagtctgtt aaacagtgga aatcaaaaga actacttgac c 51

<210> SEQ ID NO 55
<211> LENGTH: 21
<212> TYPE: DNA
<213> ORGANISM: Mus musculus

<400> SEQUENCE: 55
tgggcatcca ctagggaatc t 21

<210> SEQ ID NO 56
<211> LENGTH: 27
<212> TYPE: DNA
<213> ORGANISM: Mus musculus

<400> SEQUENCE: 56
cagaatgatt atagttatcc attcacg 27

<210> SEQ ID NO 57
<211> LENGTH: 366
<212> TYPE: DNA
<213> ORGANISM: Mus musculus

<400> SEQUENCE: 57
caggtcaaac tgcagcagtc aggccctggg atattgcagt cctcccagac cctcagtctg 60
acttgttctt tctctgggtt ttcactgagc acttctggtt tgggtgtgag ctggattcgt 120
cagccttcag gaaagggtct ggagtggctg gcacacattt actgggatga tgacaagcgc 180
tataacccat ccctgaagag ccggctcaca atctccaagg atacctccag aaaccaggta 240
ttcctcagga tcaccagtgt ggacactgca gatactgcca catactactg tgcccttaat 300

-continued

```
tactacggta ataacttcta cgctatggac tactggggcc aagggaccac ggtcaccgtc    360

tcctcg                                                               366


<210> SEQ ID NO 58
<211> LENGTH: 36
<212> TYPE: DNA
<213> ORGANISM: Mus musculus

<400> SEQUENCE: 58

gggttttcac tgagcacttc tggtttgggt gtgagc                               36


<210> SEQ ID NO 59
<211> LENGTH: 48
<212> TYPE: DNA
<213> ORGANISM: Mus musculus

<400> SEQUENCE: 59

cacatttact gggatgatga caagcgctat aacccatccc tgaagagc                  48


<210> SEQ ID NO 60
<211> LENGTH: 36
<212> TYPE: DNA
<213> ORGANISM: Mus musculus

<400> SEQUENCE: 60

aattactacg gtaataactt ctacgctatg gactac                               36


<210> SEQ ID NO 61
<211> LENGTH: 342
<212> TYPE: DNA
<213> ORGANISM: Mus musculus

<400> SEQUENCE: 61

gacatccaga tgacacagtc tccatcatct ctggctgtgt ctgcaggaga aaaggtcact     60

atgagctgta agtccagtca aagtgtttta tacagttcaa atcagaagaa ctacttggcc    120

tggtaccagc agaaaccagg gcagtctcct aaactgctga tcttctgggc ttccactagg    180

gaatctggtg tccctgatcg gttcacaggc agtggatctg ggacagattt tactcttacc    240

atcagcagtg tacaagctga agacctggca gtttattact gtcatcaata cctctcctcg    300

ccacgtacgt tcggtgctgg caccaagctg gaaatcaaac gg                       342


<210> SEQ ID NO 62
<211> LENGTH: 51
<212> TYPE: DNA
<213> ORGANISM: Mus musculus

<400> SEQUENCE: 62

aagtccagtc aaagtgtttt atacagttca aatcagaaga actacttggc c              51


<210> SEQ ID NO 63
<211> LENGTH: 21
<212> TYPE: DNA
<213> ORGANISM: Mus musculus

<400> SEQUENCE: 63

tgggcttcca ctagggaatc t                                               21


<210> SEQ ID NO 64
<211> LENGTH: 27
<212> TYPE: DNA
<213> ORGANISM: Mus musculus
```

<400> SEQUENCE: 64
catcaatacc tctcctcgcc acgtacg 27

<210> SEQ ID NO 65
<211> LENGTH: 52
<212> TYPE: DNA
<213> ORGANISM: Artificial
<220> FEATURE:
<223> OTHER INFORMATION: PCR primer

<400> SEQUENCE: 65
acttactcgc ggcccagccg gccatggccg akgtgcagct tcaggagtca gg 52

<210> SEQ ID NO 66
<211> LENGTH: 52
<212> TYPE: DNA
<213> ORGANISM: Artificial
<220> FEATURE:
<223> OTHER INFORMATION: PCR primer

<400> SEQUENCE: 66
acttactcgc ggcccagccg gccatggccc aggtgcagct gaaggagtca gg 52

<210> SEQ ID NO 67
<211> LENGTH: 52
<212> TYPE: DNA
<213> ORGANISM: Artificial
<220> FEATURE:
<223> OTHER INFORMATION: PCR primer

<400> SEQUENCE: 67
acttactcgc ggcccagccg gccatggccc aggtgcagct gaagcagtca gg 52

<210> SEQ ID NO 68
<211> LENGTH: 52
<212> TYPE: DNA
<213> ORGANISM: Artificial
<220> FEATURE:
<223> OTHER INFORMATION: PCR primer

<400> SEQUENCE: 68
acttactcgc ggcccagccg gccatggccg aggtccagct gcarcartct gg 52

<210> SEQ ID NO 69
<211> LENGTH: 52
<212> TYPE: DNA
<213> ORGANISM: Artificial
<220> FEATURE:
<223> OTHER INFORMATION: PCR primer

<400> SEQUENCE: 69
acttactcgc ggcccagccg gccatggccg aggttcagct gcagcagtct gg 52

<210> SEQ ID NO 70
<211> LENGTH: 52
<212> TYPE: DNA
<213> ORGANISM: Artificial
<220> FEATURE:
<223> OTHER INFORMATION: PCR primer

<400> SEQUENCE: 70
acttactcgc ggcccagccg gccatggccc aggtccaact gcagcagcct gg 52

<210> SEQ ID NO 71

-continued

<211> LENGTH: 52
<212> TYPE: DNA
<213> ORGANISM: Artificial
<220> FEATURE:
<223> OTHER INFORMATION: PCR primer

<400> SEQUENCE: 71
acttactcgc ggcccagccg gccatggccc aggtccacct gcagcagtct gg 52

<210> SEQ ID NO 72
<211> LENGTH: 52
<212> TYPE: DNA
<213> ORGANISM: Artificial
<220> FEATURE:
<223> OTHER INFORMATION: PCR primer

<400> SEQUENCE: 72
acttactcgc ggcccagccg gccatggccg aggtgaagct ggtggartct gg 52

<210> SEQ ID NO 73
<211> LENGTH: 52
<212> TYPE: DNA
<213> ORGANISM: Artificial
<220> FEATURE:
<223> OTHER INFORMATION: PCR primer

<400> SEQUENCE: 73
acttactcgc ggcccagccg gccatggccg aggtgaagct tctggagtct gg 52

<210> SEQ ID NO 74
<211> LENGTH: 52
<212> TYPE: DNA
<213> ORGANISM: Artificial
<220> FEATURE:
<223> OTHER INFORMATION: PCR primer

<400> SEQUENCE: 74
acttactcgc ggcccagccg gccatggccg aagtgaagct tgaggagtct gg 52

<210> SEQ ID NO 75
<211> LENGTH: 52
<212> TYPE: DNA
<213> ORGANISM: Artificial
<220> FEATURE:
<223> OTHER INFORMATION: PCR primer

<400> SEQUENCE: 75
acttactcgc ggcccagccg gccatggccg aggtgaagct ggatgagact gg 52

<210> SEQ ID NO 76
<211> LENGTH: 52
<212> TYPE: DNA
<213> ORGANISM: Artificial
<220> FEATURE:
<223> OTHER INFORMATION: PCR primer

<400> SEQUENCE: 76
acttactcgc ggcccagccg gccatggccg aagtgaagct ggtggagtct ga 52

<210> SEQ ID NO 77
<211> LENGTH: 52
<212> TYPE: DNA
<213> ORGANISM: Artificial
<220> FEATURE:
<223> OTHER INFORMATION: PCR primer

<400> SEQUENCE: 77
acttactcgc ggcccagccg gccatggccg aagtgcagct ggtggagtct gg 52

<210> SEQ ID NO 78
<211> LENGTH: 52
<212> TYPE: DNA
<213> ORGANISM: Artificial
<220> FEATURE:
<223> OTHER INFORMATION: PCR primer

<400> SEQUENCE: 78
acttactcgc ggcccagccg gccatggccg aagtgatgct ggtggagtct gg 52

<210> SEQ ID NO 79
<211> LENGTH: 52
<212> TYPE: DNA
<213> ORGANISM: Artificial
<220> FEATURE:
<223> OTHER INFORMATION: PCR primer

<400> SEQUENCE: 79
acttactcgc ggcccagccg gccatggccg aagtgaagct ggtggagtct gg 52

<210> SEQ ID NO 80
<211> LENGTH: 52
<212> TYPE: DNA
<213> ORGANISM: Artificial
<220> FEATURE:
<223> OTHER INFORMATION: PCR primer

<400> SEQUENCE: 80
acttactcgc ggcccagccg gccatggccg aggttcagct tcagcagtct gg 52

<210> SEQ ID NO 81
<211> LENGTH: 52
<212> TYPE: DNA
<213> ORGANISM: Artificial
<220> FEATURE:
<223> OTHER INFORMATION: PCR primer

<400> SEQUENCE: 81
acttactcgc ggcccagccg gccatggccc aggtccagct gcagcagtct gg 52

<210> SEQ ID NO 82
<211> LENGTH: 37
<212> TYPE: DNA
<213> ORGANISM: Artificial
<220> FEATURE:
<223> OTHER INFORMATION: PCR primer

<400> SEQUENCE: 82
cgttttggcg ctcgagacgg tgaccgtggt ccctgcg 37

<210> SEQ ID NO 83
<211> LENGTH: 37
<212> TYPE: DNA
<213> ORGANISM: Artificial
<220> FEATURE:
<223> OTHER INFORMATION: PCR primer

<400> SEQUENCE: 83
cgttttggcg ctcgagactg tgagagtggt gccttgg 37

<210> SEQ ID NO 84
<211> LENGTH: 37
<212> TYPE: DNA

<213> ORGANISM: Artificial
<220> FEATURE:
<223> OTHER INFORMATION: PCR primer

<400> SEQUENCE: 84
cgttttggcg ctcgagacag tgaccagagt cccttgg 37

<210> SEQ ID NO 85
<211> LENGTH: 37
<212> TYPE: DNA
<213> ORGANISM: Artificial
<220> FEATURE:
<223> OTHER INFORMATION: PCR primer

<400> SEQUENCE: 85
cgttttggcg ctcgagacgg tgactgaggt tccttga 37

<210> SEQ ID NO 86
<211> LENGTH: 363
<212> TYPE: DNA
<213> ORGANISM: Mus musculus

<400> SEQUENCE: 86
caggtgcaac tgcagcagtc tggacctgtg ctggtgaagc ctggggcttc agtgaagatg 60
tcctgtaagg cttctggata cacattcact gactactata tgaactgggt gaagcagagc 120
catggaaaga gccttgagtg gattggagtt attaatcctt acaacggtgg tactagctac 180
aaccagaagt tcaagggcaa ggccacattg actgttgaca agtcctccag cacagcctac 240
atggagctca acagcctgac atctgaggac tctgcagtct attactgtgc aagagagggc 300
tacggtagta gctacagggc tatggactac tggggccaag ggaccacggt caccgtctcc 360
tca 363

<210> SEQ ID NO 87
<211> LENGTH: 121
<212> TYPE: PRT
<213> ORGANISM: Mus musculus

<400> SEQUENCE: 87

Gln Val Gln Leu Gln Gln Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Val Ile Asn Pro Tyr Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Glu Gly Tyr Gly Ser Ser Tyr Arg Ala Met Asp Tyr Trp Gly
            100                 105                 110

Gln Gly Thr Thr Val Thr Val Ser Ser
        115                 120

<210> SEQ ID NO 88
<211> LENGTH: 327
<212> TYPE: DNA
<213> ORGANISM: Mus musculus

<400> SEQUENCE: 88

```
gacatcgagc tcactcagtc tccagcaatc atgtctgcat ctctagggga acgggtcacc     60

atgacctgca ctgccagctc aagtgtaagt tccagttact tgcactggta ccagcagaag    120

ccaggatcct cccccaaact ctggatttat agcacatcca acctggcttc tggagtccca    180

gctcgcttca gtggcagtgg gtctgggacc tcttactctc tcacaatcag cagcatggag    240

gctgaagatg ctgccactta ttactgccac cagtatcatc gttccccacg gacgttcggt    300

ggaggcacca agctggaaat caaacgg                                        327
```

<210> SEQ ID NO 89
<211> LENGTH: 109
<212> TYPE: PRT
<213> ORGANISM: Mus musculus

<400> SEQUENCE: 89

```
Asp Ile Glu Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Arg Thr Phe Gly Gly Gly Thr Lys Leu Glu Ile Lys Arg
            100                 105
```

<210> SEQ ID NO 90
<211> LENGTH: 345
<212> TYPE: DNA
<213> ORGANISM: Mus musculus

<400> SEQUENCE: 90

```
caggtccaac tgcagcagtc aggtggagga ttggtgcagc ctaaagggtc attgaaactc     60

tcatgtgcag cctctggatt caccttcaat acctacgcca tgaactgggt ccgccaggct    120

ccaggaaagg gtttggaatg ggttgctcgc ataagaagta aaagtaataa ttatgcaaca    180

tattatgccg attcagtgaa agacaggttc accatctcca gagatgattc acaaagcatg    240

ctctatctgc aaatgaacaa cttgaaaact gaggacacag ccatgtatta ctgtgtgaga    300

cgggttgctt actggggcca agggaccacg gtcaccgtct cctca                    345
```

<210> SEQ ID NO 91
<211> LENGTH: 115
<212> TYPE: PRT
<213> ORGANISM: Mus musculus

<400> SEQUENCE: 91

```
Gln Val Gln Leu Gln Gln Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
```

-continued

```
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Arg Val Ala Tyr Trp Gly Gln Gly Thr Thr Val Thr
            100                 105                 110

Val Ser Ser
        115


<210> SEQ ID NO 92
<211> LENGTH: 327
<212> TYPE: DNA
<213> ORGANISM: Mus musculus

<400> SEQUENCE: 92

gacatccaga tgacacagtc tccagcatcc ctgtccatgg ctataggaga aaaagtcacc     60

atcagatgca taaccagcac tgatattgat gatgatatga actggtacca gcagaagcca    120

ggggaacctc ctaagctcct tatttcagaa ggcaatactc ttcgtcctgg agtcccatcc    180

cgattctcca gcagtggcta tggtacagat tttgttttta caattgaaaa catgctctca    240

gaagatgttg cagattacta ctgtttgcaa agtgataact tgctcacgtt cggtgctggc    300

accaagctgg aaatcaaacg gatggtc                                         327


<210> SEQ ID NO 93
<211> LENGTH: 109
<212> TYPE: PRT
<213> ORGANISM: Mus musculus

<400> SEQUENCE: 93

Asp Ile Gln Met Thr Gln Ser Pro Ala Ser Leu Ser Met Ala Ile Gly
1               5                   10                  15

Glu Lys Val Thr Ile Arg Cys Ile Thr Ser Thr Asp Ile Asp Asp Asp
            20                  25                  30

Met Asn Trp Tyr Gln Gln Lys Pro Gly Glu Pro Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Leu Thr
                85                  90                  95

Phe Gly Ala Gly Thr Lys Leu Glu Ile Lys Arg Met Val
            100                 105


<210> SEQ ID NO 94
<211> LENGTH: 339
<212> TYPE: DNA
<213> ORGANISM: Mus musculus

<400> SEQUENCE: 94

caggtgcagc tgcaggagtc tgggggaggc ttagtgcagc ctggagggtc ccggaaactc     60

tcctgtgcag cctctggatt cactttcagt agctttggaa tgcactgggt tcgtcaggct    120

ccagagaagg ggctggagtg ggtcgcatac attagtagtg gcagtagtac catctactat    180
```

-continued

```
gcagacacag tgaagggccg attcaccatc tccagagaca atcccaagaa caccctgttc    240

ctgcaaatga ccagtctaag gtctgaggac acggccatgt attactgtgc aagatggaag    300

ggggactggg gccaagggac cacggtcacc gtctcctca                           339


<210> SEQ ID NO 95
<211> LENGTH: 113
<212> TYPE: PRT
<213> ORGANISM: Mus musculus

<400> SEQUENCE: 95

Gln Val Gln Leu Gln Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Trp Lys Gly Asp Trp Gly Gln Gly Thr Thr Val Thr Val Ser
            100                 105                 110

Ser


<210> SEQ ID NO 96
<211> LENGTH: 339
<212> TYPE: DNA
<213> ORGANISM: Mus musculus

<400> SEQUENCE: 96

gacatccaga tgacgcagtc tccatcctcc ctggctgtga cagcaggaga gaaggtcact     60

atgagctgca agtccagtca gagtctgtta aacagtggaa atcaaaagaa ctacttgacc    120

tggtaccagc agaaaccagg gcagcctcct aaactgttga tctactgggc atccactagg    180

gaatctgggg tccctgatcg cttcacaggc agtggatctg gaacagattt cactctcacc    240

atcagcagtg tgcaggctga agacctggca gtttattact gtcagaatga ttatagttat    300

ccattcacgt tcggctcggg gaccaagctg gagatggtc                           339


<210> SEQ ID NO 97
<211> LENGTH: 113
<212> TYPE: PRT
<213> ORGANISM: Mus musculus

<400> SEQUENCE: 97

Asp Ile Gln Met Thr Gln Ser Pro Ser Ser Leu Ala Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
```

-continued

```
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly Ser Gly Thr Lys Leu Glu Met
            100                 105                 110

Val


<210> SEQ ID NO 98
<211> LENGTH: 366
<212> TYPE: DNA
<213> ORGANISM: Mus musculus

<400> SEQUENCE: 98

caggtcaaac tgcagcagtc aggccctggg atattgcagt cctcccagac cctcagtctg      60

acttgttctt tctctgggtt ttcactgagc acttctggtt tgggtgtgag ctggattcgt     120

cagccttcag gaaagggtct ggagtggctg gcacacattt actgggatga tgacaagcgc     180

tataacccat ccctgaagag ccggctcaca atctccaagg atacctccag aaaccaggta     240

ttcctcagga tcaccagtgt ggacactgca gatactgcca catactactg tgcccttaat     300

tactacggta ataacttcta cgctatggac tactggggcc aagggaccac ggtcaccgtc     360

tcctcg                                                                366


<210> SEQ ID NO 99
<211> LENGTH: 122
<212> TYPE: PRT
<213> ORGANISM: Mus musculus

<400> SEQUENCE: 99

Gln Val Lys Leu Gln Gln Ser Gly Pro Gly Ile Leu Gln Ser Ser Gln
1               5                   10                  15

Thr Leu Ser Leu Thr Cys Ser Phe Ser Gly Phe Ser Leu Ser Thr Ser
            20                  25                  30

Gly Leu Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Phe Leu Arg Ile Thr Ser Val Asp Thr Ala Asp Thr Ala Thr Tyr Tyr
                85                  90                  95

Cys Ala Leu Asn Tyr Tyr Gly Asn Asn Phe Tyr Ala Met Asp Tyr Trp
            100                 105                 110

Gly Gln Gly Thr Thr Val Thr Val Ser Ser
        115                 120


<210> SEQ ID NO 100
<211> LENGTH: 342
<212> TYPE: DNA
<213> ORGANISM: Mus musculus

<400> SEQUENCE: 100

gacatccaga tgacacagtc tccatcatct ctggctgtgt ctgcaggaga aaaggtcact      60

atgagctgta agtccagtca aagtgtttta tacagttcaa atcagaagaa ctacttggcc     120

tggtaccagc agaaaccagg gcagtctcct aaactgctga tcttctgggc ttccactagg     180

gaatctggtg tccctgatcg gttcacaggc agtggatctg ggacagattt tactcttacc     240
```

-continued

```
atcagcagtg tacaagctga agacctggca gtttattact gtcatcaata cctctcctcg    300

ccacgtacgt tcggtgctgg caccaagctg gaaatcaaac gg                       342


<210> SEQ ID NO 101
<211> LENGTH: 114
<212> TYPE: PRT
<213> ORGANISM: Mus musculus

<400> SEQUENCE: 101

Asp Ile Gln Met Thr Gln Ser Pro Ser Ser Leu Ala Val Ser Ala Gly
1               5                   10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Phe Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys His Gln
                85                  90                  95

Tyr Leu Ser Ser Pro Arg Thr Phe Gly Ala Gly Thr Lys Leu Glu Ile
            100                 105                 110

Lys Arg
```

ANTIBODY HAVING INHIBITORY EFFECT ON AMYLOID FIBRIL FORMATION

TECHNICAL FIELD

The present invention relates to an antibody having an inhibitory activity on amyloid fibril formation and a production method thereof. More particularly, the present invention relates to an antibody having a high inhibitory activity on amyloid fibril formation, a production method thereof, a CDR (complementarity determining region) for determining a binding property thereof, and nucleic acid encoding the antibody or the CDR. The amyloid fibril formation (aggregation and polymerization of amyloid β protein) is thought to be substantially involved in the onset and progress of Alzheimer's disease. Therefore, the antibody and the like of the present invention can be used for elucidation of prevention, treatment and diagnosis of Alzheimer's disease as well as elucidation of the mechanism of Alzheimer's disease.

BACKGROUND ART

In Japan, the aging of population is now progressing at the highest speed that has never been experienced, and along with this, the number of patients with dementia is increasing. According to a survey conducted by the National Institute of Population and Social Security Research, the number of patients with dementia is estimated to reach 1.65 million by 2000 and 2.64 million by 2015. Since cares for such patients with dementia become much economic burden, there have been demands for development of an effective treatment method as soon as possible.

A major disease of senile dementias is Alzheimer's disease (Aβ). Although the overview of the pathology of this disease is still unknown, studies are rapidly advancing. Features commonly found in patients with Alzheimer's disease are: (1) atrophy of the brain; (2) deposition of plaque-like substances called senile plaques; and (3) neurofibrillary tangle in which fibrillary substances are deposited inside the neurons. When these three features are found, the patient is diagnosed as Alzheimer's disease. A clinical symptom of Alzheimer's disease, i.e., dementia, is closely associated with neuronal loss. As to the reason why the neuronal loss occurs, the above-mentioned pathological changes provide important clues. According to the advancement of studies since the latter half of 1990s, it has been clarified that senile plaques are deposition of aggregated peptides called amyloid β-protein (Aβ). On the other hand, it has been clarified that the neurofibrillary tangle occurs because tau protein, which is one of the scaffold proteins of the neuron, is phosphorylated and aggregated inside the neuron.

Alzheimer's disease is known to occur in two forms, that is, familial Alzheimer's disease caused by genetic factors, and sporadic Alzheimer's disease that is free from genetic reasons. Causative genes or risk factors of familial Alzheimer's disease are becoming clarified. One of the causative genes of familial Alzheimer's disease is a gene encoding Amyloid Precursor Protein (APP). It is known that when this gene contains a mutant, Alzheimer's disease is caused without exception. Therefore, it is thought that if the effect and function of this mutant can be found, the onset mechanism of Alzheimer's disease would be clarified. Since it is expected that familial Alzheimer's disease and sporadic Alzheimer's disease have a common mechanism, it is thought that some of the researches on the onset mechanism of familial Alzheimer's disease may be applied to the cases of sporadic Alzheimer's disease.

Aβ is cleaved from an APP with β- and γ-secretases. It has been reported that Aβ is classified into $Aβ_{40}$ and $Aβ_{42}$ depending on the difference in the cleavage points in which $Aβ_{42}$ is more likely to aggregate than $Aβ_{40}$ and that from the pathological observation, $Aβ_{42}$ firstly aggregates and $Aβ_{40}$ then aggregates around $Aβ_{42}$ as a core to form fibrils. Recent studies by the present inventors provide findings that Aβ starts to be deposited in the Aβ brain via binding to GM1 ganglioside (hereinafter, abbreviated as "GM1") (K. Yanagisawa, A. Odaka, N. Suzuki, Y. Ihara, Nat. Med. 1, 1062 (1995); K. Yanagisawa, Y. Ihara, Neurobiol. Aging 19, S65 (1998)). Furthermore, the present inventors reported that a monoclonal antibody (antibody 4396) that specifically recognizes GM1-bound Aβ was successfully produced (FEBS Letters 420, 43-46 (1997)). Based on the unique molecular characteristics of this GM1-bound Aβ, the present inventors hypothesized that Aβ adopted an altered conformation via binding to GM1 and functioned as a seed of the formation of amyloid fibrils (K. Yanagisawa, A. Odaka, N. Suzuki, Y Ihara, Nat. Med. 1, 1062 (1995)). Subsequently, several investigators performed in vitro studies and their findings support the above-mentioned hypothesis; i.e., Aβ specifically binds to GM1 on the membranes; soluble Aβ starts to aggregate and form amyloid fibrils following the addition of GM1-containing liposomes (J. McLaurin, A. Chakrabartty, J. Biol. Chem. 271, 26482 (1996); P. Choo-Smith, W. K. Surewicz, FEBS Lett. 402, 95 (1997); P. Choo-Smith, W. Garzon-Rodriguez, C. G. Globe, W. K. Sutrewicz, J. Biol. Chem. 272, 22987 (1997); K. Matsuzaki, C. Horikiri, Biochemistry 38, 4137 (1999); V. Koppaka, P. H. Axelsen, Biochemistry 39, 10011 (2000)).

Thereafter, in regard to the molecular mechanism in which GM1-bound Aβ is formed, it has been reported that binding of Aβ to GM1 is dependent on the concentration of cholesterol in the membranes to be bound; i.e., a high concentration of cholesterol enhances the binding of Aβ to GM1 via facilitating the formation of GM1 "cluster" in the membranes (A. Kakio, S. Nishimoto, K. Yanagisawa, Y Kozutumi, K. Matsuzaki, J. Biol. Chem., 276, 24985 (2001)). Furthermore, Aβ may bind to GM1 on synaptic membranes of the aging brain since the cholesterol concentration in the exofacial leaflets of synaptic membranes significantly increases with age and/or with the deficiency in apolipoprotein E (Apo E) (U. Igbavboa, N. A. Avdulov, F. Schroeder, W. G. Wood, J. Neurochem. 66, 1717 (1996); U. Igbavboa, N. A. Avdulov, S. V. Chochina, W. G. Wood, J. Neurochem. 69, 1661 (1997)). While, Aβ may bind to GM1 in GM1-rich and cholesterol-rich membrane domains (referred to as rafts) since the rafts physiologically contain a large amount of Aβ and in the rafts, insoluble Aβ are deposited in a kind of mouse model with familial Alzheimer's disease (R. G Parton, J. Histochem. Cytochem. 42, 155 (1994); K. Simons, E. Ikonen, Nature 387, 569 (1997); S. J. Lee et al., Nat. Med. 4, 730 (1998); M. Morishima-Kawashima, Y. Ihara, Biochemistry 37, 15274 (1998); N. Sawamura et al., J. Biol. Chem. 275, 27901 (2000)).

Thereafter, the present inventors have shown that a seed of the Aβ fibril formation (GAβ complex) in the living body included GM1 by an immunological procedure using an antibody (4396C) and that this antibody recognized a GAβ complex from the Alzheimer's disease brain and suppresses the Aβ polymerization using GAβ complex as a seed. From these results, the present inventors have suggested that, as a core of the amyloid hypothesis describing the onset mechanism of Alzheimer's disease onset, a mechanism of formation of a seed of Aβ fibril formation actually occurs in the living body (WO 03/014162, J. Neurosci., 2004, 24: 4894-4902).

[Patent Document 1] WO 03/014162

[Non Patent Document 1] K. Yanagisawa, A. Odaka, N. Suzuki, Y. Ihara, Nat, Med. 1, 1062 (1995)

[Non Patent Document 2] K. Yanagisawa, Y. Ihara, Neurobiol. Aging 19, S65 (1998)

[Non Patent Document 3] FEBS Letters 420, 43-46 (1997)

[Non Patent Document 4] J. McLaurin, A. Chakrabartty, J. Biol. Chem. 271, 26482 (1996)

[Non Patent Document 5] P. Choo-Smith, W. K. Surewicz, FEBS Lett. 402, 95 (1997)

[Non Patent Document 6] McLaurin J, Chakrabartty A, Eur J. Biochem. 245(2)355 (1997)

[Non Patent Document 7] P. Choo-Smith, W. Garzon-Rodriguez, C. G. Globe, W. K. Sutrewicz, J. Biol. Chem. 272, 22987 (1997)

[Non Patent Document 8] K. Matsuzaki, C. Horikiri, Biochemistry 38, 4137 (1999)

[Non Patent Document 9] V. Koppaka, P. H. Axelsen, Biochemistry 39, 10011 (2000)

[Non Patent Document 10] A. Kakio, S. Nishimoto, K. Yanagisawa, Y. Kozutumi, K. Matsuzaki, J. Biol. Chem., 276, 24985 (2001)

[Non Patent Document 11] U. Igbavboa, N. A. Avdulov, F. Schroeder, W. O. Wood, J. Neurochem. 66, 1717 (1996)

[Non Patent Document 12] U. Igbavboa, N. A. Avdulov, S. V. Chochina, W. G Wood, J. Neurochem. 69, 1661 (1997)

[Non Patent Document 13] R. G Parton, J. Histochem. Cytochem. 42, 155 (1994)

[Non Patent Document 14] K. Simons, E. Ikonen, Nature 387, 569 (1997)

[Non Patent Document 15] S. J. Lee et al., Nat. Med. 4, 730 (1998)

[Non Patent Document 16] M. Morishima-Kawashima, Y. Ihara, Biochemistry 37, 15274 (1998)

[Non Patent Document 17] N. Sawamura et al., J. Biol. Chem. 275, 27901 (2000)

[Non Patent Document 18] J. Neurosci., 2004, 24: 4894-4902

DISCLOSURE OF THE INVENTION

Problem to be Solved by the Invention

In order to develop treatment methods and diagnosis methods targeting Alzheimer's disease, it is necessary to efficiently obtain an antibody effectively inhibiting the amyloid fibril formation (Aβ polymerization), in particular, an antibody specific to a GAβ complex. Conventionally, for treating Alzheimer's disease, "active immunotherapy" such as vaccine therapy, which stimulates and activates the immune system that is present in the body by directly vaccinating or administering a substance causing an immune reaction, and "passive immunotherapy" such as an activation lymphocyte therapy, which activates the lymphocyte responsible for an immune reaction and the like out of the body and returns it in the body, have been considered. However, antibodies exhibiting a sufficient inhibitory activity on the amyloid fibril formation have not been obtained. The present inventors have thought that the reason why an antibody having a high inhibitory activity cannot be obtained is the use of Aβ as an antigen and that when a GAβ complex is used as an antigen instead of Aβ, an antibody having a higher inhibitory activity could be produced. However, because it is difficult to obtain the GAβ complex from the brain with Alzheimer's disease with high purity from the viewpoint of technique and procurement of materials, this approach is not realistic.

By the way, the present inventors have shown that by using a 4396 antibody, the amount of the antigen against which this antibody responds is larger in the brain of an Alzheimer's disease patient and the brain of an aged cynomolgus monkey as compared with that of control and that GM1 and Aβ exist together histologically and physically in the aged cynomolgus monkey brain (International Publication No. 03/014162, J. Neurosci., 2004, 24: 4894-4902). An experiment of reacting GM1-containing liposome and Aβ with each other in vitro has shown that the antigen against which the 4396 antibody, which was obtained from a crude fraction rich in Aβ of the brain of an Alzheimer's disease patient, reacts as an immunogen (FEBS Letters 420, 43-46 (1997)) was GAβ. Some of the conventionally known antibodies recognizing Aβ react with not only Aβ but also GAβ (see, for example, BAN052, J. Neurosci., 2004, 24: 4894-4902). The first antibody, which does not recognize not-polymerized Aβ and the precursor thereof, APP, and which reacts with GAβ, is the 4396 antibody. When the property of this antibody is further examined by a measurement method of Aβ fibril formation by using Thioflavin T in vitro, the inhibitory activity on the fibril formation, which has not been observed in the conventional antibody recognizing Aβ, is shown in a dose-dependent manner. Thus, when GAβ recognized by the 4396 antibody is produced in vitro, a large amount of immunogens having the same property as that of GAβ in the living body and including the well-known composition can be obtained. By selecting an antibody having a property that reacts with GAβ but does not react with the single component (Aβ and GM1) from antibodies obtained by this antigen, it has been expected that an antibody having the same property as that of the 4396 antibody, that is, a property for inhibiting fibril formation of Aβ can be obtained. However, an optimum preparation method of GAβ has not been established.

[Means to Solve the Problems]

Under the above-mentioned circumstances, the present inventors have keenly investigated for the purpose of obtaining an antibody having a high inhibitory activity on amyloid fibril formation (which is also referred to as "Aβ polymerization inhibitory activity"). Firstly, the present inventors have employed a synthetic lipid membrane containing GM1 and Aβ binding thereto as an immunogen for obtaining an antibody having a high Aβ polymerization inhibitory activity. It is thought that an immunogen for obtaining an antibody having a high Aβ polymerization inhibitory activity is required that Aβ be efficiently polymerized with the immunogen as a core, that is, Aβ polymerization initiating activity be high. Therefore, in order to control the amount of formed GAβ and Aβ fibril elongation and to obtain an antibody having an inhibitory activity on Aβ fibril formation more efficiently, it is important to clarify the relation between the change of the composition ratio and the amount of the bound Aβ. Furthermore, a time for reacting GM1-containing liposome and Aβ is thought to be also important. Then, the present inventors have carried out various experiments. As a result of the experiment focusing on the contained amount of GM1 in the synthetic lipid membrane, it has been revealed that the Aβ polymerization initiating activity in the synthetic lipid membrane depends upon the contained amount of GM1. Furthermore, the present inventors have obtained a finding that the time for reacting GM1-containing liposome and Aβ is preferably short. Based on these findings, the present inventors have attempted to produce an antibody using a synthetic lipid membrane containing an appropriate amount of GM1 as an immunogen. When a plurality of the obtained antibodies were examined for the Aβ polymerization inhibitory activity, the Aβ polymerization inhibitory activity shows much higher than that in a general immunization with only Aβ. Furthermore, among the thus obtained antibodies, an antibody having an activity of depolymerizing the once formed Aβ fibrils is also observed. From these results, it has been confirmed that the above-mentioned synthetic lipid membrane is effective as a material for producing an antibody having a high Aβ polymerization inhibitory activity.

On the other hand, the present inventors have succeeded in identifying the amino acid sequences (and the base sequences) of antibodies having a high Aβ polymerization inhibitory activity, determining the sequences of the variable region and specifying the complementarity determining regions (CDRs). The sequence of the variable region, in particular, the sequence information of CDRs is very important information for producing an antibody having a high Aβ polymerization inhibitory activity and the usefulness thereof is high.

Since an antibody obtained by the above-mentioned investigation has a high Aβ polymerization inhibitory activity, the antibodies themselves are useful for developing a treatment method of Alzheimer's disease. Furthermore, the information about CDRs of these antibodies is an essential feature of the antibody having a high Aβ polymerization inhibitory activity. Based on them, it is possible to create and modify the antibody having a high Aβ polymerization inhibitory activity. In particular, it is possible to produce, for example, a human chimeric antibody and a humanized antibody, which have a high Aβ polymerization inhibitory activity.

The present invention is based on the above-mentioned results at least partially and has the following configuration. In other words, the first aspect of the present invention relates to an isolated antibody having an inhibitory activity on amyloid fibril formation. In one embodiment, an inhibitory effect in an amyloid β protein polymerization inhibition test in vitro is 50% or more. Note here that as mentioned below, the inhibitory effect of the subject antibody is calculated in principle by comparing the Aβ polymerization amount after the subject antibody is added and reacted for a predetermined time in an environment in which Aβ polymerization occurs with a GAβ complex as a core or in an environment in which Aβ fibril has been already present, with the Aβ polymerization amount when the subject antibody is not added.

It is preferable that the antibody of the present invention recognizes GM1 ganglioside-bound amyloid O-protein (GAβ complex). With such a characteristic, an antibody capable of effectively inhibiting amyloid fibril formation with a GAβ complex as a core is obtained.

One embodiment of an antibody of the present invention includes a heavy chain variable region having a CDR including an amino acid sequence of any of SEQ ID NOs: 2-4, 10-12, 18-20, and 26-28, or an amino acid sequence that is substantially the same as the amino acid sequence; and a light chain variable region having a CDR including an amino acid sequence of any of SEQ ID NOs: 6-8, 14-16, 22-24, and 30-32, or an amino acid sequence that is substantially the same as the amino acid sequence. These amino acid sequences are derived from the sequences of antibodies that have actually been obtained and identified successfully as antibodies having a high inhibitory activity on amyloid fibril formation.

More specifically, the antibody of the present invention includes a combination of a heavy chain variable region and a light chain variable region selected from the group consisting of the following a to h:

(a) a combination of a heavy chain variable region having a CDR including a heavy chain CDR1 having an amino acid sequence of SEQ ID NO: 2 or an amino acid sequence that is substantially the same as the amino acid sequence, a heavy chain CDR2 having an amino acid sequence of SEQ ID NO: 3 or an amino acid sequence that is substantially the same as the amino acid sequence, and a heavy chain CDR3 having an amino acid sequence of SEQ ID NO: 4 or an amino acid sequence that is substantially the same as the amino acid sequence, and a light chain variable region having a CDR including CDR1 having an amino acid sequence of SEQ ID NO: 6 or an amino acid sequence that is substantially the same as the amino acid sequence, CDR2 having an amino acid sequence of SEQ ID NO: 7 or an amino acid sequence that is substantially the same as the amino acid sequence, and CDR3 having an amino acid sequence of SEQ ID NO: 8 or an amino acid sequence that is substantially the same as the amino acid sequence;

(b) a combination of a heavy chain variable region having a CDR including a heavy chain CDR1 having an amino acid sequence of SEQ ID NO: 10 or an amino acid sequence that is substantially the same as the amino acid sequence, a heavy chain CDR2 having an amino acid sequence of SEQ ID NO: 11 or an amino acid sequence that is substantially the same as the amino acid sequence, and a heavy chain CDR3 having an amino acid sequence of SEQ ID NO: 12 or an amino acid sequence that is substantially the same as the amino acid sequence, and a light chain variable region having a CDR including CDR1 having an amino acid sequence of SEQ ID NO: 14 or an amino acid sequence that is substantially the same as the amino acid sequence, CDR2 having an amino acid sequence of SEQ ID NO: 15 or an amino acid sequence that is substantially the same as the amino acid sequence, and CDR3 having an amino acid sequence of SEQ ID NO: 16 or an amino acid sequence that is substantially the same as the amino acid sequence;

(c) a combination of a heavy chain variable region having a CDR including a heavy chain CDR1 having an amino acid sequence of SEQ ID NO: 18 or an amino acid sequence that is substantially the same as the amino acid sequence, a heavy chain CDR2 having an amino acid sequence of SEQ ID NO: 19 or an amino acid sequence that is substantially the same as the amino acid sequence, and a heavy chain CDR3 having an amino acid sequence of SEQ ID NO: 20 or an amino acid sequence that is substantially the same as the amino acid sequence, and a light chain variable region having a CDR including CDR1 having an amino acid sequence of SEQ ID NO: 22 or an amino acid sequence that is substantially the same as the amino acid sequence, CDR2 having an amino acid sequence of SEQ ID NO: 23 or an amino acid sequence that is substantially the same as the amino acid sequence, and CDR3 having an amino acid sequence of SEQ ID NO: 24 or an amino acid sequence that is substantially the same as the amino acid sequence;

(d) a combination of a heavy chain variable region having a CDR including a heavy chain CDR1 having an amino acid sequence of SEQ ID NO: 26 or an amino acid sequence that is substantially the same as the amino acid sequence, a heavy chain CDR2 having an amino acid sequence of SEQ ID NO: 27 or an amino acid sequence that is substantially the same as the amino acid sequence, and a heavy chain CDR3 having an amino acid sequence of SEQ ID NO: 28 or an amino acid sequence that is substantially the same as the amino acid sequence, and a light chain variable region having a CDR including CDR1 having an amino acid sequence of SEQ ID NO: 30 or an amino acid sequence that is substantially the same as the amino acid sequence, CDR2 having an amino acid sequence of SEQ ID NO: 31 or an amino acid sequence that is substantially the same as the amino acid sequence, and CDR3 having an amino acid sequence of SEQ ID NO: 32 or an amino acid sequence that is substantially the same as the amino acid sequence;

(e) a combination of a heavy chain variable region having an amino acid sequence of SEQ ID NO: 1 or an amino acid sequence that is substantially the same as the amino acid sequence, and a light chain variable region having an amino acid sequence of SEQ ID NO: 5 or an amino acid sequence that is substantially the same as the amino acid sequence;

(f) a combination of a heavy chain variable region having an amino acid sequence of SEQ ID NO: 9 or an amino acid sequence that is substantially the same as the amino acid sequence, and a light chain variable region having an amino acid sequence of SEQ ID NO: 13 or an amino acid sequence that is substantially the same as the amino acid sequence;

(g) a combination of a heavy chain variable region having an amino acid sequence of SEQ ID NO: 17 or an amino acid sequence that is substantially the same as the amino acid sequence, and a light chain variable region having an amino acid sequence of SEQ ID NO: 21 or an amino acid sequence that is substantially the same as the amino acid sequence; and (h) a combination of a heavy chain variable region having an amino acid sequence of SEQ ID NO: 25 or an amino acid sequence that is substantially the same as the amino acid sequence, and a light chain variable region having an amino acid sequence of SEQ ID NO: 29 or an amino acid sequence that is substantially the same as the amino acid sequence.

The above-mentioned combination of the heavy chain variable region and the light chain variable region has a high inhibitory activity on amyloid fibril formation and corresponds to a combination of the heavy chain variable region and the light chain variable region which have been actually obtained and identified successfully.

The antibody of the present invention can be constructed as a humanized antibody. When the antibody is a humanized antibody, the antibody of the present invention becomes suitable particularly for a treatment purpose.

The antibody of the present invention may be a full antibody (that is, an antibody consisting of a heavy chain and a light chain, both of which has a constant region and a variable region), or may be an antibody fragment such as Fab, Fab', $F(ab')_2$, scFv, or dsFv antibody.

Another aspect of the present invention provides a CDR region of an antibody having a high inhibitory activity on amyloid fibril formation. Specifically, CDR including an amino acid sequence of any of SEQ ID NOs:2-4, 6-8, 10-12, 14-16, 18-20, 22-24, 26-28, and 30-32 is provided. Such CDRs can be used for constructing an antibody having a high inhibitory activity on amyloid fibril formation and the usefulness is high. In particular, they are an important material for constructing a human antibody or a humanized antibody.

Furthermore, the present invention provides an isolated nucleic acid molecule encoding a heavy chain variable region or a light chain variable region of the antibody of the present invention; a heavy chain or a light chain of the antibody of the present invention; or a CDR region of the present invention. By using this nucleic acid molecule, it is possible to produce an antibody having a high inhibitory activity on amyloid fibril formation.

The present invention also provides a vector carrying the above-mentioned nucleic acid molecule so that it can be expressed and provides transformant into which the above-mentioned nucleic acid molecule has been introduced. The vector and the transformant can be used, for example, for producing an antibody having a high inhibitory activity on amyloid fibril formation.

In a further aspect of the present invention, a synthetic lipid membrane for immunizing an animal, which can be used for producing an antibody having an inhibitory activity on amyloid fibril formation is provided. The synthetic lipid membrane of the present invention contains GM1 ganglioside, other lipids, and amyloid β-protein bound to the GM1 ganglioside. The ratio of the other lipids to GM1 ganglioside is in the ratio from 90:10 to 60:40.

The present invention further provides a production method of an antibody using the above-mentioned synthetic lipid membrane. The production method of the present invention includes an immunization step of immunizing a non-human animal with the above-mentioned synthetic lipid membrane; a hybridoma production step of fusing an antibody producing cell taken out from the immunized non-human animal with an immortalized cell so as to obtain a hybridoma; a hybridoma selection step of selecting a hybridoma producing an antibody having a binding property to the above-mentioned synthetic lipid membrane; and an antibody separation step for separating an antibody expressed by the selected hybridoma. In one preferable embodiment, in the hybridoma selection step, a hybridoma producing an antibody having a binding property with respect to the synthetic lipid membrane and not having a binding property with respect to monomer amyloid β protein is selected. Thus, in the production process, an antibody having a binding property with respect to monomer amyloid β protein (that is, non-polymerized amyloid β protein) is excluded. Therefore, it is possible to obtain an antibody having a high specificity with respect to a synthetic lipid membrane, that is, GAβ complex.

The present invention also provides a production method of an antibody using an antibody library. That is to say, the present invention provides a production method of an antibody including a contact step of bringing an antibody library into contact with the above-mentioned synthetic lipid membrane; a clone selection step of selecting a clone having a binding property with respect to the above-mentioned synthetic lipid membrane from the antibody library; and an antibody separation step for separating an antibody expressed by the selected clone. Also in this production method, in order to obtain an antibody having a high specificity with respect to a GAβ3 complex, it is preferable to select a clone having a binding property with respect to the synthetic lipid membrane and not having a binding property with respect to monomer amyloid β protein is selected in the hybridoma selection step.

The present invention further provides an isolated antibody obtained by the above-mentioned production method.

The present invention provides a method for measuring an inhibitory activity on amyloid fibril formation of an antibody. The measuring method of the present invention includes a step of bringing amyloid β protein into contact with the above-mentioned synthetic lipid membrane in the presence or absence of a subject antibody, respectively; and a step of comparing a degree of binding of amyloid β protein to the synthetic lipid membrane and/or polymerization of amyloid β protein between a case where the step is carried out in the presence of a subject antibody and a case where the step is carried out in the absence of a subject antibody. The measuring method of the present invention is used for, for example, measuring the inhibitory activity of the antibody of the present invention, and confirming the inhibitory activity of the antibody obtained by the production method of an antibody of the present invention, and the like.

BRIEF DESCRIPTION OF THE DRAWINGS

FIG. 3 is a table showing a composition (molecular ratio) of GM1 liposome used in an experiment of binding Aβ to GM1 liposome. SM: sphingomyelin, Chol: cholesterol and GM1: GM1 ganglioside. As to liposome without containing GM1, the molecular ratio of GM1 in this composition is made to be 0. The components were mixed so that the total of the concentration (total concentration) of each component becomes 4600 μM.

FIG. 4 shows the results of measurement of a polymerization inhibitory activity on amyloid β protein of the obtained antibodies by three kinds of polymerization systems (A: polymerization initiated by adding an Aβ fibril fragment, B: polymerization initiated from GAβ40, and C: polymerization initiated from GAβ42). *: relative fluorescence intensity is shown when the fluorescence intensity in the polymerization without containing an antibody is defined as 100%. The experiment is carried out three times and typical results are shown. : polymerization reaction initiated by adding fibrous Aβ, polymerization reaction initiated from GAβ40, and polymerization reaction initiated from GAβ42. *: a monoclonal antibody reacting with free Aβ peptide (negative control).

FIG. 9 is a view showing a gene sequence (sequence size: 363) of SEQ ID NO: 86 and an amino acid sequence of SEQ ID NO: 87 of H chain variable region of an antibody 1C9 inhibiting the GM1 ganglioside-bound amyloid O-protein polymerization obtained by immunizing with GM1-containing liposome. CDR denotes a complementarity determining region.

FIG. 10 is a view showing a gene sequence (sequence size: 327) of SEQ ID NO: 88 and an amino acid sequence of SEQ ID NO: 89 of L chain variable region of an antibody 1C9 inhibiting the GM1 ganglioside-bound amyloid β-protein polymerization obtained by immunizing with GM1-containing liposome. CDR denotes a complementarity determining region.

FIG. 11 is a view showing a gene sequence (sequence size: 345) of SEQ ID NO: 90 and an amino acid sequence of SEQ ID NO: 91 of H chain variable region of an antibody 2E12 inhibiting the GM1 ganglioside-bound amyloid β-protein polymerization obtained by immunizing with GM1-containing liposome. CDR denotes a complementarity determining region.

FIG. 12 is a view showing a gene sequence (sequence size: 327) of SEQ ID NO: 92 and an amino acid sequence of SEQ ID NO: 93 of L chain variable region of an antibody 2E 12 inhibiting the GM1 ganglioside-bound amyloid β-protein polymerization obtained by immunizing with GM1-containing liposome. CDR denotes a complementarity determining region.

FIG. 13 is a view showing a gene sequence (sequence size: 339) of SEQ ID NO: 94 and an amino acid sequence of SEQ ID NO: 95 of H chain variable region of an antibody 3G11 inhibiting the GM1 ganglioside-bound amyloid β-protein polymerization obtained by immunizing with GM1-containing liposome. CDR denotes a complementarity determining region.

FIG. 14 is a view showing a gene sequence (sequence size: 339) of SEQ ID NO: 96 and an amino acid sequence of SEQ ID NO: 97 of L chain variable region of an antibody 3G11 inhibiting the GM1 ganglioside-bound amyloid β-protein polymerization obtained by immunizing with GM1-containing liposome. CDR denotes a complementarity determining region.

FIG. 15 is a view showing a gene sequence (sequence size: 366) of SEQ ID NO: 98 and an amino acid sequence of SEQ ID NO: 99 of H chain variable region of an antibody 4E11 inhibiting the GM1 ganglioside-bound amyloid β-protein polymerization obtained by immunizing with GM1-containing liposome. CDR denotes a complementarity determining region.

FIG. 16 is a view showing a gene sequence (sequence size: 342) of SEQ ID NO: 100 and an amino acid sequence of SEQ ID NO: 101 of L chain variable region of an antibody 4E11 inhibiting the GM1 ganglioside-bound amyloid β-protein polymerization obtained by immunizing with GM1-containing liposome. CDR denotes a complementarity determining region.

FIG. 17 shows an example of a configuration of an expression vector. FIG. 17 (A) shows a configuration of an H chain expression vector (BCMGSneo-H). FIG. 17 (B) shows a configuration of an L chain expression vector (BCMGSneo-L).

Figure 1:
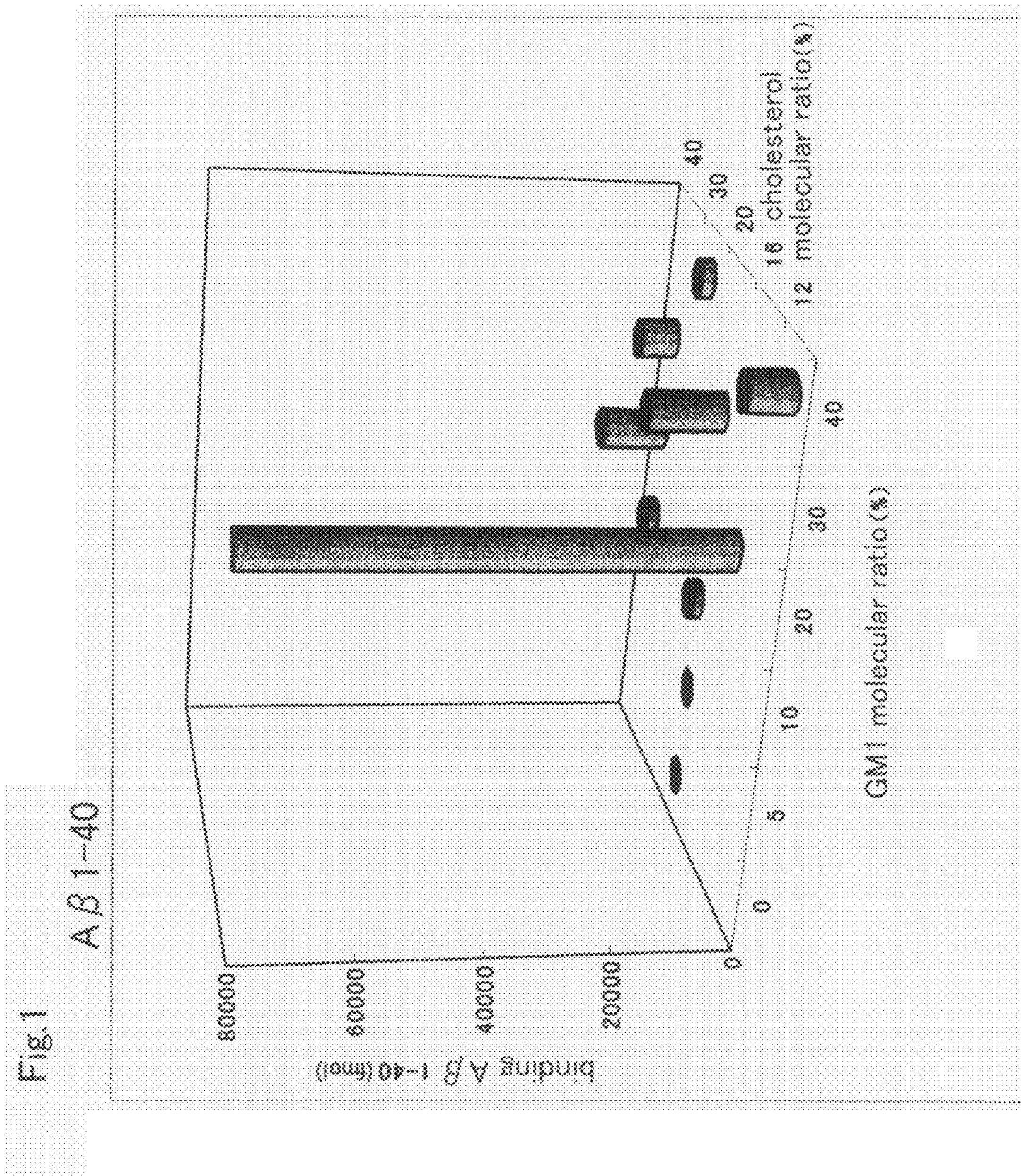
FIG. 1 is a graph showing measurement results of a binding amount of $^{125}$I-labeled amyloid β protein (1-40) to GM1-containing liposome measured while changing the molar ratio (molecular ratio) of GM1 to cholesterol in lipid constituting a liposome. The amount of amyloid β protein (1-40) bound to liposome having 10-40% GM1 composition is large. In particular, the binding amount becomes maximum when the ratio (molecular ratio) of sphingomyelin: cholesterol: GM1 is 64:16:20.

BEST MODE FOR CARRYING OUT THE INVENTION (Explanation of Terms)

For convenience of explanation, the definitions of certain terms as used in this specification are summarized below.

In this specification, amyloid β protein may be abbreviated as "Aβ" and GM1 ganglioside may be abbreviated as "GM1." Similarly, GM1 ganglioside-bound amyloid β-protein may be abbreviated as "GAβ protein" or "GAS complex."

As used in the specification, the term "amyloid β protein polymerization inhibitory activity" is intended to include an activity of suppressing the polymerization of amyloid β protein and an activity of depolymerizing the polymerized amyloid β protein unless otherwise noted.

In this specification, the term "include (comprise) . . . " or "including (comprising) . . . " is used to include the meaning of "consisting of . . . " Therefore, for example, "a product (or method) including (comprising) a plurality of elements (members)" means "a product (or method) formed of the plurality of elements (members)" is naturally taken into consideration.

The term "isolated" refers to a state which is taken out from its original environment (for example, in the case of a natural material, natural environment), that is, a state that is different from the original existing state by an artificial manipulation. Therefore, an "isolated antibody" does not include an antibody in a state in which it is natural state and no external manipulation (artificial manipulation) is given, that is, an antibody produced in the individual body and remain therein. An isolated antibody is typically present in a state in which other kinds of antibodies are not contaminated, that is, present singly (as a group of the same kinds of antibodies). In the case of an "isolated" state of the CDR region, in addition to the state which is present singly, a state which is present together with the other regions of the antibody is included. That is, the term "isolated CDR" includes not only a CDR that is present singly but also a CDR that is present as a part of an isolated antibody is included. The "isolated nucleic acid" may be a nucleic acid that is present as a part of a vector or a composition or a nucleic acid that is present in a cell as an exogenous molecule as long as it is obtained as a result of artificial manipulation.

The term "substantially the same" used in relation to the amino acid sequence means that the difference in the sequence between two amino acid sequences is relatively small and the difference on the sequence does not substantially affect the amyloid β protein polymerization inhibiting ability. An amino acid sequence that is thought to include a part of modification with respect to the standard amino acid sequence in the range that does not substantially affect an amyloid β protein polymerization inhibitory activity is a substantially the same amino acid sequence. The term "the modification of a part of the amino acid sequence" as used herein means that the amino acid sequence is changed by deletion, substitution of one to several amino acids constituting the amino acid sequence, or addition, insertion of one to several amino acids, or the combination thereof. The position of the mutation of the amino acid sequence is not particularly limited. The mutation may be included in a plurality of positions. The "plurality of" as used herein denotes a number corresponding to 10% or less of the entire amino acids constituting the amino acid sequence, preferably a number corresponding to 5% or less, and more preferably a number corresponding to 1% or less.

Whether two amino acids are substantially the same or not can be determined by comparing an amyloid β protein polymerization inhibitory activity (hereinafter, "inhibitory activity" means "amyloid β protein polymerization inhibitory activity" unless otherwise noted) of an antibody of each amino acid sequence (the sequences of the other region are the same). Specifically, the inhibitory activity of the antibody including the standard amino acid sequence is defined as 100% and when the inhibitory activity of an antibody including the amino acid sequence subjected to comparison is, for example, 50% or less with respect to that of the standard amino acid sequence, when the difference in the inhibitory activity is remarkable, substantial identity cannot be recognized. On the other hand, when it is, for example, 70% to 130%, the large difference in inhibitory activity is not observed, substantial identity can be recognized.

An antibody inhibiting the amyloid fibril formation, that is, an antibody having an inhibitory activity on amyloid fibril formation is also referred to as "Aβ polymerization inhibition antibody" in the present specification. Among the Aβ polymerization inhibition antibodies, the antibody specifically recognizing GM1 ganglioside-bound amyloid 5-protein (GAβ complex) is particularly referred to as "anti-GAβ antibody."

As used in the specification, the term "nucleic acid" includes DNA (including cDNA and genomic DNA), RNA (including mRNA) and analogs of the DNA and RNA. The form of the nucleic acid is not limited and may be any of single-stranded and double-stranded, but preferably is double-stranded DNA. Furthermore, codon degeneracy is considered. That is, in the case of the nucleic acid encoding protein, arbitrary base sequence may be included as long as the protein can be obtained as an expression product. In the specification, "nucleic acid encoding a certain protein (for example, an antibody)" is nucleic acid from which the protein can be obtained when it is expressed and includes not only a nucleic acid having a base sequence corresponding to the amino acid sequence of the protein but also a nucleic acid to which a sequence that does not encode the amino acid sequence is added to the nucleic acid (for example, DNA including one or a plurality of introns).

The term "isolated nucleic acid" as used in this specification typically refers to nucleic acid in a state which is separated from the other nucleic acid coexisting in nature in a case of nucleic acid originally occurring in nature (for example, nucleic acid in a human living body). However, the nucleic acid may include a part of the other nucleic acid, for example, a part of the nucleic acid sequence adjacent in the natural state. For example, in the case of genome DNA, the preferable embodiment of the "isolated nucleic acid" in, for example, genome DNA, other DNA component coexisting in the natural state (including adjacent DNA sequence in the natural state) is not substantially contained.

For example, "isolated nucleic acid" such as a cDNA molecule, which is produced by recombinant technique, is preferably nucleic acid that is substantially free of other cellular components, culture solution, and the like. Similarly, when "isolated nucleic acid" is produced by chemical synthesis, it is preferably a nucleic acid in a state which is substantially free of chemical precursors (raw materials) such as dDNTP or other chemicals used in the synthesizing process.

The nucleic acid that is present as a part of a vector or composition, or nucleic acid that is present in a cell as an exogenous molecule can be referred to as "isolated nucleic acid" as long as it is present as a result of artificial manipulation. Unless otherwise noted, simply described "nucleic acid" means "nucleic acid in an isolated state."

In this specification, if necessary, according to practice, the following abbreviations (the terms inside the parentheses) are used.

Heavy chain (H chain), light chain (L chain), heavy chain variable region (VH), light chain variable region (VL), complementarity determining region (CDR), first complementarity determining region (CDR1), second complementarity determining region (CDR2), third complementarity determining region (CDR3), first complementarity determining region of heavy chain (VH CDR1), second complementarity determining region of heavy chain (VH CDR2), third complementarity determining region of heavy chain (VH CDR3), first complementarity determining region of light chain (VL CDR1), second complementarity determining region of light chain (VL CDR2), and third complementarity determining region of light chain (VL CDR3)

The first aspect of the present invention relates to an isolated antibody (Aβ polymerization inhibition antibody) having an inhibitory activity on amyloid fibril formation. The term "antibody" as used herein includes a polyclonal antibody, a monoclonal antibody, a chimeric antibody, a single strand antibody, a CDR-grafted antibody, a humanized antibody, a fragment thereof, or the like.

The Aβ polymerization inhibition antibody of the present invention is characterized in that an inhibitory effect in an amyloid β protein polymerization inhibition test in vitro is 50% or more. With such a high inhibitory effect, the antibody of the present invention can inhibit amyloid fibril formation effectively.

The inhibitory effect of the antibody of the present invention on Aβ polymerization is preferably 70% or more, further preferably 80% or more, yet further preferably 90% or more, and most preferably substantially 100%.

It is preferable that the antibody of the present invention recognizes GM1 ganglioside-bound amyloid β-protein (GAβ complex). This antibody is expected to inhibit the early stage of the amyloid fibril formation. Therefore, the antibody is particularly useful antibody in prevention of the onset of Alzheimer's disease, diagnosis of Alzheimer's disease, and the like.

The "inhibitory activity on amyloid fibril formation (Aβ polymerization inhibitory activity)" in this specification is measured and evaluated by any of the following tests (1 to 3). However, by other tests regarded to be equivalent to the following tests, or by other tests capable of carrying out the same evaluation by converting the test results into the results by the following tests, the amyloid β protein polymerization inhibitory activity may be measured and evaluated.

1. Aβ Polymerization Inhibition Test 1 (Inhibitory Effect on Polymerization Initiated by Adding Aβ Fibril)

1-1. Preparation of Aβ Solution

An Aβ solution is prepared by the following procedure. Firstly, synthetic $A\beta_{1-40}$ (for example, Lot. 501001 (PEPTIDE INSTITUTE INC., Osaka, Japan) or Lot. 519599 (Bachem AG, Switzerland) is dissolved in 0.002% ammonia solution so that it becomes about 500 μM and then centrifuged at 100,000 rpm for three hours (TLA120.0 Rotor, Optima TL, BECKMAN, California, USA). Upper two-thirds of supernatant is collected and the concentration of Aβ is determined. The Aβ solution is divided into some parts and stored at −80° C. before use. Immediately before use, the stored Aβ solution is dissolved and diluted to an appropriate concentration with a physiological Tris buffer solution (TBS: 150 mM NaCl and 10 mM Tris-HCl, pH 7.4).

1-2. Preparation of Fibrous Aβ Solution

A fibrous Aβ solution is prepared by the following procedure. Firstly, synthetic $A\beta_{1-40}$ (for example, Lot. 501001 (PEPTIDE INSTITUTE INC., Osaka, Japan) or Lot. 519599 (Bachem AG, Switzerland) is dissolved in about 500 μM ammonia solution at 4° C. by vortex for a short time, and diluted to 50 μM with an incubation buffer (50 mM phosphate buffer solution, pH 7.5; 100 mM NaCl). The solution is incubated at 37° C. for 24 hours and the mixed solution is centrifuged at $1.6\times10^4$ g at 4° C. for three hours. Precipitates are re-suspended in an ice-cold incubation buffer containing 0.005% $NaN_3$ in an Eppendorf tube, and subjected to sonication on ice by using an ultrasonic disintegrator (UD-201, TOMY, Tokyo, Japan) equipped with Microchip (TP-030, TOMY, Tokyo, Japan) and stored at 4° C. before use.

1-3. Evaluation of Inhibitory Effect (1) Fibrous Aβ solution (5 μl) and Aβ solution (100 μl) are mixed with each other and incubated at 37° C. in the presence of the subject antibody (test group) or in the absence of the subject antibody (control group).

(2) Aβ fibril formation is measured by using Thioflavin T according to Naiki H and Gejyo F (1999) Methods Enzymol 309, 305-318. Firstly, after a predetermined time (for example, after four hours) from the start of incubation, a part of solution (5 μl) is sampled. To this, Thioflavin T (Sigma) is added to bring the final concentration of 5 μM. After dilution with 1 ml of 50 mM glycine-sodium hydroxide buffer, the fluorescence intensity (excitation wavelength: 446 nm, fluorescence wavelength: 490 nm) of Aβ fibril is measured by using a fluorescence spectrophotometer (for example, RF-5300PC, Shimadzu).

(3) The inhibitory effect (inhibitory activity) of the subject antibody is calculated from the following calculation equation.

inhibitory effect(%)=(fluorescence intensity of control group−fluorescence intensity of test group)/fluorescence intensity of control group×100

2. Aβ Polymerization Inhibition Test 2 (Inhibitory Effect on Aβ40 Polymerization Initiated from GAβ40)

2-1. Preparation of Aβ Solution

Aβ solution is prepared by the same procedure as in 1-1. described above.

2-2. Preparation of Synthetic Lipid Containing GM1 Ganglioside

Synthetic lipid containing GM1 ganglioside is prepared by the following procedure. Firstly, cholesterol, sphingomyelin (SIGMA-ALDRICH, St. Louis, Mo., USA) and GM1 (Wako Pure Chemical Industries, Osaka, Japan) are dissolved in a chloroform/methanol mixed solution (1:1) at the ratio of 2:2:1 to bring 1 mol concentration. This mixed solution is dried with nitrogen gas for one hour and stored at −40° C. before use. The lipid mixture dried immediately before use is re-suspended in TBS so that the GM1 concentration is 2.5 mM, followed by freeze thawing by using liquid nitrogen ten times. This lipid suspension is centrifuged at 13,000 rpm for 15 minutes (MX-160, TOMY, Tokyo, Japan) and precipitates are suspended in TBS again to bring the same concentration of GM1. Finally, this suspension is subjected to sonication on ice by using Ultrasonic Disrupter (UD-201, output level 2, TOMY, Tokyo, Japan) equipped with Microchip (TP-030, TOMY, Tokyo, Japan) for five minutes. This is repeated three times.

2-3. Evaluation of Inhibitory Effect (1) Synthetic lipid containing GM1 ganglioside and Aβ solution are mixed with each other and incubated at 37° C. in the presence of the subject antibody (test group) or in the absence of the subject antibody (control group).

(2) Aβ fibril formation is measured by using Thioflavin T according to Naiki H and Gejyo F (1999) Methods Enzymol 309, 305-318. Firstly, after a predetermined time (for example, after 20 hours) from the start of incubation, a part of solution (5 μl) is sampled. To this, Thioflavin T (Sigma) is added to bring the final concentration of 5 μM. After dilution with 1 ml of 50 mM glycine-sodium hydroxide buffer, the fluorescence intensity (excitation wavelength: 446 nm, fluorescence wavelength: 490 nm) of Aβ fibril is measured by using a fluorescence spectrophotometer (for example, RF-5300PC, Shimadzu).

(3) The inhibitory effect (inhibitory activity) of the subject antibody is calculated from the following calculation equation.

inhibitory effect(%)=(fluorescence intensity of control group−fluorescence intensity of test group)/fluorescence intensity of control group×100

Note here that the lipid membrane containing GM1 ganglioside is usually used in a state which is bound to an insoluble support such as beads, microplate, and the like made of resin such as polystyrene resin, polycarbonate resin, silicon resin, nylon resin, and glass and the like.

3. Aβ Polymerization Inhibition Test 2 (Inhibitory Effect on Aβ42 Polymerization Initiated from GAβ42)

An Aβ solution is prepared according to the above-mentioned procedure 1-1. by using synthetic $A\beta_{1-42}$ (for example, Amyloid P-Protein (Human, 1-42), code 4349-v, PEPTIDE INSTITUTE INC., Osaka) instead of $A\beta_{1-40}$. On the other hand, synthetic lipid containing GM1 ganglioside is prepared according to the above-mentioned procedure 2-2. By using these two solutions, the inhibitory effect is evaluated by the same procedure as mentioned in 2-3.

As mentioned in the below-mentioned Examples, the present inventors have succeeded in obtaining four kinds of antibodies (1C9 antibody, 2E12 antibody, 3G11 antibody and 4E11 antibody) having a high inhibitory activity on amyloid fibril formation. As a result of analyzing the sequence of the variable region of each antibody, the following sequence information is obtained. Note here that following the name of antibody, an amino acid sequence of a heavy chain variable region; an amino acid sequence of a heavy chain CDR1; an amino acid sequence of a heavy chain CDR2; an amino acid sequence of a heavy chain CDR3; an amino acid sequence of a light chain variable region; an amino acid sequence of a light chain CDR1; an amino acid sequence of a light chain CDR2; an amino acid sequence of a light chain CDR3 are described in this order.

(1) 1C9 Antibody

SEQ ID NO: 1 (VH); SEQ ID NO: 2 (VH CDR1); SEQ ID NO: 3 (VH CDR2); SEQ ID NO: 4 (VH CDR3); SEQ ID NO: 5 (VL); SEQ ID NO: 6 (VL CDR1); SEQ ID NO: 7 (VL CDR2); SEQ ID NO: 8 (VL CDR3)

(2) 2E12 Antibody

SEQ ID NO:9 (VH); SEQ ID NO:10 (VH CDR1); SEQ ID NO:11 (VH CDR2); SEQ ID NO:12 (VH CDR3); SEQ ID NO:13 (VL); SEQ ID NO:14 (VL CDR1); SEQ ID NO:15 (VL CDR2); SEQ ID NO:16 (VL CDR3)

(3) 3G11 Antibody

SEQ ID NO:17 (VH); SEQ ID NO:18 (VH CDR1); SEQ ID NO:19 (VH CDR2); SEQ ID NO:20 (VH CDR3); SEQ ID NO:21 (VL); SEQ ID NO:22 (VL CDR1); SEQ ID NO:23 (VL CDR2); SEQ ID NO:24 (VL CDR3)

(4) 4E11 Antibody

SEQ ID NO:25 (VH); SEQ ID NO:26 (VH CDR1); SEQ ID NO:27 (VH CDR2); SEQ ID NO:28 (VH CDR3); SEQ ID NO:29 (VL); SEQ ID NO:30 (VL CDR1); SEQ ID NO:31 (VL CDR2); SEQ ID NO:32 (VL CDR3)

The variable region of the antibody of the present invention includes an amino acid sequence which is at least a part of the CDR of the Aβ polymerization inhibition antibody obtained successfully by the present inventors or which is substantially identical thereto. Note here that in the following description, the term "specific amino acid sequence" means "the specific amino acid sequence or an amino acid sequence that is substantially identical to it" unless term "specific amino acid sequence" means only the sequence itself. For example, the amino acid sequence of SEQ ID NO: 1 usually means "amino acid sequence of SEQ ID NO: 1 or an amino acid sequence that is substantially identical to the amino acid sequence of SEQ ID NO: 1."

Specifically, for example, the heavy chain variable region of the antibody of the present invention includes at least one amino acid sequence selected from the group consisting of (1) an amino acid sequence of SEQ ID NO: 2; (2) an amino acid sequence of SEQ ID NO: 3; (3) an amino acid sequence of SEQ ID NO: 4; (4) an amino acid sequence of SEQ ID NO: 10; (5) an amino acid sequence of SEQ ID NO: 11; (6) an amino acid sequence of SEQ ID NO: 12; (7) an amino acid sequence of SEQ ID NO: 18; (8) an amino acid sequence of SEQ ID NO: 19; (9) an amino acid sequence of SEQ ID NO: 20; (10) an amino acid sequence of SEQ ID NO: 26; (11) an amino acid sequence of SEQ ID NO: 27; and (12) an amino acid sequence of SEQ ID NO: 28 as a part or an entire part of CDR (for example, includes as CDR3). Preferably, heavy chain variable region includes two amino acid sequences (for example, includes as CDR2 and CDR3), and further preferably, three amino acid sequences (for example, includes as CDR 1-3). Herein, it is preferable that when the above-mentioned (1), (4), (7) or (10) is included as CDR of the variable region, it is included as CDR1. Similarly, it is preferable that the above-mentioned (2), (5), (8) or (11) is included as CDR2; and it is preferable that the above-mentioned (3), (6), (9) or (12) is included as CDR3.

On the other hand, the light chain variable region of the antibody of the present invention includes at least one amino acid sequence selected from the group consisting of (13) an amino acid sequence of SEQ ID NO: 6; (14) an amino acid sequence of SEQ ID NO: 7; (15) an amino acid sequence of SEQ ID NO: 8; (16) an amino acid sequence of SEQ ID NO: 14; (17) an amino acid sequence of SEQ ID NO: 15; (18) an amino acid sequence of SEQ ID NO: 16; (19) an amino acid sequence of SEQ ID NO: 22; (20) an amino acid sequence of SEQ ID NO: 23; (21) an amino acid sequence of SEQ ID NO: 24; (22) an amino acid sequence of SEQ ID NO: 30; (23) an amino acid sequence of SEQ ID NO: 31; and (24) an amino acid sequence of SEQ ID NO: 32 as a part or an entire part of CDR (for example, includes as CDR3). Preferably, light chain variable region includes two amino acid sequences (for example, includes as CDR2 and CDR3), and further preferably, three amino acid sequences (for example, includes as CDR 1-3). Herein, it is preferable that when the above-mentioned (13), (16), (19) or (22) is included as CDR of the variable region, it is included as CDR1. Similarly, it is preferable that the above-mentioned (14), (17), (20) or (23) is included as CDR2; and it is preferable that the above-mentioned (15), (18), (21) or (24) is included as CDR3.

In the antibody of one preferable embodiment of the present invention, CDR1 of the heavy chain variable region has any of the amino acid sequence of the above-mentioned (1), (4), (7) and (10); CDR2 of the heavy chain variable region has any of the amino acid sequence of the above-mentioned (2), (5), (8) and (11); CDR3 of the heavy chain variable region has any of the amino acid sequence of the above-mentioned (3), (6), (9) and (12); CDR1 of the light chain variable region has any of the amino acid sequence of the above-mentioned (13), (16), (19) and (22); CDR2 of the light chain variable region has any of the amino acid sequence of the above-mentioned (14), (17), (20) and (23); as well as CDR3 of the light chain variable region has any of the amino acid sequence of the above-mentioned (15), (18), (21) and (24).

In the antibody of a further preferable embodiment of the present invention, CDR3 of the heavy chain variable region and the light chain variable region are any of the following combinations (A) to (D).

(A) a combination of heavy chain CDR3: amino acid sequence of SEQ ID NO: 4 and light chain CDR3: amino acid sequence of SEQ ID NO: 8;

(B) a combination of heavy chain CDR3: amino acid sequence of SEQ ID NO: 12 and light chain CDR3: amino acid sequence of SEQ ID NO: 16;

(C) a combination of heavy chain CDR3: amino acid sequence of SEQ ID NO: 20 and light chain CDR3: amino acid sequence of SEQ ID NO: 24; and (D) a combination of heavy chain CDR3: amino acid sequence of SEQ ID NO: 28 and light chain CDR3: amino acid sequence of SEQ ID NO: 32.

These are combinations of CDR3 in 1C9 antibody, 2E12 antibody, 3G11 antibody and 4E11 antibody in this order from the upper combination and it can be expected that they have high Aβ polymerization inhibition activity.

In the antibody of a yet further preferable embodiment of the present invention, CDR2 and CDR3 of the heavy chain variable region and the light chain variable region are any of the following combinations (E) to (H).

(E) a combination of heavy chain CDR2: amino acid sequence of SEQ ID NO: 3; heavy chain CDR3: amino acid sequence of SEQ ID NO: 4; light chain CDR2: amino acid sequence of SEQ ID NO: 7; and light chain CDR3: amino acid sequence of SEQ ID NO: 8;

(F) a combination of heavy chain CDR2: amino acid sequence of SEQ ID NO: 11; heavy chain CDR3: amino acid sequence of SEQ ID NO: 12; light chain CDR2: amino acid sequence of SEQ ID NO: 15; and light chain CDR3: amino acid sequence of SEQ ID NO: 16;

(G) a combination of heavy chain CDR2: amino acid sequence of SEQ ID NO: 19; heavy chain CDR3: amino acid sequence of SEQ ID NO: 20; light chain CDR2: amino acid sequence of SEQ ID NO: 23; and light chain CDR3: amino acid sequence of SEQ ID NO: 24; and (E) a combination of heavy chain CDR2: amino acid sequence of SEQ ID NO: 27; heavy chain CDR3: amino acid sequence of SEQ ID NO: 28; light chain CDR2: amino acid sequence of SEQ ID NO: 31; and light chain CDR3: amino acid sequence of SEQ ID NO: 32.

These are combinations of CDR2 and CDR3 in 1C9 antibody, 2E12 antibody, 3G11 antibody and 4E11 antibody in this order from the upper combination. Further higher Aβ polymerization inhibitory activity can be expected.

In the antibody of the most preferable embodiment of the present invention, CDR1 to CDR3 of the heavy chain variable region and the light chain variable region are any of the following combinations (I) to (L).

(I) a combination of heavy chain CDR1: amino acid sequence of SEQ ID NO: 2; CDR2: amino acid sequence of SEQ ID NO: 3; heavy chain CDR3: amino acid sequence of SEQ ID NO: 4; light chain CDR1: amino acid sequence of SEQ ID NO: 6; light chain CDR2: amino acid sequence of SEQ ID NO: 7; and light chain CDR3: amino acid sequence of SEQ ID NO: 8;

(J) a combination of heavy chain CDR1: amino acid sequence of SEQ ID NO: 10; CDR2: amino acid sequence of SEQ ID NO: 11; heavy chain CDR3: amino acid sequence of SEQ ID NO: 12; light chain CDR1: amino acid sequence of SEQ ID NO: 14; light chain CDR2: amino acid sequence of SEQ ID NO: 15; and light chain CDR3: amino acid sequence of SEQ ID NO: 16;

(K) a combination of heavy chain CDR1: amino acid sequence of SEQ ID NO: 18; CDR2: amino acid sequence of SEQ ID NO: 19; heavy chain CDR3: amino acid sequence of SEQ ID NO: 20; light chain CDR1: amino acid sequence of SEQ ID NO: 22; light chain CDR2: amino acid sequence of SEQ ID NO: 23; and light chain CDR3: amino acid sequence of SEQ ID NO: 24; and (L) a combination of heavy chain CDR1: amino acid sequence of SEQ ID NO: 26; CDR2: amino acid sequence of SEQ ID NO: 27; heavy chain CDR3: amino acid sequence of SEQ ID NO: 28; light chain CDR1: amino acid sequence of SEQ ID NO: 30; light chain CDR2: amino acid sequence of SEQ ID NO: 31; and light chain CDR3: amino acid sequence of SEQ ID NO: 32;

These are combinations of CDR1 to CDR3 in 1C9 antibody, 2E12 antibody, 3G11 antibody and 4E11 antibody in this order from the upper combination. Further higher Aβ polymerization inhibitory activity can be expected.

A part other than a complementarity determining region (CDR) of the variable region is called "framework" for holding the structure of CDR. In the variable region of the antibody of the present invention, the sequence of the framework region (FR region) is not particularly limited as long as it does not substantially affect the Aβ polymerization inhibitory activity. For example, an amino acid sequence obtained by modifying the FR region of 1C9 antibody, 2E12 antibody, 3G11 antibody or 4E11 antibody or a part thereof can be employed as a FR region of the antibody of the present invention. As mentioned below, when the antibody of the present invention is constructed as a humanized antibody, a FR region of the well-known human antibody can be used. Furthermore, when, for example, an antibody used as a reagent for detection or an antibody applied to non-human animal species is constructed, occasionally, the effect can be expected although a FR region of the human antibody is not used, or the use of a FR region of the human antibody is not suitable. In such a case, a FR region of non-human animal species (for example, mouse or rat) can be used.

The antibody of one embodiment of the present invention includes a constant region in addition to a variable region (for example, an IgG antibody, etc.). The sequence of the constant region in this embodiment is not particularly limited. For example, as mentioned below, when the antibody of the present invention is constructed as a humanized antibody, a constant region of the well-known human antibody can be used. Furthermore, similar to the above-mentioned constant region, a constant region of non-human animal species (for example, mouse or rat) can be used. The sequence may be the above-mentioned amino acid sequence or an amino acid sequence a part of which has been modified.

One embodiment of the antibody of the present invention is a humanized antibody. The "humanized antibody" as used herein means an antibody whose structure is similar to the human antibody. The humanized antibody includes a human type chimeric antibody in which only a constant region of the antibody is replaced with that of a human antibody, and a human type CDR-grafted antibody in which a constant region and a part other than CDR (complementarity determining region) are replaced with those of an human antibody (P. T. Johons et al., Nature 321,522 (1986)). In order to improve the antigen binding activity of a human type CDR-grafted antibody, an improved technology of a method for selecting a human antibody FR that is highly homologous to a mouse antibody, a method for producing a highly homologous humanized type antibody, a method for replacing amino acid of FR region after mouse CDR is transplanted into a human antibody has been already developed (see U.S. Pat. Nos. 5,585,089, 5,693,761, 5,693,762, 6,180,370, European Patent No. 451216, European Patent No. 682040, and U.S. Pat. No. 2,828,340, etc.). Such technology can be used for producing the human-type antibody of the present invention.

A human-type chimeric antibody can be produced by replacing a constant region of an antibody (for example, 1C9 antibody, 2E12 antibody, 3G11 antibody or 4E11 antibody) having the above-mentioned H chain variable region structure and/or L chain variable region structure with a constant region of the human antibody. As the constant region of the human antibody, a well-known constant region can be employed. Hereinafter, one example of the production method of human-type chimeric antibody is described.

Firstly, mRNA is extracted from a hybridoma producing a mouse Aβ polymerization inhibition antibody and cDNA is synthesized according to the routine method. The synthesized cDNA is introduced into a vector and cDNA library is constructed. A vector containing H chain gene and L chain gene is selected from the cDNA library by using an H chain gene fragment and an L chain gene fragment as a probe. By sequencing of the inserted sequence of the selected vector, the sequence of genes of H chain variable region and L chain variable region can be determined. Based on the thus obtained sequence data, DNA encoding the H chain variable region is produced by chemical synthesis, biochemical cleavage/rebinding, and the like. The obtained DNA encoding the H chain variable region is ligated into DNA encoding the human H chain constant region so as to produce an H chain expression vector. An example of the expression vector includes, but not limited to, an SV40 virus based vector, an EB virus based vector, a BPV (papilloma virus) based vector, and the like. On the other hand, by the similar method, L chain expression vector is produced. With these H chain expression vector and L chain expression vector, host cell are co-transformed. As the host cells, CHO (Chinese Hamster Ovary) cells (A. Wright & S. L. Morrison, J. Immunol. 160, 3393-3402 (1998)), SP2/0 cells (mouse myeloma) (K. Motmans et al., Eur. J. Cancer Prev. 5, 512-519 (1996), R. P. Junghans et al., Cancer Res. 50, 1495-1502 (1990)), and the like, can be preferably used. Furthermore, for transformation, a Lipofectin method (R. W. Malone et al., Proc. Natl. Acad. Sci. USA 86,6077 (1989), P. L. Felgner et al., Proc. Natl. Acad. Sci. USA 84,7413 (1987), an electroporation method, a calcium phosphate method (F. L. Graham & A. J. van der Eb, Virology 52, 456-467 (1973)), a DEAE-Dextran method, and the like can be preferably used.

After a transformant is cultured, a human-type chimeric antibody is separated from the inside of the transformant cells or its culture solution. For separation and purification of an antibody, methods such as centrifugation, ammonium sulfate fractionation, salting out, ultrafiltration, an affinity chromatography, an ion exchange chromatography, a gel filtration chromatography, and the like, can be used by appropriately combining thereof.

On the other hand, a human type CDR-grafted antibody can be produced by, for example, the following method. Firstly, by the method described in the above-mentioned column of the chimeric antibody, an amino acid sequence of an H chain variable region and an L chain variable region of a mouse Aβ antibody and a base sequence encoding thereof are determined. In addition, an amino acid sequence and a base sequence of each CDR region are determined.

Specific base sequence of CDR includes, for example, the following base sequences.

H chain CDR1 (VH CDR1): base sequence of any of SEQ ID NOs: 34, 42, 50 and 58

H chain CDR2 (VH CDR2): base sequence of any of SEQ ID NOs: 35, 43, 51 and 59

H chain CDR3 (VH CDR3): base sequence of any of SEQ ID NOs: 36, 44, 52 and 60

L chain CDR1 (VH CDR1): base sequence of any of SEQ ID NOs: 38, 46, 54 and 62

L chain CDR2 (VH CDR2): base sequence of any of SEQ ID NOs: 39, 47, 55 and 63

L chain CDR3 (VH CDR3): base sequence of any of SEQ ID NOs: 40, 48, 56 and 64

As the base sequence of CDR, any of the following combinations is preferably used.

(1) a combination of VH CDR1: base sequence of SEQ ID NO: 34, VH CDR2: base sequence of SEQ ID NO: 35, VH CDR3: base sequence of SEQ ID NO: 36, VL CDR1: base sequence of SEQ ID NO: 38, VL CDR2: base sequence of SEQ ID NO:39, and VL CDR3: base sequence of SEQ ID NO: 40;

(2) a combination of VH CDR1: base sequence of SEQ ID NO: 42, VH CDR2: base sequence of SEQ ID NO: 43, VH CDR3: base sequence of SEQ ID NO: 44, VL CDR1: base sequence of SEQ ID NO: 46, VL CDR2: base sequence of SEQ ID NO:47, and VL CDR3: base sequence of SEQ ID NO: 48;

(3) a combination of VH CDR1: base sequence of SEQ ID NO: 50, VH CDR2: base sequence of SEQ ID NO: 51, VH CDR3: base sequence of SEQ ID NO: 52, VL CDR1: base sequence of SEQ ID NO: 54, VL CDR2: base sequence of SEQ ID NO:55, and VL CDR3: base sequence of SEQ ID NO: 56, and (4) a combination of VH CDR1: base sequence of SEQ ID NO: 58, VH CDR2: base sequence of SEQ ID NO: 59, VH CDR3: base sequence of SEQ ID NO: 60, VL CDR1: base sequence of SEQ ID NO: 62, VL CDR2: base sequence of SEQ ID NO:63, and VL CDR3: base sequence of SEQ ID NO: 64.

These are combinations of each CDR in 1C9 antibody, 2E12 antibody, 3G11 antibody and 4E11 antibody in this order from the upper combination.

Next, FRs (framework regions) that are present so that they sandwich the CDR region are selected. For selecting FR, approximately three methods can be employed. The first method is a method using a human antibody frame, such as NEWM, REI, whose three-dimensional conformation has been already clarified (Riechmann L. et al., Nature 332, 323-3Z7 (1988); Tempst, P R. et al., Protein Engineering 7, 1501-1507 (1994); Ellis J H. Et al., J. Immunol. 155, 925-937 (1995)). The second method is a method of selecting a human antibody variable region having the highest homology with respect to the target mouse antibody variable region from database, and using the FR (Queen C. et al., Proc Natl Acad Sci USA 86, 10029-10033 (1989); Rozak M J. et al., J Biol Chem 271, 22611-22618 (1996); Shearman C W. et al., J. Immunol 147, 4366-4373 (1991)). The third method is a method of selecting amino acid used most commonly in FR of a human antibody (Sato K. et al., Mol Immunol 31, 371-381 (1994); Kobinger F. et al., Protein Engineering 6, 971-980 (1993); Kettleborough C A. et al., Protein Engineering 4, 773-783 (1991)). In the present invention, any of these methods can be used.

An amino acid sequence obtained by modifying the amino acid sequence of the selected human FR can be used as an amino acid sequence of FR as long as the finally obtained human type CDR-grafted antibody effectively inhibits the Aβ fibril formation. In particular, when a part of the amino acid of the selected human FR is changed to the amino acid of FR of the antibody from which the CDR is derived, the probability that the property of the antibody is maintained is high. The number of amino acids to be modified is preferably 30% or less with respect to the entire FR, more preferably 20% or less with respect to the entire FR, and yet further preferably 10% or less with respect to the entire FR.

Next, by combining the FR selected from any of these methods and the above-mentioned CDR, DNA encoding an H chain variable region and an L chain variable region is designed. Based on this design, DNA encoding an H chain variable region and DNA encoding an L chain variable region are produced respectively by chemical synthesis, biochemical cleavage/re-binding, and the like. DNA encoding an H chain variable region is incorporated into an expression vector together with DNA encoding a human immunoglobulin H chain constant region to construct an H chain expression vector. Similarly, DNA encoding an L chain variable region is incorporated into an expression vector together with DNA encoding a human immunoglobulin L chain constant region to construct an L chain expression vector. An example of the expression vector includes, but not limited to, an SV40 virus based vector, an EB virus based vector, a BPV (papilloma virus) based vector, and the like.

With the H chain expression vector and L chain expression vector produced by the above-mentioned method, host cells are co-transformed. As the host cells, CHO (Chinese Hamster Ovary) cells (A. Wright & S. L. Morrison, J. Immunol. 160, 3393-3402 (1998)), SP2/0 cells (mouse myeloma) (K. Motmans et al., Eur. J. Cancer Prev. 5, 512-519 (1996), R. P. Junghans et al., Cancer Res. 50, 1495-1502 (1990)), and the like, can be preferably used. Furthermore, for transformation, a Lipofectin method (R. W. Malone et al., Proc. Natl. Acad. Sci. USA 86,6077 (1989), P. L. Felgner et al., Proc. Natl. Acad. Sci. USA 84,7413 (1987), an electroporation method, a calcium phosphate method (F. L. Graham & A. J. van der Eb, Virology 52, 456-467 (1973)), a DEAE-Dextran method, and the like can be preferably used.

After a transformant is cultured, a human type CDR-grafted antibody is separated from the inside of the transformant cells or its culture solution. For separation and purification of an antibody, methods such as centrifugation, ammonium sulfate fractionation, salting out, ultrafiltration, an affinity chromatography, an ion exchange chromatography, a gel filtration chromatography, and the like, can be used by appropriately combining thereof.

Antibody fragments can be produced based on the antibody of the present invention or based on the sequence information of gene encoding the antibody of the present invention. Example of the antibody fragment include Fab, Fab', $F(ab')_2$, scFv, and dsFv antibodies.

Fab is obtained by digesting IgG with papain in the presence of system. Fab is an antibody fragment having a molecular weight of about 50,000 and includes the L chain and H chain variable regions and an H chain fragment composed of a CH1 domain and a part of a hinge portion. In the present invention, Fab can be obtained by digesting the above-mentioned antibody with papain. Furthermore, Fab can be also prepared from a transformant formed by using a vector in which DNAs encoding a part of the H chain and the L chain are incorporated.

Fab' is an antibody fragment having a molecular weight of about 50,000, which can be obtained by cleaving the disulfide bond between the H chains of F(ab')2 mentioned below. In the present invention, Fab' is prepared by digesting the above-mentioned antibody with pepsin and cleaving the disulfide bond by using a reducing agent. Furthermore, similar to Fab, Fab' can be also prepared by genetically engineering using a DNA encoding Fab'.

$F(ab')_2$ is obtained by digesting IgG with papain. $F(ab')_2$ is a fragment having a molecular weight of about 100,000, in which (Fab') including the L chain and the H chain variable regions and an H chain fragment composed of a CH1 domain and a part of a hinge portion are bonded to each other via the disulfide bond. In the present invention, $F(ab')_2$ can be obtained by digesting the above-mentioned antibody with pepsin. Furthermore, similar to Fab, $F(ab')_2$ can be also prepared by genetically engineering by using a DNA encoding $F(ab')_2$.

ScFv is an antibody fragment formed in a form of a single-strand conformation by linking Fv, composed of the H chain variable region and the L chain variable region, in a manner that the C-terminal of one chain is linked to the N-terminal of the other chain via a suitable peptide linker. As a peptide linker, for example, $(GGGGS)_3$ etc. having high flexibility can be used. For example, by using DNAs encoding the H chain variable region and the L chain variable region and a DNA encoding a peptide linker, a DNA encoding scFv antibody is constructed and incorporated into an appropriate vector to form a transformant. From the transformant, scFv can be also prepared.

DsFv is an Fv fragment in which Cys residues are introduced into a suitable positions of the H chain variable region and the L chain variable region, and the H chain variable region and the L chain variable region are stabilized via the disulfide bond. The position into which Cys residue of each chain is introduced can be determined based on the three-dimensional conformation predicted by molecule modeling. In the present invention, the three-dimensional conformation is predicted from, for example, the amino acid sequences of the H chain variable region and L chain variable region. Based on such prediction, DNAs encoding the H chain variable region and the L chain variable region, in which a mutant is introduced, are constructed, respectively and incorporated into a suitable vector to form a transformant. From the transformant, dsFv can be also prepared.

Note here that antibody fragments can be multimerized by linking scFv antibody, dcFv antibody, and the like by using a suitable linker, or by fusing streptavidin thereto.

By fusing or binding a low molecular compound, protein, labeled and the like, to the antibody (including an antibody fragment) of the present invention, a fused antibody or labeled antibody can be constructed. As the labeled material, radioactive substance such as $^{125}I$, peroxidase, β-D-galactosidase, microperoxidase, horseradish peroxidase (HRP), fluorescein isothiocyanate (FITC), rhodamine isothiocyanate (RITC), alkaline phosphatase, biotin, and the like, can be used.

Since the antibody (including an antibody fragment) of the present invention can effectively suppresses amyloid fibril formation, it is useful for diagnosis, prevention and treatment, and the like, of Alzheimer's disease. That is to say, it is thought that Alzheimer's disease can be diagnosed, prevented or treated by using the antibody of the present invention. In other words, by using the antibody of the present invention, a diagnosing method, preventing method and treating method of Alzheimer's disease are provided. Furthermore, by using the antibody of the present invention, drugs for Alzheimer's disease (diagnosis drug, prevention drug, or treatment drug) can be produced. Herein, by using a humanized antibody of the present invention, even if it is applied to a human, since it is recognized to be human protein, it is not likely to be excluded from the circulation system and it does not easily cause allergy reaction. Therefore, it is thought that it can be used as a preferable diagnosis drug and the like.

As a result of the investigation of the present inventors, it has been determined that a lipid membrane (lipid membrane including GM1) to be used in the above-mentioned Aβ polymerization inhibition test is effective as an antigen for obtaining the Aβ polymerization inhibition antibody. Based on this finding, a further aspect of the present invention provides a synthetic lipid membrane for immunizing an animal, which includes GM1 ganglioside, other lipids, and amyloid β-protein (Aβ) bound to the GM1 ganglioside, in which the component ratio (molecular ratio) of the other lipids to GM1 ganglioside is in the range from 90:10 to 60:40.

The synthetic lipid membrane of the present invention typically three components, that is, GM1 ganglioside, other lipids and amyloid 13 protein. The component ratio of the synthetic lipid membrane of the present invention in the typical embodiment is the other components (however, the amount of amyloid β protein is not included): GM1 ganglioside=90:10 to 60:40.

The term "lipid" as used in this specification is intended to comprehensively mean simple lipid, complex lipid (for example, sphingomyelin, ganglioside) and derived lipid (for example, cholesterol).

The synthetic lipid membrane of the present invention is used as an antigen for producing an Aβ polymerization inhibition antibody and in particular it can be used as an antigen for efficiently producing anti-GAβ antibody. Examples of animals to be used in immunization with the synthetic lipid membrane of the present invention include, but are not limited to, mouse, rat, rabbit, sheep, goat, and the like. The immunization method is not also particularly limited and intravenous injection, intraperitoneal injection, injection to footpad, and the like, can be employed.

In a preferable embodiment of the present invention, the component ratio (molecular ratio) of the synthetic lipid membrane is other lipids: GM1 ganglioside=85:15 to 70:30. In a further preferable embodiment of the present invention, the component ratio (molecular ratio) of the synthetic lipid membrane is other lipids: GM1 ganglioside=about 80:20. The synthetic lipid membrane having this range of content of GM1 ganglioside has further excellent Aβ polymerization initiating activity. The use of this GM1 ganglioside makes it possible to produce an antibody having a high Aβ polymerization inhibitory activity more efficiently.

As the lipid component that is one of the components of the synthetic lipid membrane of the present invention, sphingomyelin is preferably used.

In one embodiment of the present invention, the synthetic lipid membrane includes cholesterol as one of the lipid components. With cholesterol, formation of GM1 "cluster" on membrane is promoted. Thus, the binding between Aβ and GM1 is expected to be promoted. Furthermore, since such a synthetic lipid membrane has a configuration closer to that of the nerve cell membrane in the brain in which amyloid fibril is formed, it becomes an antigen promoting the production of an antibody that efficiently inhibits the amyloid fibril formation.

The component ratio (molecular ratio) of the synthetic lipid membrane in this embodiment is remaining lipids: cholesterol:GM1 ganglioside=80-20:10-40:10-40. As mentioned in the below-mentioned Examples, by using the synthetic lipid membrane with the component ratio, the Aβ polymerization inhibition antibody can be efficiently produced. It is preferable that remaining lipids: cholesterol:GM1 ganglioside=70-50:10-20:20-30. The synthetic lipid membrane with the component ratio has more preferable Aβ polymerization initiating activity. Use of this synthetic lipid membrane makes it possible to produce an antibody having a high Aβ polymerization inhibitory activity more efficiently.

Specific preferable examples can include a synthetic lipid membrane having a component ratio (molecular ratio) of sphingomyelin (corresponding to the remaining lipid): cholesterol:GM1 ganglioside=64:16:20.

As GM1, commercially available GM1 (product of Wako Pure Chemical Industries, Osaka, Japan) can be used. As Aβ, for example, commercially available $A\beta_{1-40}$ (Amyloid O—Protein (Human, 1-40) code 4307-v Lot. 501001, PEPTIDE INSTITUTE INC., Osaka, Japan, Lot. 519599, Bachem AC; Switzerland), $A\beta_{1-42}$ (for example, Amyloid P-Protein (Human, 1-42), code 4349-v, PEPTIDE INSTITUTE INC., Osaka), and the like, can be used.

The synthetic lipid membrane of the present invention can be prepared by bringing Aβ into contact with a lipid membrane containing a component other than Aβ (for details of the preparation method, see the below-mentioned Examples). It is preferable that contact time of the lipid membrane and Aβ is short. Further preferably, both are brought into contact with each other instantly because long time reaction makes Aβ fibril formation to proceed excessively. Note here that the synthetic lipid membrane of the present invention is usually prepared in a liposome form in a solution.

Production of Aβ polymerization inhibition antibody using the synthetic lipid membrane of the present invention is carried out by using an immunological technique, a method using an antibody library, such as a phage display and a ribosome display, and the like.

The preparation of a polyclonal antibody by using immunological technique can be carried out by the following procedure. An antigen (the above-mentioned synthetic lipid membrane) is prepared and a non-human animal such as mouse, rat, rabbit, goat and the like is immunized with this antigen. When effective immune initiation cannot be expected because the molecular weight is low, it is preferable to use an antigen to which a carrier protein is bound. Examples of the carrier protein include KLM (Keyhole Light Hemocyanin), BSA (Bovine Serum Albumin), OVA (Ovalbumin), and the like. For binding the carrier protein, a carbodiimide method, a glutaraldehyde method, a diazo condensation method, a MBS (m-Maleimidobenzoyl-N-hydroxysuccinimide ester) method can be used.

Immunization is repeated if necessary. At the time when the antibody titer is sufficiently increased, blood is collected. The collected blood is subjected to, for example, centrifugation so as to obtain serum. From the obtained antiserum, an antibody is separated. For separating the target antibody, it is possible to use a synthetic lipid membrane used as an antigen. Specifically, firstly, the antiserum and the synthetic lipid membrane are brought into contact with each other. As a result, a component bound to the synthetic lipid membrane is separated, and target antibody is obtained. In addition to the above-mentioned procedure, it is preferable that a step of bringing the separated antibody and monomer amyloid β protein into contact with each other and selecting the antibody that is not bound to the monomer amyloid β protein is carried out. By carrying out this step, it is possible to obtain an antibody that does not recognize monomer amyloid β protein but recognize only GAβ complex. That is to say, an antibody having a high specificity to GAβ complex can be obtained. Such an antibody is suitable for the application in which GAβ complex is a target because of its high specificity. Furthermore, based on it, it is possible to construct a humanized antibody or human-type antibody exhibiting high specificity to GAβ complex and excellent effect in prevention, treatment and diagnosis of Alzheimer's disease.

On the other hand, a monoclonal antibody can be prepared by the following procedure. Firstly, an immunization (operation) is carried out by the same procedure as mentioned above. Immunization is repeated if necessary. At the time when the antibody titer is sufficiently increased, antibody-producing cells are extracted from an immunized animal. Next, the obtained antibody producing cells and myeloma cells are fused so as to obtain a hybridoma. Subsequently, this hybridoma is made into monoclonal. Then, a clone for producing an antibody having a high specificity with respect to the synthetic lipid membrane of the present invention is selected. Specifically, by bringing a culture supernatant of hybridoma into contact with the synthetic lipid membrane, it is determined whether or not an antibody having a binding property with respect to the synthetic lipid membrane is present in the culture supernatant. Then, hybridoma clone that has determined that the synthetic lipid membrane is present is selected. In this selection step, it is preferable that a clone producing an antibody having a binding property with respect to a monomer amyloid β protein is excluded. That is to say, it is preferable to select hybridoma producing an antibody which has a binding property with respect to the synthetic lipid membrane and which does not have a binding property with respect to a monomer amyloid β protein because it is possible to obtain a clone producing an antibody that does not recognize monomer amyloid β protein but recognizes only a GAβ complex. Note here that firstly, a hybridoma clone producing an antibody having a binding property with respect to the synthetic lipid membrane may be selected and then may be made into monoclonal form.

Next, the target antibody is separated from a culture solution of the selected clone. On the other hand, the selected clone (hybridoma) is transplanted into the peritoneal cavity of a non-human animal (for example, mouse) and proliferated in the abdominal dropsy. Then, the target antibody can be separated from the target antibody.

For separating the antibody from the culture solution or the abdominal dropsy of the hybridoma, an affinity chromatography using protein G and protein A and the like is preferably employed. Furthermore, an affinity chromatography in which an antigen is made to be a solid phase can be employed. Furthermore, a method such as an ion exchange chromatography, a gel filtration chromatography, ammonium sulfate fractionation, centrifugation, and the like can be employed. These methods can be used singly or in an arbitrary combination thereof. Note here that as to the method for producing an antibody, see, for example, Kohler and Milstein (1975) Nature 256:495-497; Brown et al. (1981) J. Immunol. 127: 539-46; Brown et al. (1980) J. Biol. Chem. 255:4980-83; Yeh et al. (1976) Proc. Natl. Acad. Sci. USA 76:2927-31; Yeh et al. (1982) Int. J. Cancer 29:269-75; Kozbor et al. (1983) Immunol. Today 4:72; Kenneth, R. H. in Monoclonal Antibodies: A New Dimension In Biological Analyses, Plenum Publishing Corp., New York, N.Y. (1980); Lerner, E. A. (1981) Yale J. Biol. Med. 54:387-402; Gefter, M. L. et al. (1977) Somatic Cell Genet. 3: 231-36.

The phage display method is a system for expressing an exogenous gene as fusion protein to code protein (cp3 and cp8) of a fibrous phage such as M13. In the phage display method, by incorporating a gene of a mixture of the different proteins or peptides into phage DNA, about $10^6$ to $10^{12}$ phage libraries are constructed. Some phage antibody libraries are provided commercially or non-commercially (for example, Hucal GOLD (MorphoSys), GRIFFIN. 1 LIBRARY: Griffiths, A D et al. EMBO J.13: 3245-3260 (1994) "Nissim Library" (Nissim, A et al. EMBO J.13: 692-698). Among them, appropriate one can be selected and used.

The selection of the specific phage from the phage library is carried out by an operation called panning. The panning typically includes a series of steps of reacting the target protein with the phage library (contact), excluding unbound phages (washing), eluting bound phages, and infecting the collected phages with *Escherichia coli* (proliferation of phages). With panning, a phage presenting a protein having a binding property with respect to the target protein is concentrated. In general, the panning is repeated until a sufficient concentration is confirmed. By infecting an appropriate host cell with the thus screened and concentrated phages, protein (peptide) presented by the phage can be expressed as a soluble molecule. Alternatively, an exogenous gene is cleaved out from the screened and concentrated phages, and the exogenous gene is incorporated into an appropriate expression vector so as to express the exogenous gene by using an appropriate expression system. Thus, the presented protein (peptide) may be made to be soluble. The expressed products can be recovered by a combination of methods such as centrifugation, ammonium sulfate fractionation, salting out, ultrafiltration, an affinity chromatography, an ion exchange chromatography, and a gel filtration chromatography.

As to the phage display method, see, various documents, for example, Huse et al. (1989) Science 246:1275-1281; McCafferty et al. (1990) Nature 348:552-554; Fuchs et al. (1991) Bio/Technology 9:1370-1372; Barbas et al. (1991) Proc. Natl. Acad. Sci. USA 88:7978-7982; Hoogenboom et al. (1991) Nucleic Acids Res. 19:4133-4137; Gram et al. (1992) Proc. Natl. Acad. Sci. USA 89:3576-3580; Hay et al. (1992) Hum. Antibod. Hybridomas 3:81-85; Griffiths et al. (1993) EMBO J. 12:725-734; PCT International Publication WO 90/02809; PCT International Publication WO 92/20791; PCT International Publication WO 92/15679; PCT International Publication WO 92/09690, etc. Furthermore, kits for forming and screening a phage display library are commercially available and they can be preferably used.

The ribosome display method is a method in which a termination codon is mutated so as to form a state in which the transcriptional product and the translation product of the template DNA are bound to ribosome and screening to, for example, a target is carried out by using the thus obtained protein/mRNA/ribosome complex (ARM). An example in which the ribosome display is applied to the manufacture of the antibody library is disclosed in U.S. Pat. Nos. 5,643,768 and 5,658,754.

When an antibody is prepared by using a genetic engineering technique such as a phage display method or a ribosome display method, for example, an animal is immunized with an antigen and then mRNA and DNA are taken out from the immune system cells so as to obtain an antibody gene including an antigen-binding domain by a gene amplification method such as PCR and RT-PCR. By using the obtained antibody gene, an antibody library such as a phage display library is constructed. Next, a clone having a specific binding property to an antigen (synthetic lipid membrane) is selected from the thus obtained antibody libraries. That is to say, by bringing the antibody library and the synthetic lipid membrane of the present invention into contact with each other, a clone showing a binding property with respect to the synthetic lipid membrane is selected. Also in this method, it is preferable that a clone showing a binding property with respect to monomer amyloid β protein is excluded because it is possible to obtain a highly specific antibody showing a binding property only to the GAβ complex.

Note here that a clone may be in any form of polyclone, oligoclone, and monoclone as long as it includes a clone having (expressing) a specific binding molecule. When the target clone is selected, the antibody presented by the clone is separated by the above-mentioned procedure.

A further aspect of the present invention relates to an antibody of the present invention, that is, an antibody that inhibits Aβ fibril formation (Aβ polymerization inhibition antibody) or DNA encoding an antibody fragment. This aspect also provides a human-type chimeric antibody having an inhibitory activity on Aβ fibril formation, DNA encoding a human type CDR-grafted antibody, and DNA encoding a human type antibody fragment. Furthermore, these antibodies or DNA encoding H chain or L chain of the antibody fragment is included in the present invention. Furthermore, these antibodies or DNA encoding H chain or L chain of the antibody fragment is included in the present invention. In this case, DNA may be DNA configured by excluding a signal portion. A specific example of a DNA sequence of an H chain variable region includes a sequence shown in SEQ ID NOs: 33, 41, 49 or 57. Similarly, a specific example of a DNA sequence of an L chain variable region includes a sequence shown in SEQ ID NOs: 37, 45, 53 or 61.

Furthermore, a sequence of nucleic acid encoding a variable region CDR of the Aβ polymerization inhibition antibody is included in the present invention. The specific examples include base sequences (for example, base sequence of any of SEQ ID NOs: 34-36, 38-40, 42-44, 46-48, 50-52, 54-56, 58-60, and 62-64) encoding any of amino acid sequence of SEQ ID NO: 2-4, 6-8, 10-12, 14-16, 18-20, 22-24, 26-28, and 30-32. The above-mentioned nucleic acid can be prepared by appropriately using a chemical technique, a genetic engineering technique, and the like. It can be used for producing an Aβ polymerization inhibition antibody (or an antibody fragment).

The nucleic acid of the present invention can be prepared in an isolated state with reference to sequence information disclosed in the specification or attached sequence list, by using a genetic engineering technique, a molecular biological technique, a chemical technique, and the like. For example, it is possible to isolate a specific nucleic acid by using a hybridization method using an entire or a part of the complimentary sequence as a probe. Furthermore, by using a nucleic acid amplification reaction (for example, PCR) using a synthesized oligonucleotide primer designed to be specifically hybridized to a part of the base sequence, amplification and isolation can be carried out. Note here that an oligonucleotide primer can be generally synthesized easily by using a commercially available automated DNA synthesizer and the like.

A further aspect of the present invention relates to a vector containing the nucleic acid of the present invention. The term "vector," as used in this specification, is intended to refer to a nucleic acid molecule capable of transporting another nucleic acid which is inserted into the vector to the inside of the target such as cells. Examples of the vector includes a plasmid vector, a cosmid vector, a phage vector, a viral vector (e.g. an adenovirus vector, an adeno-associated virus vector, a retrovirus vector, a herpes virus vector).

In accordance with the purpose of use (cloning, protein expression), and by considering the kinds of host cells, an appropriate vector is selected. Examples of a vector to be used include a vector using *Escherichia coli* as a host (M13 phage or the modified body thereof, λ phage or the modified body thereof, pBR322 or the modified body thereof (pB325, pAT153, pUC8, etc.) and the like), a vector using yeast as a host (pYepSec1, pMFa, pYES2, etc.), a vector using insect cells as a host (pAc, pVL, etc.), a vector using mammalian cells as a host (pCDM8, pMT2PC, etc.).

The vector of the present invention is preferably an expression vector. The term "expression vector" is a vector capable of introducing the nucleic acid inserted therein into the target cells (host cells) and expressing in the cells. The expression vector usually includes a promoter sequence necessary for expression of the inserted nucleic acid and an enhancer sequence for promoting the expression, and the like. An expression vector including a selection marker can be used. When such an expression vector is used, by using a selection marker, the presence or absence of the introduction of an expression vector (and the degree thereof) can be confirmed.

Insertion of the nucleic acid of the present invention into a vector, insertion of the selection marker gene (if necessary), and insertion of a promoter (if necessary), and the like, can be carried out by a standard recombination DNA technology (see, for example, Molecular Cloning, Third Edition, 1.84, Cold Spring Harbor Laboratory Press, New York, a well-known method using restriction enzyme and DNA ligase).

Specifically, for example, the nucleic acid of the present invention is incorporated into an expression vector and by using this vector, a host cell can be transformed. Furthermore, in the nucleic acids of the present invention, nucleic acid encoding an antibody H chain (or H chain variable region) is incorporated into one vector while nucleic acid encoding an antibody L chain (or L variable region) is incorporated into another vector. By using the obtained two expression vectors, a host cell can be co-transformed. Furthermore, in the nucleic acids of the present invention, DNA encoding the nucleic acid encoding an antibody H chain (or an H chain variable region) and nucleic acid encoding an antibody L chain (or an L chain variable region) is incorporated into one vector and by using this vector, host cells can be transformed.

Examples of the host cell include a mammalian (such as human, monkey, mouse, rat, and the like) cell (a COS cell, a CHO cell, and the like), a bacterial cell such as *Escherichia coli*, a yeast cell, an insect cell, and the like.

Another aspect of the present invention relates to a host cell (that is, transformant) into which the nucleic acid of the present invention has been introduced. The transformant of the present invention can be preferably obtained by transfection or transformation using a vector of the above-mentioned present invention. The transfection and the like can be carried out by a calcium phosphate coprecipitation method, electroporation (Potter, H. et al., Proc. Natl. Acad. Sci. U.S.A. 81, 7161-7165 (1984)), lipofection (Felgner, P. L. et al., Proc. Natl. Acad. Sci. U.S.A. 84, 7413-7417 (1984)), microinjection (Graessmann, M. & Graessmann, A., Proc. Natl. Acad. Sci. U.S.A. 73, 366-370 (1976)), and the like.

The transformant of the present invention can be used for producing the antibody of the present invention or the antibody fragment of the present invention. That is to say, another aspect of the present invention provides a production method of the antibody and the like of the present invention using the above-mentioned transformant. The production method of the present invention includes at least a step of culturing the transformant under conditions in which the antibody and the like of the present invention is produced. In general, in addition to this step, a step for recovering (separating and purifying) the produced antibodies and the like is carried out. The target antibodies can be recovered from the inside of cells of the transformant or a culture solution by an appropriate combination of centrifugation, ammonium sulfate fractionation, salting out, ultrafiltration, an affinity chromatography, an ion exchange chromatography, and a gel filtration chromatography.

The transformant can be obtained by not for the purpose of producing the antibody and the like of the present invention but for the purpose of examining the behavior when for example, the antibody of the present invention is expressed in specific cells, or for the purpose of expressing the antibody of the present invention in specific cells (for example, for the purpose of treatment). Furthermore, transformant can be obtained for the purpose of producing a transgenic animal (not including human). That is to say, the transformant of the present invention can be used for producing a non-human transgenic animal. For example, as the transformant, a fertilized oocyte or an embryonic stem cell into which a nucleic acid encoding protein of the present invention is produced. From such transformants, a transgenic animal can be generated. The transgenic animal can be produced by using a microinjection method in which DNA is directly injected into the pronuclei of a fertilized egg, a method of using a retrovirus vector, a method of using an ES cell, and the like. Hereinafter, as an example of the production method of a transgenic animal, a method using the microinjection method is described.

In the microinjection method, firstly, a fertilized egg is collected from the oviduct of female mouse that is confirmed to have been mated, and the fertilized egg is cultured. Thereafter, a DNA construct (DNA encoding protein and the like of the present invention) is injected into the pronuclei of the fertilized oocyte. It is preferable that the DNA construct to be used includes a promoter sequence capable of efficiently expressing a transgene. Examples of such a promoter include a chicken β-actin promoter, a prion protein promoter, a human AR promoter, a neurofilament L chain promoter, an L7 promoter, a cytomegalovirus promoter, and the like. The fertilized egg that has finished an infusion operation is transplanted into the oviduct of a pseudopregnant mouse and the mouse that has undergone transplantation is fed for a predetermined time so as to obtain a baby mouse (F0). In order to confirm that the chromosome of the baby mouse includes a transgene appropriately, DNA is extracted from, for example, the tail of the baby mouse and the DNA is subjected to a PCR method using a primer specific to the transgene or a dot hybridization method using a probe.

The species of the "transgenic animal" in this specification is not particularly limited. However, it is preferably a mammalian, and more preferably a rodent such as a mouse, a rat, and the like.

By using the antibody of the present invention (including an antibody fragment), a screening method of a compound having an activity bound to a GAβ complex can be configured. The present invention provides a screening method of a compound having a binding activity to a GAβ complex. The screening method includes the following steps.

i) a step of selecting a first compound bound to the antibody or the antibody fragment of the present invention; and ii) a step of selecting a second compound bound to the first compound. Also in this screening method, by including a step of confirming the suppressing the amyloid fibril formation, it is possible to confirm that a compound selected by the screening method has a binding property with respect to the GAβ complex and an activity for suppressing the amyloid fibril formation.

In the step i), the binding property between the antibody or the antibody fragment and the sample and the first compound having the binding property is selected. The sample herein includes natural protein, natural peptide, natural high molecular compound, and the like, extracted from plants, animals and bacteria, as well as synthesized protein, synthesized peptide, synthesized high molecular compound, synthesized low molecular compound, antibodies (including the antibody of the present invention), a cell extract, a culture supernatant, and the like.

In the step i), the antibody to be used is solidified in a solid phase and the sample is brought into contact with this. On the contrary, the sample may be solidified in a solid phase.

By labeling the antibody to be used in advance, the selection (detection) can be facilitated and the selection (detection) efficiency can be improved. For labeling, a radioactive substance such as $^{125}$I, enzymes such as peroxidase, β-D-galactosidase, and the like, can be used. Furthermore, by using a secondary antibody recognizing the antibody to be used, the selection (detection) efficiency can be improved.

The antibody of the present invention (including an antibody fragment) can be used for a method for screening a compound bound to the Aβ polymerization inhibition antibody. That is to say, a method for screening a compound bound to the Aβ polymerization inhibition antibody including the following steps A) and B) can be configured.

A) a step of bringing a sample into contact with the antibody of the present invention; and B) a step of recovering a compound bound to the antibody.

The sample herein includes natural protein, natural peptide, natural high molecular compound, and the like extracted from plants, animals and bacteria, as well as synthesized protein, synthesized peptide, synthesized high molecular compound, synthesized low molecular compound, antibodies (including the antibody of the present invention), a cell extract, a culture supernatant, and the like.

Furthermore, a method for screening a compound bound to the Aβ polymerization inhibition antibody can be configured. The method includes the following steps:

C) a step of predicting a three-dimensional conformation of a variable region of the antibody of the present invention, and D) a step of selecting a compound having a three-dimensional conformation complimentary to the above-mentioned three-dimensional conformation.

The three-dimensional conformation of the antibody variable region can be predicted by a method such as an NMR (nuclear magnetic resonance) method (Wuthrich, K.: NMR of Protein and Nucleic Acids, John Wiley & Sons, New York, 1986), X-ray crystal structure analysis (Blundell, T. L. and John, L. N.: Protein Crystallography, Academic Press, Oxford, pp. 1-565, 1976, McPherson, A.: Preparation and Analysis of Protein Crystals, John Wiley & Sons, New York, pp. 1-371, 1982, Masaki Matsushima et al.: Protein Engineering Research Method, chapter 7, Analysis of Three-dimensional conformation, Hirokawa Shoten, Tokyo, 160-200, 1990), and the like.

The candidate compound in the step D) include natural protein, natural peptide, natural high molecular compound, and the like, extracted from plants, animals and bacteria, as well as synthesized protein, synthesized peptide, synthesized high molecular compound, synthesized low molecular compound, antibodies, and the like.

Since the compound obtained by the above-mentioned screening method has a binding activity with respect to the Aβ polymerization inhibition antibody, it is thought that production of the Aβ polymerization inhibition antibody is induced if the antibody is administered to the living body. That is to say, the Aβ polymerization inhibition antibody can be produced by acting on the immune defense mechanism of the living body. As a result, it is thought amyloid fibril formation when Aβ is polymerized to a GAβ complex formed in the living body can be suppressed by the effect of the antibody. Therefore, it is thought that Alzheimer's disease can be prevented or treated by using this compound. In other words, by using the compound, a method of preventing and treating Alzheimer's disease is provided. Furthermore, a drug, that is, vaccine or treatment agent, for Alzheimer's disease, which contains the compound as an effective component can be formed. On the other hand, since the synthetic lipid membrane of the present invention is also recognized by the Aβ polymerization inhibition antibody, when this is administered to the living body, it is thought that an effect of inducing production of the Aβ polymerization inhibition antibody can be exhibited. Therefore, it can be said that the synthetic lipid membrane can be used for producing the antibody having an inhibitory activity to the amyloid fibril formation in the human living body. Therefore, the present invention further provides Alzheimer prevention vaccine or treatment composition including the synthetic lipid membrane (lipid membrane including GM1).

When the antibody of the present invention is used for a drug, other pharmaceutically acceptable components (for example, physiological saline solution, vehicle, preservatives) can be contained. Furthermore, it can be formulated into various forms. For example, it can be formulated as capsules, syrup, tablets, granule, and the like, and can be administered by oral administration, parenteral administration (intravenous, intraarterial, subcutaneous, intramuscular, intraperitoneal injection, and the like).

The dosage amount is different depending upon the symptoms, the age, body weight of a patient, and the like. A person skilled in the art will be able to select and set an appropriate dosage.

EXAMPLES

1. Quantitative Binding of $A\beta_{1-40}$ and $A\beta_{1-42}$ to Liposome Including GM1 Ganglioside (GM1 Liposome)

1-1. Preparation Method of Aβ Solution

An Aβ solution is prepared by the following procedure. Firstly, synthetic $A\beta_{1-40}$ (for example, Lot. 501001 (PEPTIDE INSTITUTE INC., Osaka, Japan) or Lot. 519599 (Bachem AG, Switzerland) is dissolved in 0.002% ammonia solution to bring it to 500 μM and then centrifuged at 100,000 rpm for three hours (TLA120.0 Rotor, Optima TL, BECKMAN, California, USA). The upper two-thirds of the supernatant is collected and the concentration of Aβ is determined. The Aβ solution is divided into some aliquotes and stored at −80° C. until use. Immediately before use, the stored Aβ solution is dissolved and diluted to an appropriate concentration with a physiological Tris buffer solution (TBS: 150 mM NaCl and 10 mM Tris-HCl, pH 7.4).

According to this method, it is possible to centrifuge the seed of amyloid fibril formation from an Aβ solution prepared from the commercially available Aβ. In the Aβ fibril formation measurement using Thioflavin T, the present inventors have observed and clarified that in the Aβ fibril formation of $A\beta_{1-40}$ and $A\beta_{1-42}$ at the time of incubation at 37° C., the increase in the fluorescence intensity is not observed for at least 96 hours and 6 hours (J. Neurosci., 2004, 24: 4894-4902). The characteristic of this preparation method is important for measuring the seed activity in the Aβ fibril formation.

1-2. Preparation Method of Synthetic Lipid Including GM1 Ganglioside (GM1 Liposome Solution)

Synthetic lipid including GM1 ganglioside is prepared by the following procedure. Firstly, cholesterol, sphingomyelin (SIGMA-ALDRICH, St. Louis, Mo., USA) and GM1 (Wako Pure Chemical Industries, Osaka, Japan) are dissolved in a chloroform/methanol mixed solution (1:1) at a predetermined ratio (for example, 2:2:1). This mixed solution is dried under a stream of nitrogen gas for one hour and stored at −40° C. until use. Immediately before use, the dried mixture of lipids is resuspended in TBS such that the GM1 concentration is 2.5 mM, and subjected to 10 cycles of freezing/thawing using liquid nitrogen. This lipid suspension is centrifuged at 13,000 rpm for 15 minutes (MX-160, TOMY, Tokyo, Japan) and precipitates are resuspended in TBS such that the GM1 concentration becomes the same concentration again. Finally, this suspension is sonicated on ice for five minutes, repeated three times, by using Ultrasonic Disrupter (UD-201, output level 2, TOMY, Tokyo, Japan) equipped with Microchip (TP-030 TOMY, Tokyo, Japan) for five minutes. The obtained solution is defined as a GM1 liposome solution.

1-3. Reaction of GM1 Liposome Solution and Aβ

A GM1 liposome solution and an Aβ solution are mixed, stirred by voltex for one minute and dispersed in water. The mixture is centrifuged at 100000×g for ten minutes, and then a supernatant is sucked. One ml of Tris buffer solution (10 mM Tris-HCl buffer pH7.4/150 mM NaCl) is added to the precipitate and sufficiently stirred to be dispersed in water.

1-4. Binding Assay of Aβ to GM1 Liposome

By using radioactive iodine ($^{125}I$) labeled $A\beta_{1-40}$ (Amersham, PHARMACIA, IM-2394, 370 KBq), a binding amount of Aβ to GM1-containing liposome (GM1 liposome) was measured (FIG. 1).

Firstly, in accordance with the method described in 1-2., GM1 liposome solutions having component ratios shown in Table 2 are prepared, respectively. Note here that each GM1 liposome solution was prepared so that the total concentration of the components (that is, liposome concentration) was 4600 μM. On the other hand, to the Aβ solution prepared by the method of 1-1, 100 nCi of radioactive Aβ that had similarly been treated by ultracentrifugation (at 100000 rpm for two hours at 4° C.) was mixed. Thus, 100 μl of solution with Aβ concentration of 46 μM was prepared. To this Aβ solution, 100 μl each of the above-mentioned GM1 liposome solutions was added and incubated at 37° C. for one minute. Subsequently, 1 ml of Tris buffer solution (10 mM Tris-HCl buffer pH7.4/150 mM NaCl) was added and centrifuged so as to precipitate. This procedure was repeated four times, and then Aβ that had not been bound to GM1 liposome was washed and removed. The amount of precipitated radioactive material was calculated, and thereby the amount of Aβ bound to GM1 liposome was measured (FIG. 1).

Figure 2:
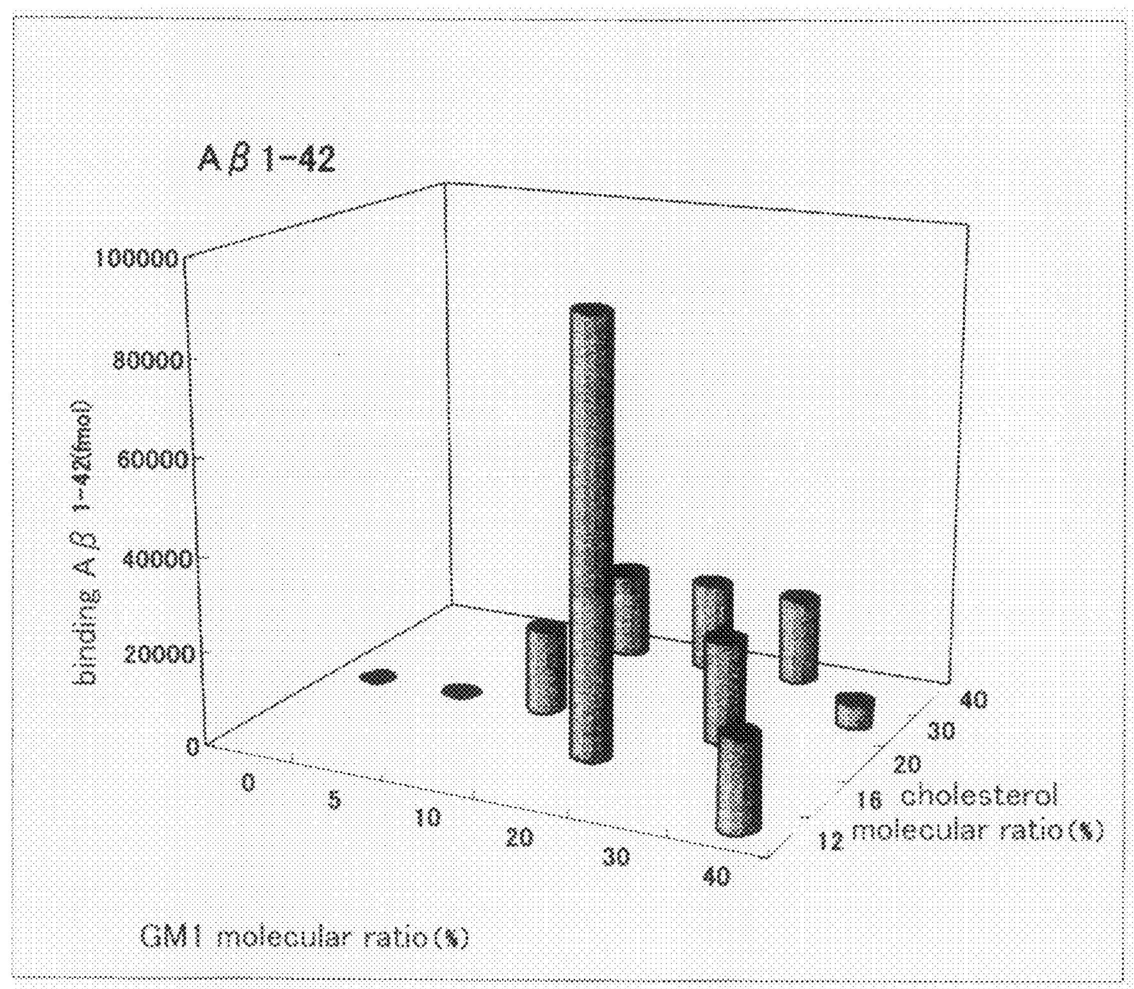
FIG. 2 is a graph showing measurement results of a binding amount of $^{125}$I-labeled amyloid β protein (1-42) to GM1-containing liposome measured while changing the molar ratio of GM1 to cholesterol in lipid constituting the liposome. The amount of amyloid β protein (1-42) bound to the liposome having 10-40% GM1 composition is large. In particular, the binding amount becomes maximum when the ratio (molecular ratio) of sphingomyelin: cholesterol: GM1 is 64:16:20.

Similarly, by using radioactive iodine ($^{125}I$) labeled $A\beta_{1-42}$ (Amyloid β-Protein (Human, 1-42), code 4349-v, PEPTIDE INSTITUTE INC., Osaka), a binding amount of Aβ to GM1-containing liposome (GM1 liposome) was measured (FIG. 2). That is to say, to an $A\beta_{1-42}$ solution prepared by the same method as the method described in 1-1, radioactive iodine ($^{125}I$) labeled $A\beta_{1-42}$ (Amersham, PHARMACIA, IM-2394, 370 KBq) that had similarly been treated by ultracentrifugation (at 100000 rpm for two hours at 4° C.) was mixed. The binding amount of $A\beta_{1-42}$ to GM1 liposome was measured (FIG. 2).

The above-mentioned results show that the liposome containing 10-40% (molecular ratio) of GM1 has the Aβ polymerization initiating activity of both $A\beta_{1-40}$ and $A\beta_{1-42}$. When the case where $A\beta_{1-40}$ is used and the case where $A\beta_{1-42}$ is used were compared with each other, in both cases, the binding amount to liposome changes depending upon the liposome composition but there is no substantial difference of the binding amount between them (FIGS. 1 and 2). In the examined range, the GM1 molecular ratio particularly effective to the polymerization initiation was 20% (FIGS. 1 and 2). The GM1 liposome Aβ complex (synthesized GAβ) formed by reacting the GM1 liposome that was produced at this concentration for a short time (one minute) is used in each of the following experiments as an immunogen or a screening antigen.

2. Production of Anti-Aβ Monoclonal Antibody by Immunization with Aβ Proteoliposome 2-1. Immunization of Mouse with GAβ Prepared In Vitro In order to obtain a monoclonal antibody having a polymerization inhibitory activity, an immunogen (synthesized GAβ) was produced under the optimum conditions (liposome having a component ratio (molecular ratio) of sphingomyelin: cholesterol: GM1=64:16:20 is brought into contact with Aβ for one minute) in which the amount of GAβ formation was maximum from the result of 1. This synthesized GAβ (100 μl each for one immunization) was administered to the peritoneal cavity of a mouse (Balb/c) several times every other week so as to immunize the mouse. At the next week after the fifth immunization, the blood is collected from the ocular fundus of the mouse so as to confirm the antibody titer. The spleen of a mouse with high antibody titer was taken out and cell fusion was carried out by the following procedure.

2-2. Cell Fusion and Selection of Hybridoma

The extracted spleen cells of the mouse and myeloma cells Sp2/0-Ag14 of the same system of mouse were mixed at the ratio of about 10:1 and cells were fused by using 50% Polyethylene glycol 4000 as a fusion accelerating agent so as to produce a hybridoma. Cells after fusion were suspended in a HAT medium (a medium including hypoxanthine, aminopterin, and thymidine) containing 10% bovine serum so that the concentration became $1\times10^6$ cells/ml. The obtained cell suspension was dispensed into a 96-well microtiter plate (Nunc, Maxisoap, the same is true hereinafter) in the amount of 50 μl each for one well.

Fused cells were cultured in $CO_2$ incubator (5% $CO_2$, at 37° C.), the medium is replaced by a HAT medium and cells were proliferated. Thus screening of the fused cells of the spleen cells and myeloma cells was carried out. Then, it was acclimated in HT medium and further acclimated in 10% FCS (fetal bovine serum)-DMEM medium.

After HAT selection, the binding property of the antibody contained in the culture supernatant of the living hybridoma was detected by using a microtiter plate sensitized with synthetic GAβ by ELISA mentioned below. Thus, screening was carried out by using the binding property as an index.

2-3. Primary Screening of Fused Cell Clone by ELISA Using GAβ-Bound Microplate

Firstly, GM1 was mixed with sphingomyelin and cholesterol and dissolved in chloroform ethanol (chloroform:ethanol=1:1). The solution was dispensed in a 96-well ELISA plate (made of polycarbonate) in an amount of 50 μl each, followed by drying at room temperature so as to form a lipid membrane (lipid film). This was blocked with 1% skim milk/PBS. Thereafter, 20 μg/ml of Aβ was added and reacted for a short time (one minute) so as to form GAS. After washing, 100 μL each of the culture supernatant of the hybridoma prepared as mentioned above was added to each well and incubated at room temperature for two hours. A liquid in the well was removed and then washed with PBS. Then, 100 μl/well of horseradish peroxidase (HRP) labeled goat anti-mouse IgG+IgM (H+L) antibody 3000-fold diluted with 0.1% TWEEN 20-TBS (Kirkegaard & Perry Laboratories, Inc.) was added to each well, and stood still at room temperature for one hour (secondary reaction), followed by washing with PBS. Thereafter, 100 μl/well of 750 μM TMB (Tetramethylbenzidine) solution was added to each well and allowed to develop color for 5 to 20 minutes at 30° C. (coloring reaction). The coloring reaction was stopped by adding 100 μl/well of 1.5 $NH_3PO_4$ to each well. Then, absorbance at 450 nm was measured by MPR A4i (TOSOH CORPORATION) by using a microtiter plate reader. A system into which Aβ is not added is prepared as a control. A well that is negative with respect to the control and shows negative reaction to a plate that is sensitized with free Aβ (20 μg/ml) and a lipid membrane (lipid film) is selected.

To the selected well, cloning by a limiting dilution technique is repeated twice so as to establish a fused cell clone. The obtained clone was subjected to selection (secondary screening) by using the following Aβ polymerization evaluation system.

3. Evaluation of Monoclonal Antibody by Three Kinds of In Vitro Aβ Polymerization Evaluation Systems By using three kinds of Aβ polymerization evaluation systems ((A) polymerization initiated by adding Aβ fibril fragment, (B) Aβ40 polymerization initiated from GAβ40, and (C) Aβ42 polymerization initiated from GAβ42) in vitro described in the report by the present inventors (J. Neurosci., 2004, 24: 4894-4902), the effect of the antibody produced by each cell clone obtained in the above-mentioned 2 on the Aβ polymerization reaction was observed. The used Aβ polymerization evaluation systems (Aβ polymerization inhibition tests A to C) will be shown hereinafter. Note here that as a positive control and a negative control, a 4396C antibody having a polymerization suppressing activity (International Publication No. 03/014162, J. Neurosci., 2004, 24: 4894-4902) and a 4G8 antibody (an antibody recognizing free Aβ) were used, respectively.

A. Aβ Polymerization Inhibition Test 1 (Inhibitory Effect on Polymerization Initiated by Adding Aβ Fibril)

A-1. Preparation of Aβ Solution

An Aβ solution is prepared by the same procedure as in the above-mentioned 1-1.

A-2. Preparation of Fibrous Aβ Solution

A fibrous Aβ solution is prepared by the following procedure. Firstly, synthetic $A\beta_{1-40}$ (for example, Lot. 501001 (PEPTIDE INSTITUTE INC., Osaka, Japan) or Lot. 519599 (Bachem AC, Switzerland) is dissolved in about 500 μM ammonia solution at 4° C. by vortex for a short time, and diluted to 50 μM with an incubation buffer (50 mM phosphate buffer solution, pH 7.5; 100 mM NaCl). The solution is incubated at 37° C. for 24 hours and the mixed solution is centrifuged at $1.6\times10^4$ g, at 4° C. for three hours. Precipitates are resuspended in an ice-cold incubation buffer containing 0.005% $NaN_3$ in an Eppendorf tube, and sonicated on ice by using an ultrasonic disintegrator (UD-201, TOMY, Tokyo, Japan) equipped with Microchip (TP-030, TOMY, Tokyo, Japan) and stored at 4° C. before use.

A-3. Evaluation of Inhibitory Effect (1) Fibrous Aβ solution (5 μl) and Aβ solution (100 μl) are mixed with each other and incubated at 37° C. in the presence of the subject antibody (test group, concentration of adding antibody: 1 μM) or in the absence of the subject antibody (control group).

(2) Aβ fibril formation is measured by using Thioflavin T according to Naiki H and Gejyo F (1999) Methods Enzymol 309, 305-318. Firstly, four hours after the start of incubation, a part of solution (5 μl) is sampled. To this, Thioflavin T (Sigma) is added so that the final concentration is 5 μM. After dilution with 1 ml of 50 mM glycine-sodium hydroxide buffer, the fluorescence intensity (excitation wavelength: 446 nm, fluorescence wavelength: 490 nm) of Aβ fibril is measured by using a fluorescence spectrophotometer (for example, RF-5300PC, Shimadzu).

(3) The inhibitory effect (inhibitory activity) of the subject antibody is calculated from the following calculation equation.

inhibitory effect(%)=(fluorescence intensity of control group−fluorescence intensity of test group)/fluorescence intensity of control group×100

B. Aβ Polymerization Inhibition Test 2 (Inhibitory Effect on Aβ40 Polymerization Initiated from GAβ40)

B-1. Preparation of Aβ Solution

Aβ solution is prepared by the same procedure as in 1-1. described above.

B-2. Preparation of Synthetic Lipid Containing GM1 Ganglioside

A synthetic lipid containing GM1 ganglioside is prepared by the same procedure as in 1-2. described above.

B-3. Evaluation of Inhibitory Effect (1) Synthetic lipid containing GM1 ganglioside and Aβ solution are mixed with each other and incubated at 37° C. in the presence of the subject antibody (test group, concentration of adding antibody: 1 μM) or in the absence of the subject antibody (control group).

(2) Aβ fibril formation is measured by using Thioflavin T according to Naiki H and Gejyo F (1999) Methods Enzymol 309, 305-318. Firstly, 20 hours after the start of incubation, a part of the solution (5 μl) is sampled. To this, Thioflavin T (Sigma) is added so that the final concentration is 5 μM. After dilution with 1 ml of 50 mM glycine-sodium hydroxide buffer, the fluorescence intensity (excitation wavelength: 446 nm, fluorescence wavelength: 490 nm) of Aβ fibril is measured by using a fluorescence spectrophotometer (for example, RF-5300PC, Shimadzu).

(3) The inhibitory effect (inhibitory activity) of the subject antibody is calculated from the following calculation equation.

inhibitory effect(%)=(fluorescence intensity of control group−fluorescence intensity of test group)/fluorescence intensity of control group×100

Note here that the lipid membrane containing GM1 ganglioside is usually used in a state which is bound to an insoluble support such as beads, microplate made of resin such as polystyrene, polycarbonate resin, silicon resin, nylon resin, etc., and glass and the like.

C. Aβ Polymerization Inhibition Test 2 (Inhibitory Effect on Aβ42 Polymerization Initiated from GAβ42)

Aβ solution is prepared according to the above-mentioned procedure 1-1. by using synthetic $A\beta_{1-42}$ (for example, Amyloid β-Protein (Human, 1-42), code 4349-v, PEPTIDE INSTITUTE INC., Osaka) instead of $A\beta_{1-40}$. On the other hand, synthetic lipid containing GM1 ganglioside is prepared according to the above-mentioned procedure 1-2. By using these two solutions, the inhibitory effect is evaluated by the same procedure as mentioned in B-3.

As a result of the Aβ polymerization inhibition test, antibodies having a high Aβ polymerization inhibitory effect, clones 1C9, 2E12, 3G11 and 4E11 were selected (secondary selection). The Aβ polymerization inhibitory effect of each clone is shown in Table of FIG. 4. The clone 1C9 strongly inhibits the polymerization initiated by adding Aβ fibril but the inhibitory activity on the Aβ40 polymerization initiated from GAβ and Aβ42 polymerization initiated from GAβ is weak. Furthermore, in the clones 2E12 and 3G11, strong inhibitory activity on three kinds of polymerization systems is observed. These clones show stronger activity with respect to Aβ40 polymerization initiated from GAβ and Aβ42 polymerization initiated from GAβ. On the other hand, in the clone 4E11, equal level of inhibitory activity on three kinds of polymerization systems can be observed.

Note here that a 4G8 antibody as a negative control is an antibody recognizing free Aβ. However, in this inhibition test, no inhibitory activity is observed. On the contrary, a 4396C antibody as a positive control shows an Aβ polymerization inhibitory effect in any of the polymerization systems. It has a feature that stronger inhibitory activity is shown in (A) polymerization initiated by adding Aβ fibril fragment rather than in (B) Aβ40 polymerization initiated from GAβ40, and (C) Aβ42 polymerization initiated from GAβ42.

4. Analysis of Inhibition Effect of Clones 2E12 and 3G11 Antibodies on AβPolymerization In Vitro The clones 2E12 and 3G11 show an inhibitory activity in three kinds of polymerization evaluation systems ((A) polymerization initiated by adding Aβ fibril fragment, (B) Aβ40 polymerization initiated from GAβ40, and (C) Aβ42 polymerization initiated from GAβ42), in particular, as compared with the 4396C antibody, they show stronger activity in the Aβ40 polymerization initiated from GAβ40 and the Aβ42 polymerization initiated from GAβ42 (above-mentioned 3). In order to examine the molecular mechanism of this inhibitory activity, the Aβ40 polymerization initiated from GAβ40 is inhibited by these antibodies and Aβ fibril formation was monitored over time. As a negative control, 4396C antibody was used. The antibody concentration was set to 2 μM. All the reaction temperatures of the fibril formation in this analysis were set to 37° C.

Figure 5:
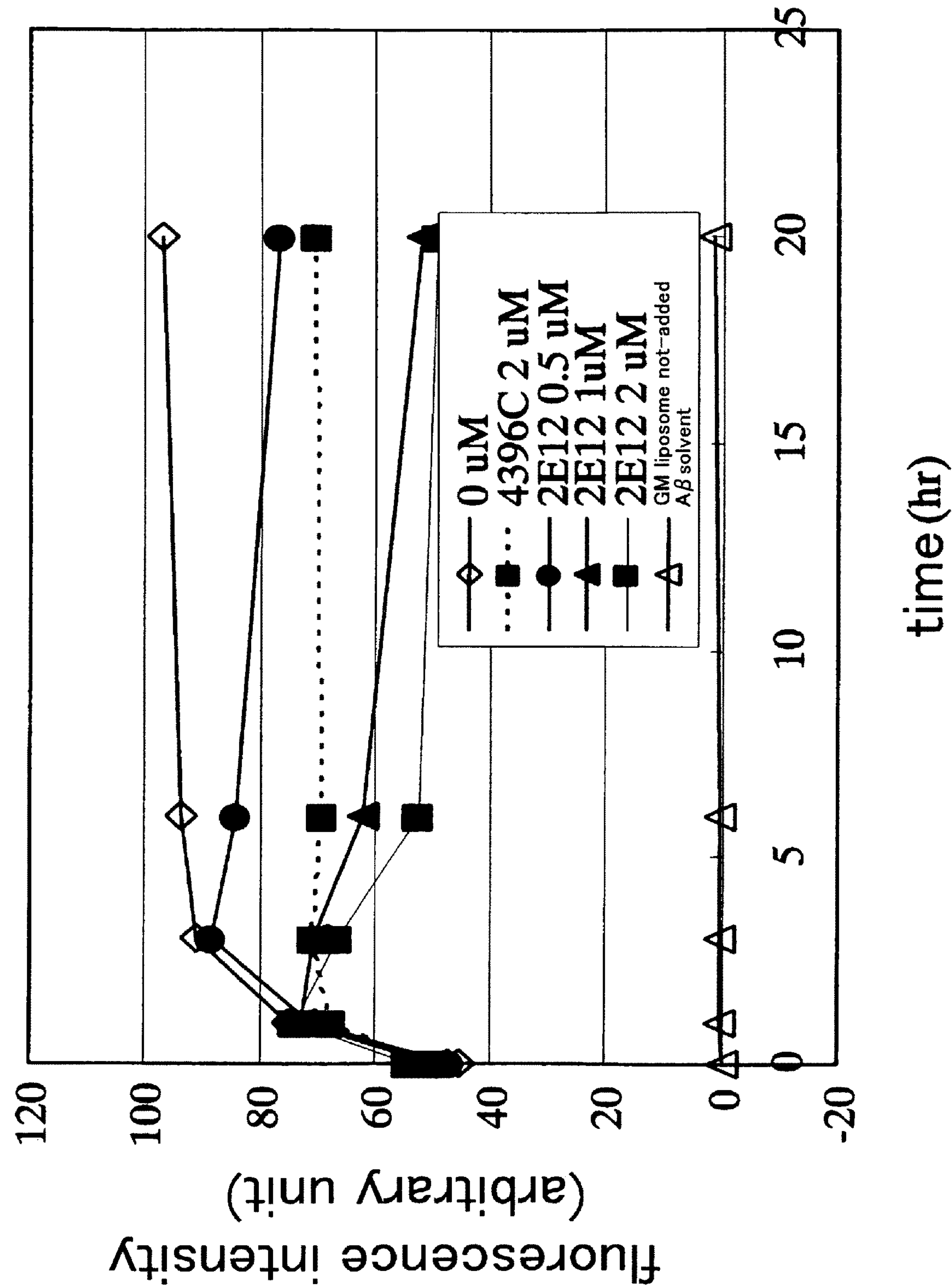
FIG. 5 shows the results of measuring an amyloid β protein depolymerization activity of the obtained antibody 2E12. GAβ is added to the antibody 2E12 and at the same time the antibody is added into Aβ40 solution. The fibril formation of Aβ40 using Thioflavin T is measured over time. The measurement value is observed to be clearly lowered with the addition of 2E12.

FIG. 5 shows the measurement results when 2E12 is added (the measurement results of fibril formation of Aβ40 using Thioflavin T). In the Aβ solution without adding GM1 liposome, the increase in the fluorescence intensity was not observed for 20 hours. Addition of antibody was carried out concurrently with addition of GM1 liposome and a small amount of samples were taken out over time. Thioflavin T solution was mixed with this sample and the fluorescence intensity was measured. Since GM1 liposome has autofluorescence, with the addition thereof, the fluorescence intensity of the reaction system is increased. In a system in which an antibody had not been added, the fluorescence intensity started to increase from the time of addition, and continued to increase until four hours had passed. Thereafter, the fluorescence intensity maintained a constant value until 20 hours had passed. This result is interpreted as follows. GAβ40 was formed with the addition of GM1 liposome, then Aβ40 fibril formation progressed over time and fibril elongated. Aβ in the solution was consumed by the fibril formation, the concentration was reduced and became not more than the critical concentration of the fibril formation. In the addition system of 2 μM of 4396C antibody as a positive control, the increase of the fluorescence intensity stopped after two hours had passed, which was earlier than that of the non-addition system. The fluorescence intensity was maintained until 20 hours had passed. This result is interpreted that the Aβ fibril formation stops with this antibody and that the fibril elongation is suppressed thereafter. On the other hand, in the case of 2E12, the increase of the fluorescence intensity stopped when four hours had passed when the addition concentration was 0.5 μM and stopped when two hours had passed when the addition concentration was 1 μM or 2 μM. Thereafter, the fluorescence intensity was reduced at the rate depending upon the antibody concentration. From this result, 2E12 does not affect the Aβ fluorescence intensity initiated from GAβ40 at the start of fibril formation, but 2E12 determines the length of the Aβ fibril after the fibril elongation proceeds. It is thought that 2E12 has an effect of allowing the balance relation between the fibril elongation by the Aβ polymerization reaction and the fibril shortening by the Aβ depolymerization to tilt toward the fibril shortening.

Figure 6:
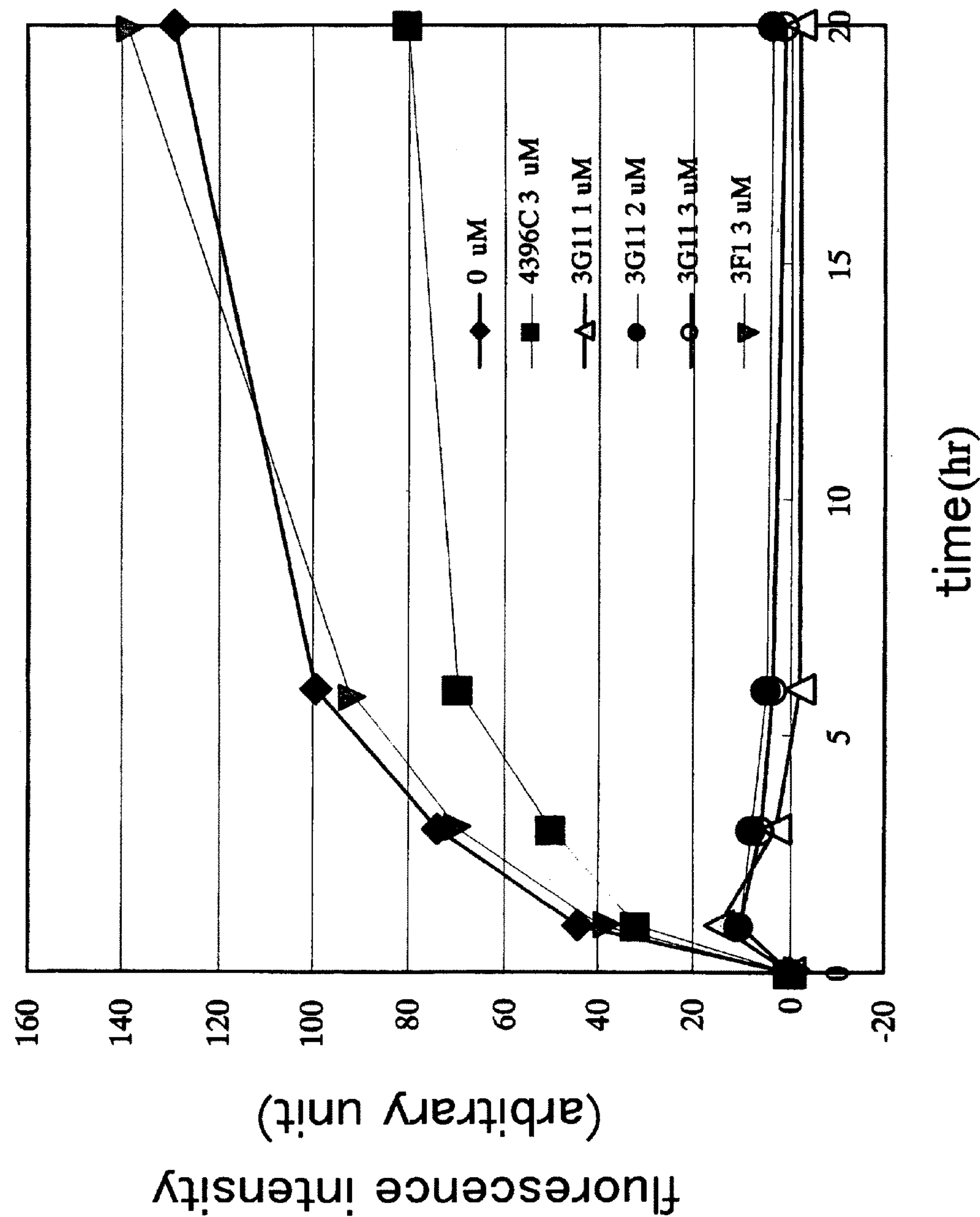
FIG. 6 shows the results of measuring an amyloid β protein depolymerization activity of the obtained antibody 3G11. GAβ is added to the antibody 3G11 concurrently with the addition of the antibody to the Aβ40 solution. The fibril formation of Aβ40 using Thioflavin T is measured over time. It is observed that the measurement value is clearly lowered with the addition of 3G11.

FIG. 6 shows the measurement results when 3G11 is added (the measurement results of fibril formation of Aβ40 using Thioflavin T). The result shown in FIG. 6, unlike the result shown in FIG. 5, plots the values obtained by subtracting the value of fluorescence intensity immediately after GM1 liposome from all the measurement values. In the Aβ solution without adding an antibody, the fluorescence intensity was rapidly increased when GM1 liposome was added and the fluorescence intensity was continued to increase with the increasing rate being reduced until 20 hours had passed. When 4396C antibody was added, the fluorescence intensity value was lower as compared with the case where it was not added and the increase in the fluorescence intensity was observed until six hours had passed. 3F1 used as a negative control is an antibody recognizing C terminal of free Aβ40 peptide. The change of the fluorescence intensity when this antibody was added was the same as the case where it was not added. This result shows that this antibody does not affect the Aβ fibril formation. When the 3G11 antibody is added, at any addition concentration (1, 2 and 3 μM), although the fluorescence intensity increases for one hour of the reaction initiation time, thereafter, the fluorescence intensity is reduced and finally it become an equal level as that of the addition time of GM1 liposome. From the result, similar to 2E12, 3G11 does not affect at the start of Aβ fibril formation initiated from GAβ40, but 3G11 determines the length of the Aβ fibril after the fibril elongation proceeds. It is thought that 3G11 has an effect of allowing the balance relation between the fibril elongation by the Aβ polymerization reaction and the fibril shortening by the Aβ depolymerization to tilt toward the fibril shortening.

Figure 7:
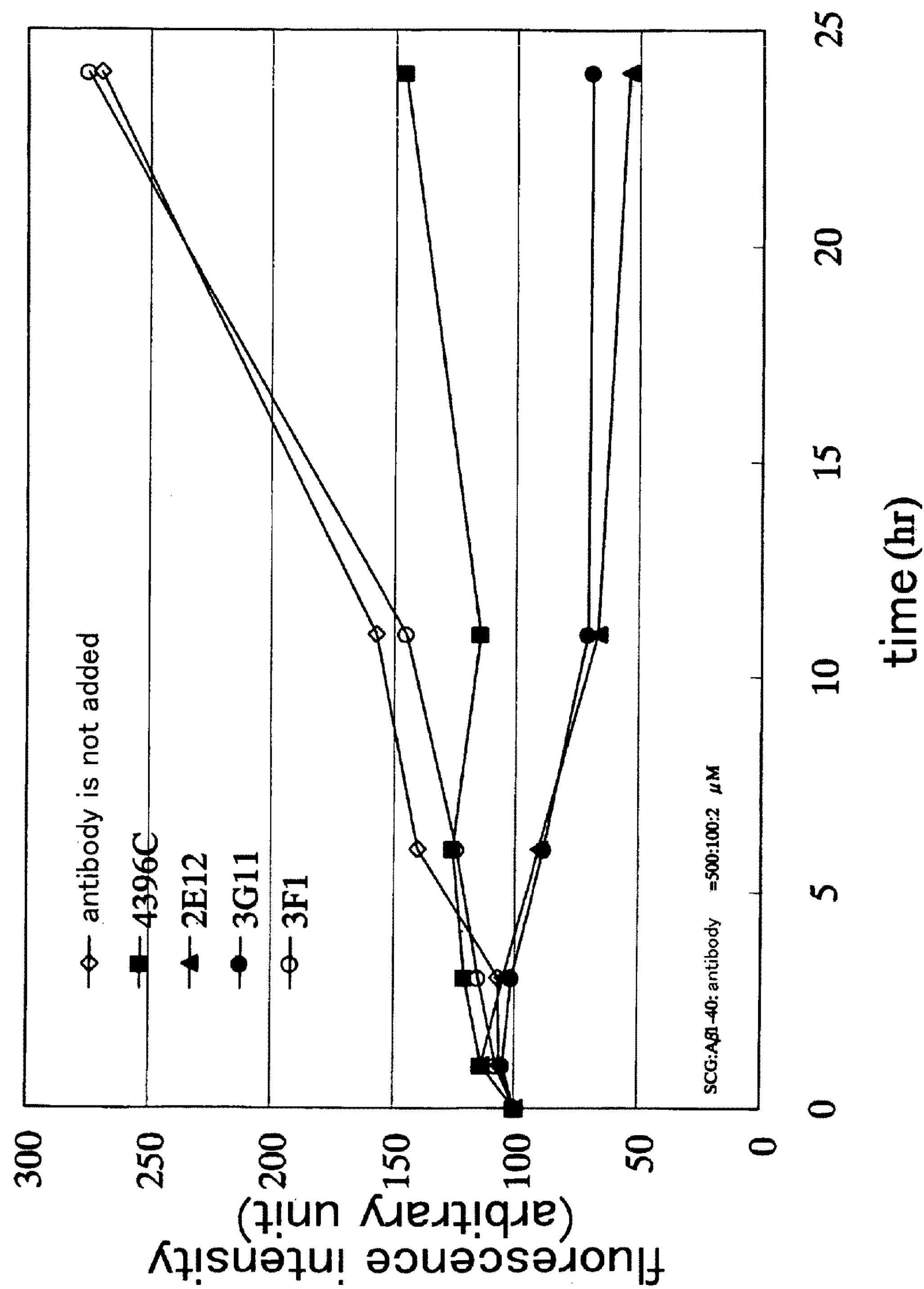
FIG. 7 shows the effect of antibodies 2E12 and 3G11 on Aβ fibril polymerization. Four hours after GM1 liposome had been added, antibodies 2E12 and 3G11 were added. The results obtained by carrying out Thioflavin T fluorometry over time after the addition are shown in the graph. The measurement values are observed to be clearly lowered with the addition of 2E12 and 3G11. When 4396C as a positive control is added, suppression of the Aβ extension reaction is observed; and when 2E12 and 3G11 are added, the destruction effect of the Aβ fibril is observed.
Figure 8:
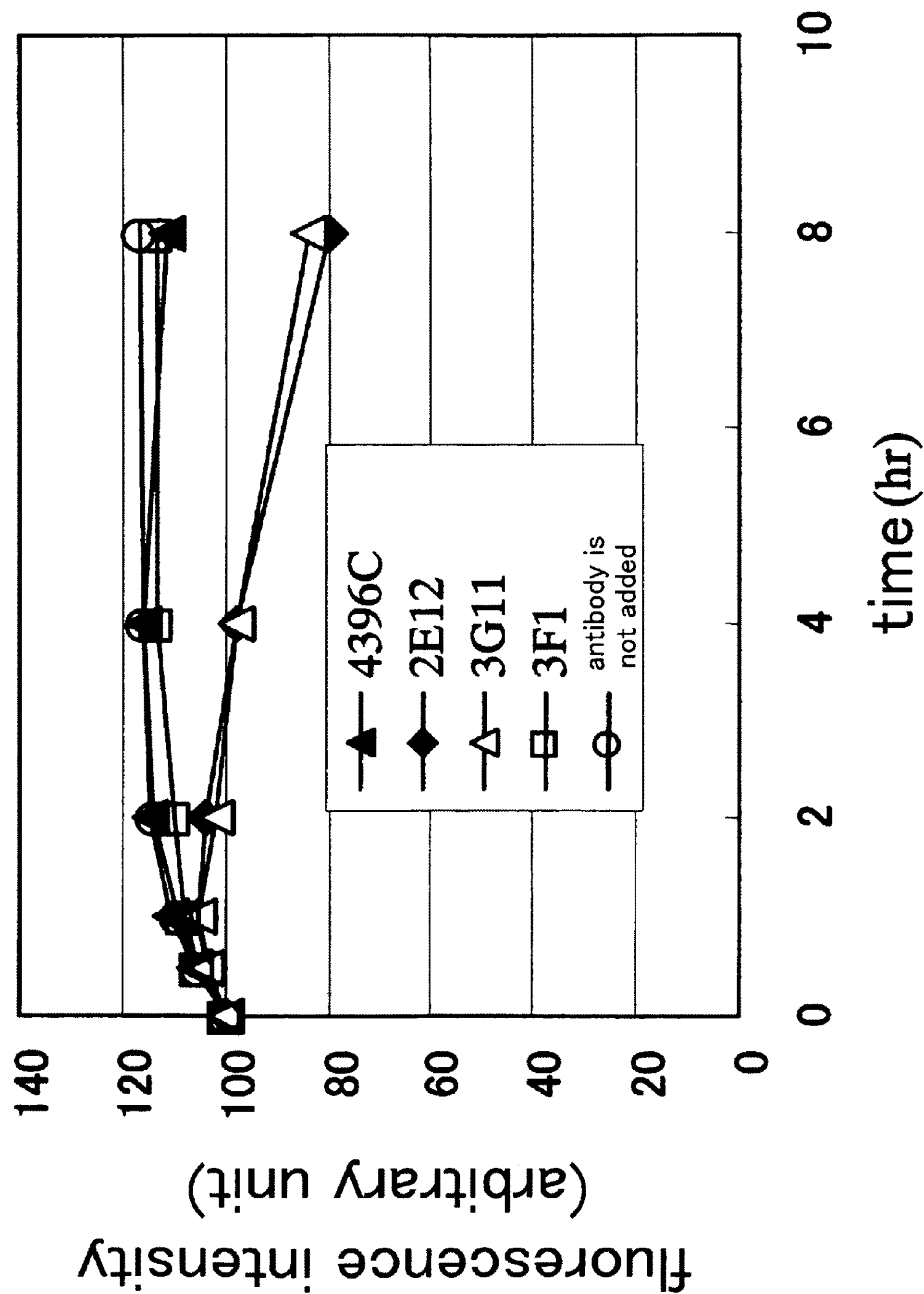
FIG. 8 shows the effect of antibodies 2E12 and 3G11 on Aβ fibril polymerization. Twenty-four hours after GM1 liposome had been added, antibodies 2E12 and 3G11 were added. After the addition, Thioflavin T fluorometry was carried out over time. The measurement values are observed to be clearly lowered with the addition of 2E12 and 3G1. When 2E12 and 3G11 are added, the destruction effect of the Aβ fibril is observed. This effect is not observed in 4396C used as a control.

Next, an experiment, in which an antibody is added four hours after the addition of GM1 liposome when it is thought to elongate Aβ fibril, was carried out (FIG. 7). The former experiment, the concentration of Aβ was set to 23 μM, but in this experiment, it was increased to 100 μM. The fluorescence intensity of the system in which antibody had not been added increased continuously for 24 hours after measurement started. The fluorescence intensity when 2 μM of 3F1 as a negative control had been added was the same level as the case where it had not been added and increased continuously for 24 hours after the measurement started. The fluorescence intensity in which 2 μM of 4396C had been added maintained substantially a constant value for 24 hours after the measurement started. In the case where 2E12 was added and the case where 3G11 was added, the fluorescence intensity was continuously reduced after the measurement started and became about 60% of that of the measurement starting time when 24 hours had passed. From these phenomena, it can be thought that 4396C suppresses new elongation of Aβ fibril. However, it is thought that 2E12 and 3G11, unlike 4396C, and promotes fragmentation of the formed Aβ fibril or depolymerization of Aβ fibril. Therefore, an antibody was added to a sample showing an approximately maximum value of Thioflavin T fluorometry value in the experiment and the fluorescence intensity was measured (FIG. 8). The Aβ concentration was set to 23 μM and a sample after 24 hours have passed after GM1 liposome was added was used. To this sample, 2 μM of antibody was added and Thioflavin T fluorometry was carried out over time. When the antibody is not added, the fluorescence intensity was gently increased for eight hours after the measurement started (about 10%). The fluorescence intensity when 2 μM of 3F1 was added was increased by about 10% for eight hours after the measurement started. This change was substantially the same as the case in which an antibody was not added. Furthermore, when 2 μM of 4396C was added, for eight hours after the measurement started, the same change of fluorescence intensity was shown as in the case where an antibody was not added and the case where 3F1 was added. In the case where 2E12 was added and the case where 3G11 was added, the same change of the fluorescence intensity is shown, showing that the fluorescence intensity was reduced by about 20% for eight hours after the measurement started. It is clear that 2E12 and 3G11 reduce Thioflavin T fluorometry value by fragmentation of Aβ fibril or depolymerization of Aβ fibril.

The above-mentioned results show that 4396C suppresses new elongation of Aβ while 2E12 and 3G11 have an activity for promoting fragmentation of Aβ fibril or depolymerization of Aβ fibril.

5. Isolation of VH and VL Genes 5-1. Amplification (PCR) of VH Gene

Primers at 5, terminal of the mouse VH (VH primers) were examined from the gene database and a sfiI site was added so as to design a primer. By mixing the equal amount of primers, a mix primer was formed.

VH Primers (as One Example)

```
Name: 5' terminal side →3' terminal side
[1] mVH1A:
act tac tcg cgg ccc agc cgg cca tgg ccg a(g/t)g tgc agc ttc agg agt cag g       (52 mer, SEQ ID NO: 65)

[2] mVH1B1:
act tac tcg cgg ccc agc cgg cca tgg ccc agg tgc agc tga agg agt cag g           (52 mer, SEQ ID NO: 66)

[3] mVH1B2:
act tac tcg cgg ccc agc cgg cca tgg ccc agg tgc agc tga agc agt cag g           (52 mer, SEQ ID NO: 67)

[4] mVH2A1:
act tac tcg cgg ccc agc cgg cca tgg ccg agg tcc agc tgc a(a/g)c a(a/g)t ctg g   (52 mer, SEQ ID NO: 68)

[5] mVH2A2:
act tac tcg cgg ccc agc cgg cca tgg ccg agg ttc agc tgc agc agt ctg g           (52 mer, SEQ ID NO: 69)
```

-continued

```
[6] mVH2B1:
act tac tcg cgg ccc agc cgg cca tgg ccc agg tcc aac tgc agc agc ctg g          (52 mer, SEQ ID NO: 70)

[7] mVH2B2:
act tac tcg cgg ccc agc cgg cca tgg ccc agg tcc acc tgc agc agt ctg g          (52 mer, SEQ ID NO: 71)

[8] mVH3A:
act tac tcg cgg ccc agc cgg cca tgg ccg agg tga agc tgg tgg a(a/g)t ctg g      (52 mer, SEQ ID NO: 72)

[9] mVH3B:
act tac tcg cgg ccc agc cgg cca tgg ccg agg tga agc ttc tgg agt ctg g          (52 mer, SEQ ID NO: 73)

[10] mVH3C1:
act tac tcg cgg ccc agc cgg cca tgg ccg aag tga agc ttg agg agt ctg g          (52 mer, SEQ ID NO: 74)

[11] mVH3C2:
act tac tcg cgg ccc agc cgg cca tgg ccg agg tga agc tgg atg aga ctg g          (52 mer, SEQ ID NO: 75)

[12] mVH3C3:
act tac tcg cgg ccc agc cgg cca tgg ccg aag tga agc tgg tgg agt ctg a          (52 mer, SEQ ID NO: 76)

[13] mVH3D1:
act tac tcg cgg ccc agc cgg cca tgg ccg aag tgc agc tgg tgg agt ctg g          (52 mer, SEQ ID NO: 77)

[14] mVH3D2:
act tac tcg cgg ccc agc cgg cca tgg ccg aag tga tgc tgg tgg agt ctg g          (52 mer SEQ ID NO: 78)

[15] mVH3D3:
act tac tcg cgg ccc agc cgg cca tgg ccg aag tga agc tgg tgg agt ctg g          (52 mer, SEQ ID NO: 79)

[16] mVH5A1:
act tac tcg cgg ccc agc cgg cca tgg ccg agg ttc agc ttc agc agt ctg g          (52 mer, SEQ ID NO: 80)

[17] mVH5A2:
act tac tcg cgg ccc agc cgg cca tgg ccc agg tcc agc tgc agc agt ctg g          (52 mer, SEQ ID NO: 81)
```

Note here that (a/g), (g/t) represent two bases mix.

Similarly, primers at 3' terminal (JH primers) were examined and XhoI site was added to a sequence of a complimentary chain so as to design a primer. By mixing the equal amount of primers, a mix primer was formed.

JH Primers (as One Example)

```
Name: 5' terminal side →3' terminal side
[1] mJH1Xho: cgt ttt ggc gct cga gac ggt gac cgt ggt ccc tgc g  (37 mer, SEQ ID NO: 82)

[2] mJH2Xho: cgt ttt ggc gct cga gac tgt gag agt ggt gcc ttg g  (37 mer, SEQ ID NO: 83)

[3] mJH3Xho: cgt ttt ggc gct cga gac agt gac cag agt ccc ttg g  (37 mer, SEQ ID NO: 84)

[4] mJH4Xho: cgt ttt ggc gct cga gac ggt gac tga ggt tcc ttg a  (37 mer, SEQ ID NO: 85)
```

As positive hybridoma cells selected as a result of the secondary screening (the above-mentioned 3) were cultured and cDNA was obtained in the usual manner. Next, the obtained cDNA was used as a template and PCR (30 cycles. Each cycle includes 94° C. for one minute, 65° C. for two minutes and 72° C. for one minute) was carried out by using 20 μl each of the above-mentioned primer VH Primers (200 μmol/μl) and JH Primers (200 μmol/μl) with LA Taq (TAKARA) in the presence of $MgCL_2$ and dNTPmix. Thus, VH gene was isolated.

5-2. Amplification (PCR) of VL Gene

Similar to the amplification of the VH gene mentioned above, L chain κmix primers were produced from VL mouse sequence at 5' terminal and Ck (κconstant region) sequence, respectively. VL gene was isolated similarly by PCR. Alternatively, L chain λmix primers were produced from 5' terminal VL mouse sequence and Cλ (λ constant region) sequence, respectively. VL gene was isolated similarly by PCR.

Whether or not the combination of VH and VL actually functions was examined by subjecting the purified protein obtained by incorporating the combination into an expression vector at SfiI and XhoI to ELISA test mentioned in the above 2.

The gene sequence was determined based on the instruction of CEQ 2000 DNA Analysis System (BECMAN COULTER).

The amino acid sequence and the base sequence of the clones 1C9, 2E12, 3G11 and 4E11 selected in the secondary screening were identified as follows.

a. Amino Acid Sequence (1) 1C9 Antibody (FIGS. 9 and 10)

SEQ ID NO: 1 (VH); SEQ ID NO: 2 (VH CDR1); SEQ ID NO: 3 (VH CDR2); SEQ ID NO: 4 (VH CDR3); SEQ ID NO: 5 (VL); SEQ ID NO: 6 (VL CDR1); SEQ ID NO: 7 (VL CDR2); SEQ ID NO: 8 (VL CDR3)

(2) 2E12 Antibody (FIGS. 11 and 12)

SEQ ID NO: 9 (VH); SEQ ID NO: 10 (VH CDR1); SEQ ID NO: 11 (VH CDR2); SEQ ID NO: 12 (VH CDR3); SEQ ID NO: 13 (VL); SEQ ID NO: 14 (VL CDR1); SEQ ID NO: 15 (VL CDR2); SEQ ID NO: 16 (VL CDR3)

(3) 3G11 Antibody (FIGS. 13 and 14)

SEQ ID NO: 17 (VH); SEQ ID NO: 18 (VH CDR1); SEQ ID NO: 19 (VH CDR2); SEQ ID NO: 20 (VH CDR3); SEQ ID NO: 21 (VL); SEQ ID NO: 22 (VL CDR1); SEQ ID NO: 23 (VL CDR2); SEQ ID NO: 24 (VL CDR3)

(4) 4E11 Antibody (FIGS. 15 and 16)

SEQ ID NO: 25 (VH); SEQ ID NO: 26 (VH CDR1); SEQ ID NO: 27 (VH CDR2); SEQ ID NO: 28 (VH CDR3); SEQ ID NO: 29 (VL); SEQ ID NO: 30 (VL CDR1); SEQ ID NO: 31 (VL CDR2); SEQ ID NO: 32 (VL CDR3)

b. Base Sequence (1) 1C9 Antibody (FIGS. 9 and 10)

SEQ ID NO: 33 (VH); SEQ ID NO: 34 (VH CDR1); SEQ ID NO: 35 (VH CDR2); SEQ ID NO: 36 (VH CDR3); SEQ ID NO: 37 (VL); SEQ ID NO: 38 (VL CDR1); SEQ ID NO: 39 (VL CDR2); SEQ ID NO: 40 (VL CDR3)

(2) 2E12 Antibody (FIGS. 11 and 12)

SEQ ID NO: 41 (VH); SEQ ID NO: 42 (VH CDR1); SEQ ID NO: 43 (VH CDR2); SEQ ID NO: 44 (VH CDR3); SEQ ID NO: 45 (VL); SEQ ID NO: 46 (VL CDR1); SEQ ID NO: 47 (VL CDR2); SEQ ID NO: 48 (VL CDR3)

(3) 3G11 Antibody (FIGS. 13 and 14)

SEQ ID NO: 49 (VH); SEQ ID NO: 50 (VH CDR1); SEQ ID NO: 51 (VH CDR2); SEQ ID NO: 52 (VH CDR3); SEQ ID NO: 53 (VL); SEQ ID NO: 54 (VL CDR1); SEQ ID NO: 55 (VL CDR2); SEQ ID NO: 56 (VL CDR3)

(4) 4E11 Antibody (FIGS. 15 and 16)

SEQ ID NO: 57 (VH); SEQ ID NO: 58 (VH CDR1); SEQ ID NO: 59 (VH CDR2); SEQ ID NO: 60 (VH CDR3); SEQ ID NO: 61 (VL); SEQ ID NO: 62 (VL CDR1); SEQ ID NO: 63 (VL CDR2); SEQ ID NO: 64 (VL CDR3)

6. Production of Mouse-human Chimeric Antibody 6-1. Isolation of Human γ Chain Constant Region Gene and Human λ Chain Constant Region Gene Human γ chain constant region DNA and human λ chain constant region DNA are obtained from human lymphocyte cDNA library by using as a template a DNA complimentary to a part of each DNA.

6-2. Production of Chimeric H Chain Vector and Chimeric L Chain Vector

Firstly, the human γ-chain constant region DNA and the mouse H chain variable region DNA obtained in the above 5. are ligated, and incorporated into an expression vector "BCMGS Neo vector" (Hajime Toriyama, Bovine papillomavirus vector," Experimental Medicine (supplementary volume), Genetic Engineering Handbook edited by Masami Muramatsu and Hirohito Okayama, YODOSHA CO., LTD., pp. 297-299 (1991)) to form a chimeric H chain vector. Similarly, the human γ-chain constant region DNA and the mouse L chain variable region DNA obtained in the above 5, are ligated, and incorporated into an expression vector "BCMGS Neo vector" to form a chimeric L chain vector (FIG. 17).

6-3. Transfection

The two kinds of vectors (the chimeric H chain vector and the chimeric L chain vector) were concurrently transfected into a CHO (Chinese hamster ovary) cell by the lipofectin method, cultured at 37° C. for a predetermined time, transplanted into a 96-well plate, and selected in DMEM/10% FCS containing 500 μg/ml of neomycin.

The amount of IgG in the culture solution was measured as follows. An anti-human γ-chain (Medical & Biological Laboratories Co., Ltd.: code 103AG) was diluted with PBS to 10 μg/ml, dispensed into a polystyrene microplate in an amount of 100 μl/well, and sensitized at 4° C. over night. Then, blocking was carried out by using 5% BSA/5% sucrose/PBS at 4° C. over night. 100 μl of sample was reacted at 37° C. for one hour, followed by washing with PBS/0.05% TWEEN 20. After washing, 4000-fold diluted peroxidase-labeled anti-human IgG (Medical & Biological Laboratories Co., Ltd.: code 208) was reacted at 37° C. for one hour, followed by washing with PBS/0.05% TWEEN 20. After washing, 100 μl of enzyme-substrate solution was dispensed and reacted at room temperature for 15 minutes. Then, 100 μl of 2N sulfuric acid was dispensed to each well, and A492 was measured. For control, human sera (amount of IgG: 200 ng/ml, 20 ng/ml, 2 ng/ml, and 0.2 ng/ml) were used. Thus, a clone exhibiting the largest amount of expression was selected and the culture supernatant thereof was recovered. From the recovered culture supernatant, an antibody was purified by using a protein A agarose column.

7. Preparation of Human CDR-grafted Antibody 7-1. Design of Human CDR-grafted Antibody For the H chain and the L chain, sequences exhibiting high homology to the H chain and the L chain of the antibody obtained in the above-mentioned 5 are selected from a well-known database (for example, Fasta database search), respectively. Then, a sequence having FRs of these sequences and CDR of an inhibitory antibody is designed.

7-2. Production of Human CDR-grafted Antibody Expression Vector

The H chain variable region DNA and the L chain variable region DNA, which were designed in 7-1), can be prepared as follows.

Figure 18:
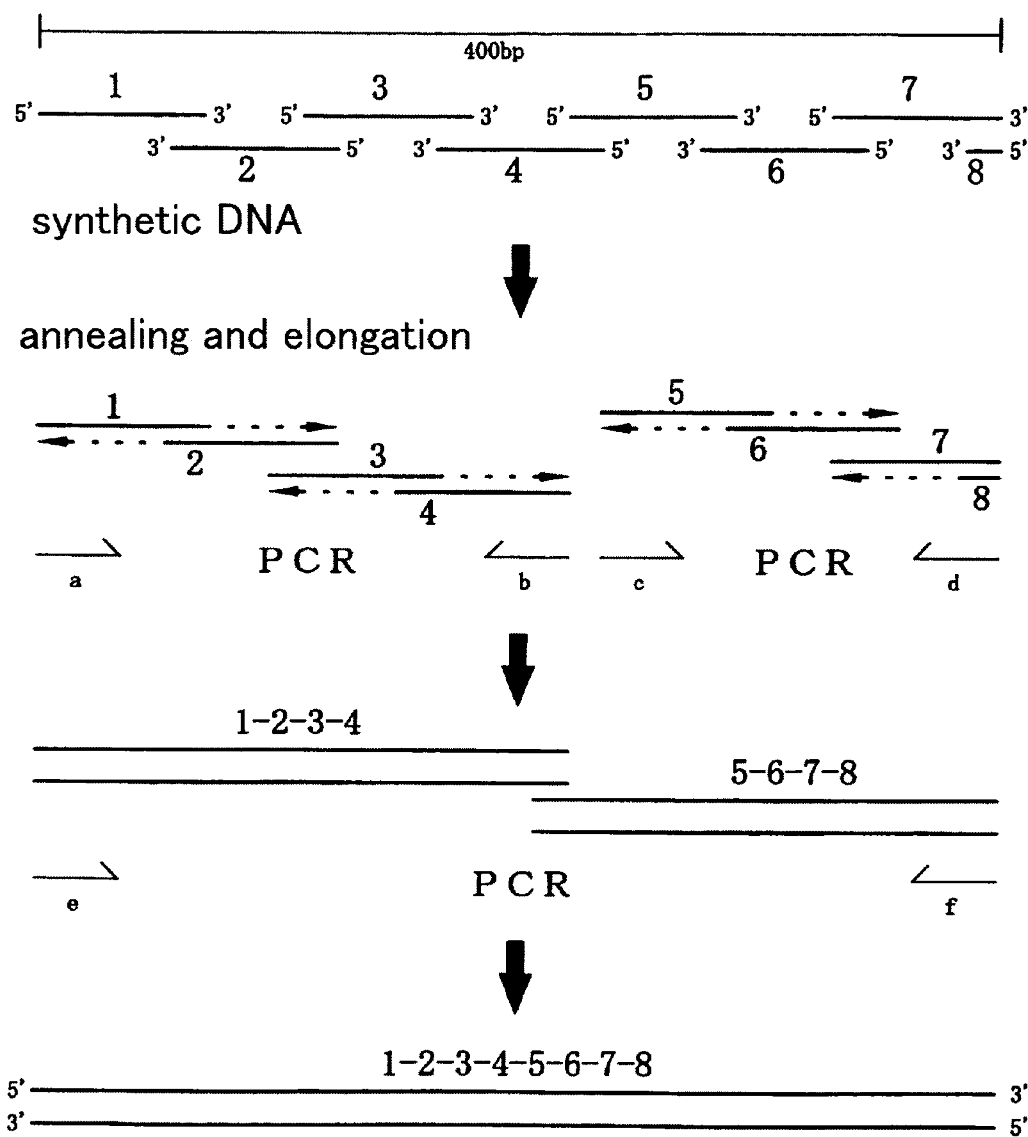
FIG. 18 is a view schematically showing a production method of a human type CDR-grafted antibody variable region DNA.

Firstly, as shown in FIG. 18, eight synthetic DNAs were prepared. These synthetic DNAs are prepared such that they cover about 400 bp of variable regions with about 20 bp of each DNA being overlapped each other. 10 μmol/10 μl of these synthetic DNAs are treated at 100° C. for five minutes, followed by quenching. The synthetic DNAs 1 and 2, 3 and 4, 5 and 6, and 7 and 8 are mixed respectively, heated in a heat block at 65° C. for 30 minutes, left it stand for 12 hours and subjected to slow annealing. Then, 1 μl of 20 mM dNTP, 1 μl of Sequenase (Amersham), 10 μl of 5× Sequenase Buffer are added, and sterile water is added to total amount of 50 μl finally. The mixture is incubated at 37° C. for one hour. The DNA fragments (1-2, 3-4, 5-6, and 7-8) are subjected to an electrophoresis with 2% agarose, cleaved out, and dissolved in 30 μl of sterile water. Then, 1 μl of Pfu polymerase, 5 μl of DMSO and 9 μl of 10×Pfu buffer are added to 2 μl each of the cleaved DNA fragments 1-2 and 3-4, 5-6 and 7-8. Then, sterile water is added to total amount of 90 μl, and subjected to six cycles of PCR under the conditions: at 94° C. for one minute, 55° C. for one minute and 72° C. for two minutes. Then, 1 μl of 10× buffer and 5 μl each of 20 μl primers (a and b, or c and d) are added respectively, and further subjected to 25 cycles of PCR under the conditions: at 94° C. for one minute, 55° C. for one minute and 72° C. for two minutes. Amplified DNA fragments (1-2-3-4 and 5-6-7-8) are cleaved out, dissolved in 30 μl of sterile water, and subjected to six cycles of PCR by using 2 μl of the respective DNAs under the above-mentioned conditions. Then, primers e and f are further added and 25 cycles of PCR are carried out under the above-mentioned conditions. The resultant fragments are cleaved out, cloned into a pT7blueT vector, and the sequence is confirmed.

Subsequently, similar to the above-mentioned 6, an expression vector, "BCMGS Neo vector," a synthetic H chain variable region DNA provided with restriction enzyme site by PCR and the human γ-chain DNA are ligated so as to prepare a CDR H chain vector. Similarly, a CDR L chain vector into which the synthetic L chain variable region DNA and the human λ-chain DNA were incorporated is produced.

7-3. Transfection

The CDR H chain vector and the CDR L chain vector are concurrently transfected into a CHO cell by the lipofectin method, cultured at 37° C. for 12 hours, and replanted into a 96-well plate, and selected in DMEM/10% FCS containing 500 μg/ml of neomycin. Thereafter, a clone exhibiting the largest amount of expression is selected by ELISA. The culture supernatant is recovered and an antibody is purified by using a Protein A agarose column.

INDUSTRIAL APPLICABILITY

The present invention provides information (amino acid sequence and DNA sequence) of an antibody having an inhibitory activity on amyloid fibril formation. Furthermore, an antibody (including an antibody fragment) having such an activity is provided. In particular, based on the information of CDR, a humanized antibody can be produced. These antibodies are effective means for diagnosing, preventing and treating Alzheimer's disease.

While an embodiment of the invention has been described using specific terms, such description is for illustrative purposes only, and it is to be understood that changes and variations may be made without departing from the spirit or scope of the following claims.

Contents of the theses, Publication of patent applications, Patent Publications, and other published documents are herein incorporated by reference in their entity.

The invention claimed is:

1. An isolated antibody comprising a combination of a heavy chain variable region and a light chain variable region selected from the group consisting of (a) a combination of a heavy chain variable region having an amino acid sequence of SEQ ID NO: 17 and having a CDR including a heavy chain CDR1 having an amino acid sequence of SEQ ID NO: 18, a heavy chain CDR2 having an amino acid sequence of SEQ ID NO: 19, and a heavy chain CDR3 having an amino acid sequence of SEQ ID NO: 20, and a light chain variable region having an amino acid sequence of SEQ ID NO: 21 and having a CDR including CDR1 having an amino acid sequence of SEQ ID NO: 22, CDR2 having an amino acid sequence of SEQ ID NO: 23, and CDR3 having an amino acid sequence of SEQ ID NO: 24; and wherein the antibody recognizes GM1 ganglioside-bound amyloid β-protein.

2. The isolated antibody according to claim 1, wherein the antibody is a humanized antibody.

3. The isolated antibody according to claim 1, wherein the antibody is Fab, Fab', $F(ab')_2$, scFv, or dsFv antibody.

4. The isolated antibody according to claim 1, wherein the inhibitory effect in an amyloid β protein polymerization inhibition test in vitro is 50% or more.

* * * * *